(12) United States Patent
Yoneda

(10) Patent No.: US 8,822,163 B2
(45) Date of Patent: Sep. 2, 2014

(54) METHOD FOR MEASURING β-GLUCAN, AND β-GLUCAN-BINDING PROTEIN FOR USE IN THE METHOD

(75) Inventor: Akito Yoneda, Amagasaki (JP)

(73) Assignee: Wako Pure Chemical Industries, Ltd., Osaka (JP)

(*) Notice: Subject to any disclaimer, the term of this patent is extended or adjusted under 35 U.S.C. 154(b) by 46 days.

(21) Appl. No.: 13/257,080

(22) PCT Filed: Mar. 17, 2010

(86) PCT No.: PCT/JP2010/054568
§ 371 (c)(1),
(2), (4) Date: Sep. 16, 2011

(87) PCT Pub. No.: WO2010/107068
PCT Pub. Date: Sep. 23, 2010

(65) Prior Publication Data
US 2012/0009594 A1   Jan. 12, 2012

(30) Foreign Application Priority Data
Mar. 17, 2009 (JP) .................................. 2009-063780

(51) Int. Cl.
 *G01N 33/53* (2006.01)
 *C07K 14/435* (2006.01)
 *G01N 33/569* (2006.01)

(52) U.S. Cl.
CPC ...... *C07K 14/43509* (2013.01); *G01N 2400/24* (2013.01); *G01N 33/56961* (2013.01); *G01N 33/5308* (2013.01); *Y10S 435/935* (2013.01)
USPC ............ 435/7.1; 435/7.92; 435/935; 530/350

(58) Field of Classification Search
None
See application file for complete search history.

(56) References Cited

U.S. PATENT DOCUMENTS

| 5,795,962 | A | 8/1998 | Iwanaga et al. |
| 6,156,519 | A | 12/2000 | Tamura et al. |
| 7,335,515 | B2 | 2/2008 | Tamura et al. |
| 2003/0096329 | A1 | 5/2003 | Tamura et al. |
| 2007/0117169 | A1 | 5/2007 | Tamura et al. |

FOREIGN PATENT DOCUMENTS

| EP | 1312613 | 5/2003 |
| JP | 2003-155298 | 5/2003 |
| JP | 3781771 | 5/2006 |
| JP | 3793573 | 7/2006 |
| JP | 2009-047588 | 3/2009 |

OTHER PUBLICATIONS

Seki et al (J. Biol. Chem. 269:1370-1374. 1994).*
Greenspan et al (Nature Biotechnology 7: 936-937, 1999).*
Chothia et al (The EMBO Journal, 1986, 5/4:823-26).*
Mikayama et al. (Nov.1993. Proc.Natl.Acad.Sci. USA, vol. 90 : 10056-10060).*
Y. Takaki et al., "Duplicated Binding Sites for (1→3)-β-D-Glucan in the Horseshoe Crab Coagulation Factor G," The Journal of Biological Chemistry, vol. 277, No. 16 (2002), p. 14281-14287.
L.M. Graham et al., "Soluble Dectin-1 as a tool to detect β-glucans," Journal of Immunological Methods, vol. 314 (2006), p. 164-169.
Y. Ueda et al., "Kabutogani Taieki Gyoko Inshi Factor G No. β-1, 3-D-Glucan Ninshiki Module to Dojo Saikin *Cellvibrio mixtus* no Tosa Ninshiki Module to no Kozo Ruijisei," Proceeding of the Complement Symposium, vol. 46 (2009), p. 35.

* cited by examiner

*Primary Examiner* — Jennifer Graser
(74) *Attorney, Agent, or Firm* — Hamre, Schumann, Mueller & Larson, P.C.

(57) ABSTRACT

Disclosed are a method for measuring βG comprising the steps of bringing a sample into contact with a βG-binding protein 1 and a βG-binding protein 2, each comprising an amino acid sequence which is identical or substantially identical to an amino acid sequence shown in any one of SEQ ID NO:4, SEQ ID NO:6, SEQ ID NO:8, SEQ ID NO:10, SEQ ID NO:14, SEQ ID NO:16, SEQ ID NO:18, or SEQ ID NO:20, and having the β-glucan binding activity, to form a complex of the βG-binding protein 1, βG in the sample and the βG-binding protein 2, measuring quantity of the complex, and determining βG concentration in the sample based on the quantity of the complex; a reagent and a kit for use in said method; a novel βG-binding protein; a nucleic acid molecule encoding the βG-binding protein; and a method for producing the aforementioned βG-binding protein.

18 Claims, 7 Drawing Sheets

Horseshoe crab *(Limulus polyhemus)* factor G-subunit

Horseshoe crab *(Tachypleus tridentatus)* factor G-subunit

METHOD FOR MEASURING β-GLUCAN, AND β-GLUCAN-BINDING PROTEIN FOR USE IN THE METHOD

TECHNICAL FIELD

The present invention relates to a novel method for measuring β-glucan (hereinafter, abbreviated as "βG") using a novel β-glucan-binding protein and the novel β-glucan-binding protein for use in the method.

BACKGROUND ART

In the mycotic diseases, there are superficial one which develops on the skin and deep-seated one which develops in the internal organ, blood system and lymph system. The deep-seated mycotic disease is a kind of opportunistic infectious disease with which patients who lost their power of resistance (immunodeficiency state) are affected, and leads to extremely serious pathological condition. A representative example of causative microorganism of the deep-seated mycotic disease includes species of *Candida* and *Aspergillus*, and since the βG is present commonly in the cell walls of both species, it is useful to determine blood level of the βG. In the clinical diagnosis, determination of plasma or serum β-glucan level is used for earlier diagnosis of fungal infection, determination of therapeutic effect and prognosis.

The βG has a structure of repeated glucose unit linked by β-(1→3) bond as a main chain, and in some cases it has branched structure with (1→6) bond or (1→4) bond, and has high molecular weight of about several thousands to millions (in this regard, however, distribution is wide). In addition, the βG has a property of binding with βG-binding domain of factor G-subunit α which is present in the hemocyte extract (amebocyte lysate) of horseshoe crab.

The structural analysis of the *Tachypleus* horseshoe crab factor G-subunit α is completed, and its amino acid sequence and nucleotide sequence have been disclosed in the NCBI (National Center for Biotechnology Information) database. In addition, expression of *Tachypleus* horseshoe crab factor G-subunit α by genetic engineering technique has also been succeeded (Patent Literature 3).

The factor G is a precursor of serine proteases, and is activated by binding with βG to initiate a protease cascade of factor G series. And the activated factor G activates proclotting enzyme to clotting enzyme, and finally this results in gel formation. Consequently, in the field of medical, pharmaceutical and microbiological science, the βG detection methods have been developed by utilizing this property of the hemocyte extract of horseshoe crab.

As for the representative example of βG detection method employed primarily at the moment, gelation test and turbidimetric kinetic method through the use of gelation reaction arising out of a solution containing hemocyte extract of horseshoe crab and βG, as well as endpoint synthetic substrate method, kinetic synthetic substrate method and the like are included.

For example, the determination of βG by the turbidimetric kinetic method is carried out as follows. That is, a reagent containing hemocyte extract of horseshoe crab is mixed with a sample containing βG, and the aforementioned mixture is irradiated by light. Subsequently, using an appropriate measuring instrument (for example, spectrophotometer, microplate reader, etc.), the time length of optical change, such as change in transmittance, change in absorbance, variation in a ratio of transmitted light Rt, variation in logarithmic value of the ratio of transmitted light Rt, and the like, required for arriving at a predetermined value (gelation time, Tg) after initiation of light irradiation for the aforementioned mixture is measured. The βG concentration in the sample is determined by fitting the aforementioned time obtained to a standard curve indicating relationship between gelation time and βG concentration which has been made in advance using βG solutions of known concentrations.

The measurement methods using hemocyte extract of horseshoe crab as mentioned above are a method which enables to perform measurement of small quantity of βG in the blood in high sensitivity. However, these methods, on the other hand, have such problems that (1) the measurement results tend to vary depending on tester because the method is carried out manually; (2) due to specific measurement for the βG in the blood, it is necessary to carry out inactivation of endotoxins in the blood or to make the test reagents endotoxin-insensitive; (3) in order to inactivate interfering factors in the blood which interfere the horseshoe crab cascade reaction, it is necessary to carry out pre-treatment of the test sample; (4) the measurement takes a long measurement time (about 90 minutes); (5) since hemocyte extract of horseshoe crab is used, that is, natural material (naturally occurring substance) is used, there is concern about depletion of resources; (6) since hemocyte extract of horseshoe crab is used, that is, natural material is used, it costs to maintain quality of the material stable, and so on.

And so, to solve the above described problems in the measurement methods using protease cascade, some additional new measurement methods have been developed.

For example, there is a method in which a protein consisting of only βG binding domain of the factor G-subunit α is prepared by genetic engineering technology and fluorescently labeled, and using one molecule of the fluorescently-labeled recombinant protein instead of using hemocyte extract of horseshoe crab which is natural material, βG is measured by fluorescence polarization technique (Patent Literature 1). However, the detection sensitivity of this method is about several ng/mL at the highest of the reduced value of pachyman (a kind of βG), and this is insufficient to apply the method to the clinical laboratory tests.

In addition, a method of measurement based on Biacore technique using sensor chip (Non-Patent Literature 1), a method for measuring βG using βG-binding protein having a property of specifically binding to βG and a property of inhibiting activation of horseshoe crab factor G, and an antibody against βG-binding protein which is labeled with a labeling substance (Patent Literature 2) have been reported. It is described in the Patent Literature 2 that the βG-binding protein can be produced by genetic engineering technology.

Although the method using sensor chip measures principally affinity between βG and βG-binding protein, since the measurement is qualitative and operation is cumbersome, there remains a problem in applying this method to the field of laboratory testing.

In addition, since the βG-binding protein used in the method which uses βG-binding protein having a property of inhibiting activation of horseshoe crab factor G and an antibody against βG-binding protein which is labeled with a labeling substance is a natural product, there is a problem that lot difference may occur. In addition, it has not been studied yet whether this method can be applied to the field of laboratory testing. Further, this method has a problem in sensitivity.

Still further, an invention relating to "A kit for detecting fungi, comprising one domain or a plurality of domains derived from a Z1 domain and/or a Z2 domain of a factor G subunit α Xln for horseshoe crab of which the cysteine residue is replaced by other amino acid, and comprising a recombinant protein capable of binding to β-1,3-glucan" has also been known (Patent Literature 4).

This method is a method for detecting fungi by contacting a kind of recombinant protein having the above described property with a sample comprising fungi. However, a method for measuring βG using the aforementioned protein (including sandwich method) has not been studied.

Using two molecules of Dectin 1 which is known as a βG receptor, a method for measuring βG by ELISA and the like is also known (Non-Patent Literature 2). However, this method has also not attained to the level of sensitivity required for laboratory testing.

Further, among bacteria such as cellulolytic bacterium of *Fibrobacter succinogenes*, one which possesses cellulose-binding protein is known. A region in the cellulose-binding protein where the protein binds to cellulose is referred to as cellulose binding domain (CBD). The CBD is further classified into plural subfamilies (CBD I to X) according to the characteristic of an amino acid sequence (*Advances in Microbial Physiology*, vol. 37, p. 1-81, 1995). In CBDs, there are ones which have a xylanase Z-like domain having property of binding to βG. However, not necessarily all CBDs have the xylanase Z-like domain. In addition, cellulose which is a target of binding by CBD is (1→4)-β-D-glucan, however, βG in plasma which is a measurement object in clinical testing is (1→3)-β-D-glucan. Therefore, it has not been clarified whether the CBD can be utilized for measuring βG in the field of clinical testing even if the one which have the xylanase Z-like domain is present in the CBD.

As described above, all these methods had various problems when βG was intended to be measured specifically, and particularly, to utilize the method for clinical testing.

CITATION LIST

Patent Literature
  Patent Literature 1: JP-A-2003-155298;
  Patent Literature 2: JP-B-3793573;
  Patent Literature 3: JP-B-3781771;
  Patent Literature 4: JP-A-2009-47588.
Non-Patent Literature
  Non-patent Literature 1: Takaki Y. et al., J. Biol. Chem., 2002, vol. 277, p. 14281-14287;
  Non-patent Literature 2: Graham L. M. et. al., J. Immunol. Methods, 2006, vol. 314(1-2), p. 164-169.

SUMMARY OF INVENTION

Problem to be Solved by the Invention

The present invention was made in view of the above described situation, and an object of the present invention is to provide a method for measuring βG which has equivalent sensitivity and specificity to the conventional reagent with utilizing the protease cascade, and has solved the above described various problems.

Means for Solving the Problem

The present invention is made for the purpose of solving the above described problems, and comprises the following constitutions.
(1) A method for measuring β-glucan (hereinafter, abbreviated as "βG"), which comprises:
  (i) contacting a sample with protein 1 comprising an amino acid sequence which is identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity (hereinafter, abbreviated as "βG-binding protein 1"), and also protein 2 comprising an amino acid sequence which is identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity (hereinafter, abbreviated as "βG-binding protein 2"), to form a complex of the βG-binding protein 1, βG in the sample and the βG-binding protein 2;
  (ii) measuring quantity of the aforementioned complex; and
  (iii) determining βG concentration in the sample based on the quantity of the complex obtained.
(2) A reagent for measurement of βG containing a protein comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having a β-glucan binding activity.
(3) A kit for measuring β-glucan comprising the followings as constituents:
  (i) a reagent containing a protein 1 comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity;
  (ii) a reagent containing a protein 2 comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity.
(4) A protein comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having a β-glucan binding activity.
(5) A nucleic acid molecule comprising a nucleotide sequence identical or substantially identical to a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19.
(6) A nucleic acid molecule encoding a protein comprising an amino acid sequence identical or substantially identical to an amino acid sequence shown in any one of SEQ ID NO: 2, SEQ ID NO: 4, SEQ ID NO: 6, SEQ ID NO: 8, SEQ ID NO: 10, SEQ ID NO: 14, or SEQ ID NO: 20, and having a β-glucan binding activity.
(7) A recombinant construct incorporating therein the nucleic acid molecule described in the above (5) or (6).
(8) A transformant or a transductant, which is transformed or transduced by the recombinant construct described in the above (7).
(9) A process for producing a protein comprising an amino acid sequence identical or substantially identical to an amino acid sequence shown in any one of SEQ ID NO: 2, SEQ ID NO: 4, SEQ ID NO: 6, SEQ ID NO: 8, SEQ ID NO: 10, SEQ ID NO: 14, or SEQ ID NO: 20, and having a β-glucan binding activity, characterized in that the transformant or the transductant of the above described (8) is cultured and the protein is separated from the resulting culture.

The present inventor considered, on the way of intensive study for the purpose of solving the problems as described above, that, taking notice of βG binding domain which was present in the horseshoe crab factor G subunit α and that it was a dimer, it might be possible to measure βG by using the fragment of subunit α comprising this domain structure. In addition, the present inventor also considered that such subunit α fragment could be obtained as a recombinant product (recombinant protein) by genetic engineering technique, and studied further, and as a consequence, a βG measurement system based on sandwich method using the fragment of aforementioned subunit α was established. That is, it was found that a fragment suitable for the measurement of βG is present in the fragments of subunit α with a particular amino acid sequence and having at least monomer structure of the βG binding domain, and further, a βG measurement system based on sandwich method using two molecules of these fragments of subunit α was established, and thus the present invention was completed.

Effect of the Invention

The present invention is directed to provide a method for measuring βG using two molecules of βG-binding protein which has a specific amino acid sequence and a reagent and a kit for use in the measurement, as well as a recombinant βG-binding protein which possesses specific amino acid sequence and producing method thereof. According to the method for measuring βG of the present invention, βG can be measured in high sensitivity yet with specificity as compared to the conventional methods. In addition, even if it is a case where βG in a sample containing protease is measured, it is not necessary to carry out the pretreatment for deactivating the protease in the sample in advance. Moreover, because of having a high sensitivity, the method can bring about such an effect that it can be employed also for a laboratory testing.

Further, since it is not necessary to use natural material if the method of measurement of the present invention is carried out using recombinant protein of the present invention, there is no lot difference of the reagent to be used, and the effect that specific measurement of βG can be performed stably in high measurement sensitivity will be realized.

Still further, the measurement method of the present invention can be applied not only to manual procedures but also to the measurement employing automated analyzers.

EMBODIMENTS FOR CARRYING OUT THE INVENTION

Figure 1:
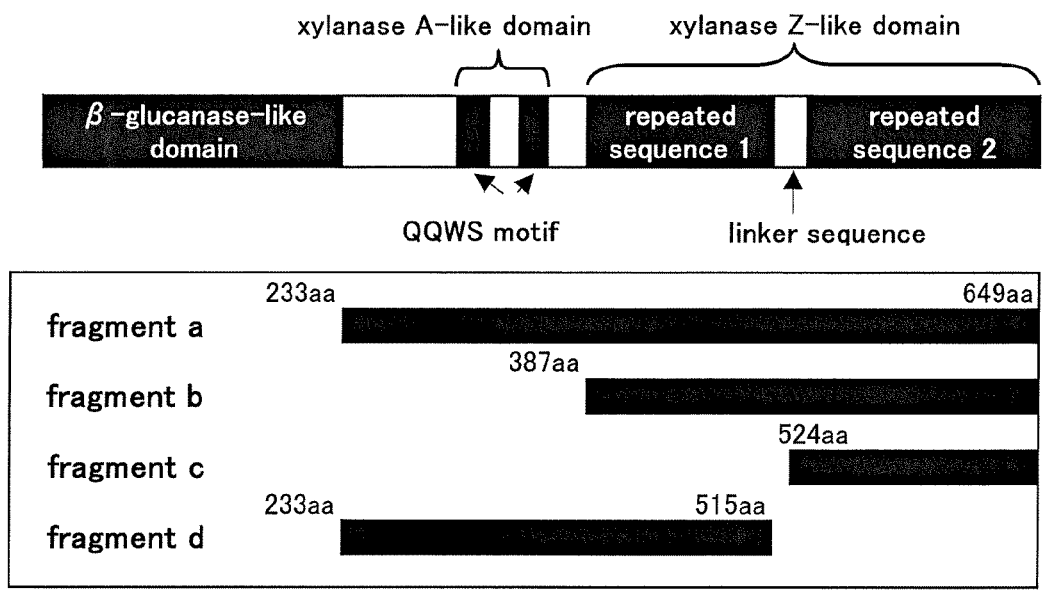
FIG. 1 shows a schematic diagram of the factor G-subunit α of horseshoe crab (*Limulus polyphemus*) and fragments thereof. The upper panel of FIG. 1 shows the schematic diagram of the factor G-subunit α of horseshoe crab (*Limulus polyphemus*). Lower panel of FIG. 1 shows the schematic diagram of the fragments derived from the factor G-subunit α of horseshoe crab (*Limulus polyphemus*), and the positions of N-terminal and C-terminal amino acid of each fragment on the factor G-subunit α of horseshoe crab (*Limulus polyphemus*), respectively.

The βG involved in the present invention is not particularly limited, as long as it is polysaccharide comprising βG as a constituent. For example, ones which have a property of triggering enzyme reaction of hemocyte extract of horseshoe crab are included. Specifically, for example, natural polysaccharides obtained from the cell wall and the like of various bacteria (for example, genus *Alcaligenes, Agrobacterium*, and the like), yeast (for example, genus *Saccharomyces, Candida, Cryptococcus, Trichosporon, Rhodotorula*, and the like), fungus (genus *Aspergillus, Mucor, Penicillium, Trichophyton, Sporothrix, Phialophora*, and the like), Ray funguses (genus *Actinomyces, Nocardia*, and the like), and mushrooms (for example, *Lentinula edodes, Schizophyllum commune, Trametes versicoloi* and the like), more specifically, for example, curdlan, pachyman, sclerotan, lentinan, schizophyllan, coriolan, and the like, or a storage glucan of algae (for example, brown algae, euglena, diatoms, and the like), and yet specifically, for example, laminaran, paramylum and the like are included.

"Protein 1 comprising an amino acid sequence which is identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity" (βG-binding protein 1) and "protein 2 comprising an amino acid sequence which is identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having a β-glucan binding activity" (βG-binding protein 2) may be same to or different from each other, and those may be synthetic protein.

In addition, the "βG-binding protein 1" and the "βG-binding protein 2" are sometimes put together and described as "βG-binding protein involved in the present invention" or simply as "βG-binding protein", hereafter.

The "βG-binding protein 1" and the "βG-binding protein 2" are the ones derived from factor G-subunit α of hemocyte of horseshoe crab.

The amino acid sequence of the factor G-subunit α of horseshoe crab (*Limulus polyphemus*) was clarified by the present inventor. It comprises an amino acid sequence shown in SEQ ID NO: 2 consisted of about 649 amino acids, and encoded by a nucleotide sequence shown in SEQ ID NO: 1, and there exists a β-1,3-glucanase-like domain on the N-terminal side, dimeric xylanase Z-like domain (XlnZ) which are presumed to be βG binding domain on the C-terminal side, and a xylanase A-like domain in the center of the sequence. In the xylanase A-like domain, there is twice repetition of QQWS (Gln-Gln-Trp-Ser) motif which are a structural motif.

In addition, based on the knowledge of the amino acid sequence of the factor G-subunit α of horseshoe crab (*Limulus polyphemus*) obtained by the present inventor, four kinds of fragments of the factor G-subunit α of horseshoe crab (*Limulus polyphemus*) each of which comprises the xylanase Z-like domain (XlnZ) supposed to be a βG binding domain in the structure were designed. That is, those are:

horseshoe crab (*Limulus polyphemus*) factor G-subunit α fragment-a (hereafter, sometimes indicated simply as "fragment-a");
horseshoe crab (*Limulus polyphemus*) factor G-subunit α fragment-b (hereafter, sometimes indicated simply as "fragment-b");
horseshoe crab (*Limulus polyphemus*) factor G-subunit α fragment-c (hereafter, sometimes indicated simply as "fragment-c"); and
horseshoe crab (*Limulus polyphemus*) factor G-subunit α fragment-d (hereafter, sometimes indicated simply as "fragment-d").

The schematic diagram of the factor G-subunit α of horseshoe crab (*Limulus polyphemus*) which was clarified by the present inventor is shown in the upper panel of FIG. 1. In addition, the schematic diagram of the fragments derived from the factor G-subunit α of horseshoe crab (*Limulus polyphemus*), and the positions of N-terminal and C-terminal amino acid of each fragment on the factor G-subunit α of horseshoe crab (*Limulus polyphemus*) are shown collectively in the lower panel of FIG. 1.

The structure, etc. of each fragment are explained below.

The fragment-a consists of an amino acid sequence shown in SEQ ID NO: 4 which is encoded by a nucleotide sequence shown in SEQ ID NO: 3. It corresponds to the part of amino acid sequence of the 233rd to the 649th from N-terminal of the amino acid sequence of the factor G-subunit α of horseshoe crab (*Limulus polyphemus*) shown in SEQ ID NO: 2. It has a xylanase A-like domain (two QQWS motifs exist) and a dimeric xylanase Z-like domain (XlnZ).

The fragment-b consists of an amino acid sequence shown in SEQ ID NO: 6 which is encoded by a nucleotide sequence shown in SEQ ID NO: 5. It corresponds to the part of amino acid sequence of the 387th to the 649th from N-terminal of the amino acid sequence of the factor G-subunit α of horseshoe crab (*Limulus polyphemus*) shown in SEQ ID NO: 2. It has a dimeric xylanase Z-like domain (XlnZ).

The fragment-c consists of an amino acid sequence shown in SEQ ID NO: 8 which is encoded by a nucleotide sequence shown in SEQ ID NO: 7. It corresponds to the part of amino acid sequence of the 524th to the 649th from N-terminal of the amino acid sequence of the factor G-subunit α of horseshoe crab (*Limulus polyphemus*) shown in SEQ ID NO: 2. It has one xylanase Z-like domain in C-terminal side of the dimeric xylanase Z-like domain (XlnZ).

The fragment-d consists of an amino acid sequence shown in SEQ ID NO: 10 which is encoded by a nucleotide sequence shown in SEQ ID NO: 9. It corresponds to the part of amino acid sequence of the 233rd to the 515th from N-terminal of the amino acid sequence of the factor G-subunit α of horseshoe crab (*Limulus polyphemus*) shown in SEQ ID NO: 2. It has a xylanase A-like domain (two QQWS motifs exist) and one xylanase Z-like domain in N-terminal side of the dimeric xylanase Z-like domain (XlnZ).

On the other hand, the structural analysis of the factor G-subunit α of horseshoe crab (*Tachypleus tridentatus*) is completed and the amino acid sequence and nucleotide sequence are disclosed in the NCBI (National Center for Biotechnology Information) database. It comprises a signal peptide consisting of 19 amino acids and an amino acid sequence which consists of 673 amino acids shown in SEQ ID NO: 12 and which is encoded by a nucleotide sequence shown herein by SEQ ID NO: 11. There exist a β-1,3-glucanase-like domain on the N-terminal side, dimeric xylanase Z-like domain (XlnZ) which are presumed to be βG binding domain on the C-terminal side, and a xylanase A-like domain in the center of the sequence. In the xylanase A-like domain, there is three-times repetition of QQWS (Gln-Gln-Trp-Ser) motif which are a structural motif. In addition, DNA which encodes the polypeptide of the factor G-subunit α of horseshoe crab (*Tachypleus tridentatus*) is disclosed in JP-B-3781771 (Patent Literature 3). The aforementioned polypeptide consists of 654 amino acids, and lacks the signal peptide part of the amino acids sequence disclosed in the NCBI database.

Moreover, the present inventor designed four kinds of fragment of the factor G-subunit α of horseshoe crab (*Tachypleus tridentatus*) each of which comprises the xylanase Z-like domain (XlnZ) supposed to be a βG binding domain in the structure were designed by the same way as in designing fragments of the factor G-subunit α of horseshoe crab (*Limulus polyphemus*). That is, those are:

horseshoe crab (*Tachypleus tridentatus*) factor G-subunit α fragment-e (hereafter, sometimes indicated simply as "fragment-e");
horseshoe crab (*Tachypleus tridentatus*) factor G-subunit α fragment-f (hereafter, sometimes indicated simply as "fragment-f");
horseshoe crab (*Tachypleus tridentatus*) factor G-subunit α fragment-g (hereafter, sometimes indicated simply as "fragment-g"); and
horseshoe crab (*Tachypleus tridentatus*) factor G-subunit α fragment-h (hereafter, sometimes indicated simply as "fragment-h").

Figure 2:
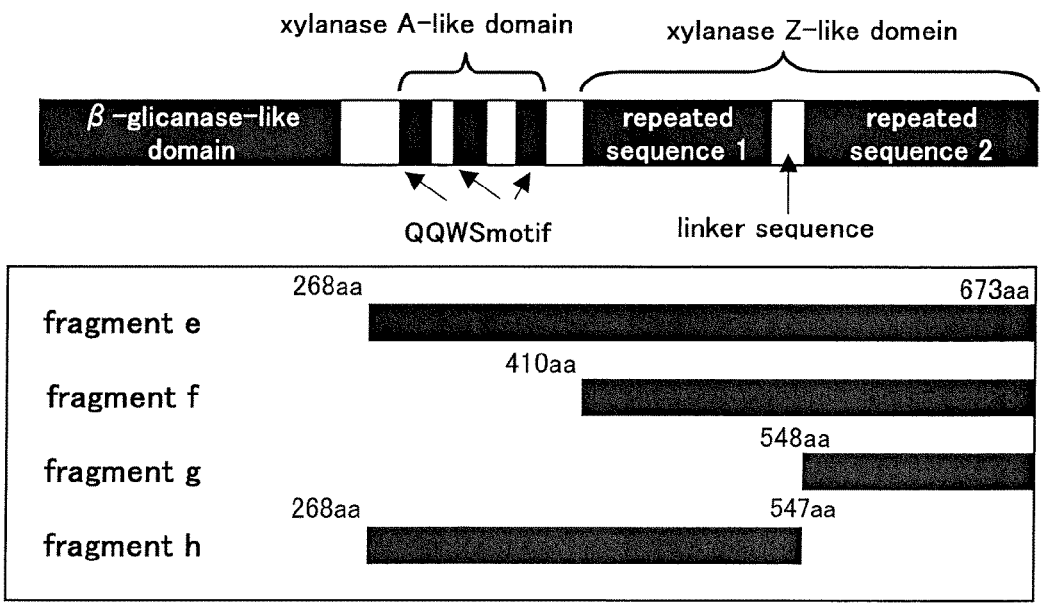
FIG. 2 shows a schematic diagram of the factor G-subunit α of horseshoe crab (*Tachypleus tridentatus*) and fragments thereof. The upper panel of FIG. 2 shows the schematic diagram of the factor G-subunit α of horseshoe crab (*Tachypleus tridentatus*). Lower panel of FIG. 2 shows the schematic diagram of the fragments derived from the factor G-subunit α of horseshoe crab (*Tachypleus tridentatus*), and the positions of N-terminal and C-terminal amino acid of each fragment on the factor G-subunit α of horseshoe crab (*Tachypleus tridentatus*), respectively.

The schematic diagram of the factor G-subunit α of horseshoe crab (*Tachypleus tridentatus*) is shown in the upper panel of FIG. 2. In addition, the schematic diagram of the fragments derived from the factor G-subunit α of horseshoe crab (*Tachypleus tridentatus*), and the positions of N-terminal and C-terminal amino acid of each fragment on the factor G-subunit α of horseshoe crab (*Tachypleus tridentatus*) are shown collectively in the lower panel of FIG. 2. Among these, fragment-e and fragment-h are designed for the first time by the present inventor. In contrast, fragment-f and fragment-g are well-known, and there is an instance, for example, that the measurement of βG was carried out using them labeled with labeling substance. However, the measurement of βG by sandwich method using two molecules of these fragments or two molecules of this fragment and other fragment has not been known.

The structure, and the like of each fragment are explained below.

The fragment-e consists of an amino acid sequence shown in SEQ ID NO: 14 which is encoded by a nucleotide sequence shown in SEQ ID NO: 13. It corresponds to the part of amino acid sequence of the 268th to the 673rd from N-terminal of the amino acid sequence of the factor G-subunit α of horseshoe crab (*Tachypleus tridentatus*) shown in SEQ ID NO: 12. It has a xylanase A-like domain (three QQWS motifs exist) and a dimeric xylanase Z-like domain (XlnZ).

The fragment-f consists of an amino acid sequence shown in SEQ ID NO: 16 which is encoded by a nucleotide sequence shown in SEQ ID NO: 15. It corresponds to the part of amino acid sequence of the 410th to the 673rd from N-terminal of the amino acid sequence of the factor G-subunit α of horseshoe crab (*Tachypleus tridentatus*) shown in SEQ ID NO: 12. It has a dimeric xylanase Z-like domain (XlnZ).

The fragment-g consists of an amino acid sequence shown in SEQ ID NO: 18 which is encoded by a nucleotide sequence shown in SEQ ID NO: 17. It corresponds to the part of amino acid sequence of the 548th to the 673rd from N-terminal of the amino acid sequence of the factor G-subunit α of horseshoe crab (*Tachypleus tridentatus*) shown in SEQ ID NO: 12. It has one xylanase Z-like domain in C-terminal side of the dimeric xylanase Z-like domain (XlnZ).

The fragment-h consists of an amino acid sequence shown in SEQ ID NO: 20 which is encoded by a nucleotide sequence shown in SEQ ID NO: 19. It corresponds to the part of amino acid sequence of the 268th to the 547th from N-terminal of the amino acid sequence of the factor G-subunit α of horseshoe crab (*Tachypleus tridentatus*) shown in SEQ ID NO: 12. It has a xylanase A-like domain (three QQWS motifs exist) and one xylanase Z-like domain in N-terminal side of the dimeric xylanase Z-like domain (XlnZ).

The SEQ ID NO of amino acid sequence and the SEQ ID NO of nucleotide sequence which encodes the amino acid sequence of the factor G-subunit α of horseshoe crab (*Limulus polyphemus*) and the fragments thereof, as well as of the factor G-subunit α of horseshoe crab (*Tachypleus tridentatus*) and the fragments thereof are shown collectively in the following Table 1.

TABLE 1

| SEQ ID NO of nucleotide sequence | SEQ ID NO of amino acid sequence | Kind of fragment from horseshoe crab factor G-subunit α |
|---|---|---|
| 1 | 2 | *Limulus polyphemus* factor G-subunit α |
| 3 | 4 | Fragment-a derived from *Limulus polyphemus* factor G-subunit α |
| 5 | 6 | Fragment-b derived from *Limulus polyphemus* factor G-subunit α |
| 7 | 8 | Fragment-c derived from *Limulus polyphemus* factor G-subunit α |
| 9 | 10 | Fragment-d derived from *Limulus polyphemus* factor G-subunit α |
| 11 | 12 | *Tachypleus tridentatus* factor G-subunit α |

TABLE 1-continued

| SEQ ID NO of nucleotide sequence | SEQ ID NO of amino acid sequence | Kind of fragment from horseshoe crab factor G-subunit α |
|---|---|---|
| 13 | 14 | Fragment-e derived from *Tachypleus tridentatus* factor G-subunit α |
| 15 | 16 | Fragment-f derived from *Tachypleus tridentatus* factor G-subunit α |
| 17 | 18 | Fragment-g derived from *Tachypleus tridentatus* factor G-subunit α |
| 19 | 20 | Fragment-h derived from *Tachypleus tridentatus* factor G-subunit α |

The "protein comprising an amino acid sequence which is identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having the β-glucan binding activity" using in the measurement method of the present invention is, corresponds to, the above described respective fragments of the factor G-subunit α of horseshoe crab (*Limulus polyphemus*) or the respective fragments of the factor G-subunit α of horseshoe crab (*Tachypleus tridentatus*).

In addition, the "amino acid sequence which is substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20" used in the measurement method of the present invention includes the amino acid sequence which has a homology of about 70% or more, preferably about 80% or more, more preferably about 90% or more, and further preferably about 95% or more to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having the β-glucan binding activity.

Moreover, the "protein comprising an amino acid sequence substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20" includes, for example, the protein which has an amino acid sequence substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having the β-glucan binding activity.

In more specifically, it is, for example, a protein in which 1 to 5 (preferably, 1 to 3) amino acids are replaced or deleted in the amino acid sequence shown in SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, or 1 to 5 (preferably, 1 to 3) amino acids are inserted or added to the aforementioned amino acid sequence, and which has the β-glucan binding activity. The position which gives substitution, deletion, insertion, addition, and the like to the amino acids sequence which constitutes the aforementioned protein is optional as long as the affinity of the protein for βG is not affected thereby.

Moreover, substitution, deletion, insertion, and addition may take place in multiple points of a single amino acid sequence, as long as the affinity of the aforementioned protein for βG is not affected thereby.

Preferred examples of the βG-binding protein 1 and the βG-binding protein 2 to be used for the measurement method of the present invention include fragment-a, fragment-b, fragment-c, fragment-d, fragment-e, fragment-f, fragment-g, and fragment-h involved in the present invention. Considering easiness of acquisition of recombinant product, fragment-a, fragment-b, fragment-e, and fragment-f are particularly preferable.

In addition, in the case where a βG-binding protein involved in the present invention is labeled with a labeling substance and the labeled βG-binding protein is used for the measurement of βG, the following βG-binding protein is more preferable. That is, it is better for βG-binding protein to have an enough length (the number of amine acid) between the site of labeling substance being bound and the βG binding site in the βG-binding protein, so that the binding of βG-binding protein to βG is not interfered by the labeling substance. Furthermore, when the βG-binding protein is used for sandwich method, the longer distance (larger number of amino acid) may also provide a higher measurement sensitivity. Taking the above point into consideration, as for the βG-binding protein involved in the present invention, fragment-a, fragment-b, fragment-e, and fragment-f are preferable, and fragment-a or fragment-b is particularly preferable.

In addition, although the βG-binding protein used for the above described βG measurement method of the present invention does not have a β-glucanase-like domain of horseshoe crab factor G-subunit α, use of this βG-binding protein for the βG measurement method provides the following advantages.

That is, as described above, since the horseshoe crab hemocyte extract is a natural product, even if the horseshoe crab hemocyte extract, or factor G, factor G-subunit α or the like isolated therefrom is intended to be used for measurement of βG, lot difference tends to come out. In addition, because it is a natural product, it cannot be denied that there is a risk of unstable supply in the future. Therefore, if the recombinant product which possesses binding activity to the βG is obtained, such a problem can also be solved.

And so, the present inventors have studied intensively to obtain a recombinant protein which possesses binding activity to the βG As a result, although the reason has not been clarified, a βG-binding protein which is lacking the glucanase-like domain of horseshoe crab factor G-subunit α can be expressed effectively, particularly when the protein is expressed using *E. coli* as a host.

As will be described later, the βG-binding protein to be used for the βG measurement method of the present invention can, of course, be expressed also when mammalian cell, insect cell, or the like is used as a host cell. However, for example, when yeast is used as a host cell, an additional process for removing βG-binding protein of yeast origin from expressed protein will be needed, because yeast cell has βG-binding protein endogenously. Also, when an insect cell is used as a host, there is a problem that secreted expressed protein may be contaminated with bovine serum albumin contained in the medium with which the insect cells are cultured.

However, since *E. coli* cell does not have βG, there is no risk that the protein expressed by *E. coli* is contaminated with endogenous βG. Furthermore, as is known well, *E. coli* has such advantages as compared with other cells that it is easy to manipulate; it is easy to propagate; growth rate is fast; handling cost is cheap; and special culturing facility is not required. Therefore, if *E. coli* is used as a host, there is an advantage that recombinant protein can be manufactured fast, stably and at a low cost.

Therefore, the βG-binding protein involved in the present application which lacks the glucanase-like domain of horseshoe crab factor G-subunit α is also excellent in that it can be expressed when *E. coli* is used as a host.

The method for measuring βG of the present invention is accomplished by the following procedures:

(1) a sample is reacted with βG-binding protein 1 and βG-binding protein 2 to form a complex of βG-binding protein 1, βG in a sample and βG-binding protein 2;

(2) quantity of the aforementioned complex is measured; and (3) βG concentration in the sample is determined based on the quantity of the complex obtained.

The principle of the measurement method involved in the present invention is so-called sandwich technique in which measurement is carried out using βG-binding protein 1 and βG-binding protein 2.

For example, it is the sandwich technique carried out in the usual immunochromatography method, a latex method, and an enzyme immunoassay method (EIA method), and is the method using the βG-binding protein 1 and the βG-binding protein 2 instead of antibody or antigen. In addition, the application to Micro-TAS (Micro-Total Analysis Systems: μ-TAS) is also possible.

The formed complex can be measured either by a heterogeneous method in which BF separation is carried out using insoluble carrier or the like, or by a homogeneous method in which BF separation is not carried out.

Hereinafter, examples of embodiment of the present invention will be described. It should be noted that after respective operations, an operation to remove unwanted substance (washing or the like) may be carried out, if necessary.

I-1. Method Using Free βG-Binding Protein (1):

(i) a sample is brought into contact with free βG-binding protein 1 (not immobilized to an insoluble carrier) and free βG-binding protein 2 (not immobilized to an insoluble carrier), to form a complex of the βG-binding protein 1, βG in the sample and the βG-binding protein 2;

(ii) quantity of the aforementioned complex is measured; and (iii) βG concentration in the sample is determined based on the quantity of the complex obtained.

I-2. Method Using Free βG-Binding Protein (2):

(i) a sample is brought into contact with free βG-binding protein 1 (not immobilized to an insoluble carrier) to form a complex-1 of βG in the sample and the βG-binding protein 1; then (ii) the aforementioned complex-1 is brought into contact with free βG-binding protein 2 (not immobilized to an insoluble carrier) to form a complex-2 of the βG-binding protein 1, βG in the sample and the βG-binding protein 2; then (iii) quantity of the aforementioned complex-2 is measured; and (iv) βG concentration in the sample is determined based on the quantity of the aforementioned complex-2 obtained.

II-1. Method Using an Immobilized βG-Binding Protein 1 to an Insoluble Carrier and a Free Non-Labeled βG-Binding Protein 2 (1):

(i) a sample is brought into contact with an immobilized βG-binding protein 1 to an insoluble carrier and a free non-labeled βG-binding protein 2, to form a complex of the immobilized βG-binding protein 1 to an insoluble carrier, βG in the sample and the non-labeled βG-binding protein 2;

(ii) quantity of the aforementioned complex is measured; and (iii) βG concentration in the sample is determined based on the quantity of the aforementioned complex obtained.

II-2. Method Using an Immobilized βG-Binding Protein 1 to an Insoluble Carrier and a Free Non-Labeled βG-Binding Protein 2 (2):

(i) a sample is brought into contact with an immobilized βG-binding protein 1 to an insoluble carrier to form a complex-1 of the immobilized βG-binding protein 1 to an insoluble carrier and βG in the sample; then (ii) the aforementioned complex-1 is brought into contact with a free non-labeled βG-binding protein 2, to form a complex-2 of the complex-1 and the non-labeled βG-binding protein 2; then (iii) quantity of the aforementioned complex-2 is measured; and (iv) βG concentration in the sample is determined based on the quantity of the aforementioned complex-2.

III-1. Method Using a Free βG-Binding Protein 1 and a Free βG-Binding Protein 2 Labeled with a Labeling Substance (1):

(i) a sample is brought into contact with a free βG-binding protein 1 and a free βG-binding protein 2 labeled with a labeling substance, to form a complex of the βG-binding protein 1, βG in the sample and the labeled βG-binding protein 2;

(iii) quantity of the labeling substance in the aforementioned complex is measured; and (iv) βG concentration in the sample is determined based on the quantity of the labeling substance obtained.

III-2. Method Using a Free βG-Binding Protein 1 and a Free βG-Binding Protein 2 Labeled with a Labeling Substance (2):

(i) a sample is brought into contact with a free βG-binding protein 1 to form a complex-1 of the βG in the sample and βG-binding protein 1; then (ii) the aforementioned complex-1 is brought into contact with a free βG-binding protein 2 labeled with a labeling substance, to form a complex-2 of the complex-1 and the labeled βG-binding protein 2; then (iii) quantity of the labeling substance in the aforementioned complex-2 is measured; and (iv) βG concentration in the sample is determined based on the quantity of the labeling substance obtained.

IV-1. Method Using an Immobilized βG-Binding Protein 1 to an Insoluble Carrier and a Free βG-Binding Protein Labeled with a Labeling Substance (1):

(i) a sample is brought into contact with an immobilized βG-binding protein 1 to an insoluble carrier and a free βG-binding protein labeled with a labeling substance, to form a complex of the immobilized βG-binding protein 1 to an insoluble carrier, βG in the sample and the labeled βG-binding protein 2;

(iii) quantity of the labeling substance in the aforementioned complex is measured; and (iv) βG concentration in the sample is determined based on the quantity of the labeling substance obtained.

IV-2. Method Using an Immobilized βG-Binding Protein 1 to an Insoluble Carrier and a Free βG-Binding Protein Labeled with a Labeling Substance (2):

(i) a sample is brought into contact with an immobilized βG-binding protein 1 to an insoluble carrier to form a complex-1 of the immobilized βG-binding protein 1 to the insoluble carrier and the βG in the sample; then (ii) the aforementioned complex-1 is brought into contact with a free βG-binding protein 2 labeled with a labeling substance, to form a complex-2 of the complex-1 and the labeled βG-binding protein 2; then (iii) quantity of the labeling substance in the aforementioned complex-2 is measured; and (iv) βG concentration in the sample is determined based on the quantity of the labeling substance obtained.

V-1. Method Using a Free βG-Binding Protein 1 Labeled with a Labeling Substance and a Free βG-Binding Protein 2 Labeled with a Labeling Substance (1):

(i) a sample is brought into contact with a free βG-binding protein 1 labeled with a labeling substance and a free βG-binding protein 2 labeled with a labeling substance to form a complex of the βG-binding protein 1, the βG in the sample and the labeled βG-binding protein 2;

(iii) quantity of the labeling substance in the aforementioned complex is measured; and (iv) βG concentration in the sample is determined based on the quantity of the labeling substance obtained.

V-2. Method Using a Free βG-Binding Protein 1 Labeled with a Labeling Substance and a Free βG-Binding Protein 2 Labeled with a Labeling Substance (2):

(i) a sample is brought into contact with a free βG-binding protein 1 labeled with a labeling substance, to form a complex-1 of the βG in the sample and the labeled βG-binding protein 1; then (ii) the aforementioned complex-1 is brought into contact with a free βG-binding protein 2 labeled with a labeling substance, to form a complex-2 of the complex-1 and the labeled βG-binding protein 2; then (iii) quantity of the labeling substance in the aforementioned complex-2 is measured; and (iv) βG concentration in the sample is determined based on the quantity of the labeling substance obtained.

VI-1. Method Using an Immobilized βG-Binding Protein 1 to an Insoluble Carrier Such as Latex Particle and an Immobilized βG-Binding Protein 2 to an Insoluble Carrier Such as Latex Particle (1):

(i) a sample is brought into contact with an immobilized βG-binding protein 1 to an insoluble carrier such as latex particle and an immobilized βG-binding protein 2 to an insoluble carrier such as latex particle, to form a complex of the immobilized βG-binding protein 1 to an insoluble carrier such as latex particle, the βG in the sample and the immobilized βG-binding protein 2 to an insoluble carrier such as latex particle;

(iii) quantity of the aforementioned complex is measured; and (iv) βG concentration in the sample is determined based on the quantity of the aforementioned complex obtained.

VI-2. Method Using an Immobilized βG-Binding Protein 1 to an Insoluble Carrier Such as Latex Particle and an Immobilized βG-Binding Protein 2 to an Insoluble Carrier Such as Latex Particle (2):

(i) a sample is brought into contact with an immobilized βG-binding protein 1 to an insoluble carrier such as latex particle, to form a complex-1 of the immobilized βG-binding protein 1 to an insoluble carrier such as latex particle and the βG in the sample; then (ii) the aforementioned complex-1 is brought into contact with an immobilized βG-binding protein 2 to an insoluble carrier such as latex particle, to form a complex-2 of the complex-1 and the immobilized βG-binding protein 2 to an insoluble carrier such as latex particle; then (iii) quantity of the aforementioned complex-2 is measured; and (iv) βG concentration in the sample is determined based on the quantity of the aforementioned complex obtained.

Furthermore, a method in which quantity of the βG in a sample is measured by using an antibody against βG-binding protein 1 or βG-binding protein 2 and the βG-binding protein 1 and the βG-binding protein 2, forming a complex of the aforementioned antibody and the βG-binding protein 1 and the βG-binding protein 2 and the βG in the sample, and measuring quantity of the aforementioned complex, is also included. The antibody to be used for this method may be either a monoclonal antibody or a polyclonal antibody, however, it should be one which do not interfere the formation of complex of βG-binding protein 1, βG-binding protein 2 and βG in the sample. In addition, the βG measurement can also be performed by a single measurement system using several types of the aforementioned antibodies. Furthermore, as described above, it goes without saying that the βG-binding protein 1 and the βG-binding protein 2 may be immobilized to an insoluble carrier, or may be labeled with a labeling substance.

In addition, combination of the βG-binding protein 1 and the βG-binding protein 2 used for the measurement method of the present invention may be the same or different from each other.

That is, βG-binding protein 1 and βG-binding protein 2 in a combination may be one type each, or may be multiple types each. Moreover, one type or multiple types of the βG-binding protein 1 and one type or multiple types of the βG-binding protein 2 to be used may be the same or different from each other. More preferable combination includes a combination in which the βG-binding protein 1 is fragment-a or fragment-b and the βG-binding protein 2 is fragment-a or fragment-b.

In addition, for example, in the case where the βG-binding protein 1 which is bound to an insoluble carrier and the free (labeled) βG-binding protein 2 are used, a preferable combination (an immobilized βG-binding protein 1 to an insoluble carrier-free βG-binding protein 2) includes (fragment-a-fragment-a), (fragment-a-fragment-f), (fragment-b-fragment-a), (fragment-b-fragment-d), (fragment-b-fragment-f), (fragment-e-fragment-f) and (fragment-f-fragment-f).

A more preferable combination includes (fragment-a-fragment-a), (fragment-a-fragment-b), (fragment-b-fragment-a), and (fragment-b-fragment-b); and a further preferable combination includes (fragment-a-fragment-a) and (fragment-b-fragment-a). A particularly preferable combination includes (fragment-b-fragment-a).

Next, a method for separating obtained complex-1 or complex-2 from the βG-binding protein 1 and/or the βG-binding protein 2 which did not form a complex includes the methods of separation analysis well known per se and used commonly.

For example, as to a separation method in the case where the measurement using the βG-binding protein involved in the present invention which is immobilized to an insoluble carrier is carried out, a method for separation by the B/F separation technique is included.

In addition, a method for separation in the case where the measurement is carried out using a free (labeled) βG-binding protein 1 and/or a free (labeled) βG-binding protein 2 which are not immobilized to an insoluble carrier includes, for example, chromatography, high performance liquid chromatography, electrophoresis, capillary electrophoresis, capillary chip electrophoresis, and a method using an automated immunological analyzer such as, for example, LiBASys (manufactured by Shimadzu Corp.). Specific conditions thereof may be set so that the obtained complex-1 or the complex-2 can be separated from a free (labeled) βG-binding protein 1 and/or a free (labeled) βG-binding protein 2 which do not form the complex, and other conditions may be in accordance with the methods well known per se. For example, when separation is carried out using HPLC, operation may be carried out according to the method described in Anal. Chem. 65, 5, 613-616 (1993) or JP-A-9-301995; and in the case where capillary electrophoresis is used, it may be performed according to the method described in J. Chromatogr. 593, 253-258 (1992); Anal. Chem. 64, 1926-1932 (1992); and WO2007/027495. In addition, for example, when LiBASys is used as an automated immunological analyzer, operation may be carried out according to the method described in the Journal of Analytical Bio-Science, 22 No. 4 303-308 (1999).

As to the insoluble carrier which is used for immobilizing βG-binding protein involved in the present invention in the method for measuring βG of the present invention, any carrier can be used as long as it is used, for example, in the conventional immunological measurement methods, and, for example, synthetic high polymers such as, for example, a polystyrene, a polypropylene, a polyacrylic acid, a polymethacrylic acid, a polyacrylamide, a polyglycidyl methacrylate, a polyvinyl chloride, a polyethylene, a polychlorocarbonate, a silicone resin, and a silicone rubber, inorganic substances such as, for example, a porous glass, a ground-glass, ceramics, an alumina, a silica gel, an activated charcoal, and a metal oxide are included. In addition, these insoluble carriers can be used in wide variety of forms such as a microtiter plate, a bead, a tube, a dedicated tray with integrally molded many tubes, a disk-like piece, and particulates (latex particles). Among them, a microplate and a bead are preferable particularly from the viewpoints, such as easiness of washing and operability at the time of processing many samples concurrently.

The method for immobilizing the βG-binding protein involved in the present invention to a earner is not particularly limited, as long as the βG-binding protein can be immobilized to an insoluble carrier. All of the immobilization methods usually used in this field and well known per se, for example, a chemical coupling method (immobilization method by covalent bond), a method by physical adsorption, and the like are included.

A preferable example includes, for example, a method for obtaining an insoluble carrier (solid phase) bound with the βG-binding protein by bringing an insoluble carrier in contact with a solution containing the βG-binding protein involved in the present invention in a range of 0.1 μg/mL to 20 mg/mL, and preferably 1 μg/mL to 5 mg/mL, and by reacting at an appropriate temperature for predetermined time.

As to a solvent to be used for preparing a solution of the βG-binding protein, it may be the one which does not have a property of interfering adsorption or binding of the βG-binding protein involved in the present invention to an insoluble carrier, for example, purified water, phosphate buffer solution, Tris buffer solution, Good's buffer solution, glycine buffer solution, borate buffer solution, MOPS buffer solution having buffering action at around neutral pH, for example, pH 5.0 to pH 10.0, preferably pH 6.5 to pH 8.5, and the like are preferable. In addition, concentration of buffering agent in these buffer solutions is selected appropriately from the range of usually 10 mM to 500 mM, and preferably 10 mM to 300 mM. Moreover, this solution may comprises, for example, sugars, salts such as NaCl, surface active agent, preservatives, and the like, as long as the amount thereof does not interfere adsorption or binding of the βG-binding protein involved in the present invention to an insoluble carrier.

It should be noted that it is desirable to carry out a blocking treatment usually performed in this field, that is, a treatment by dipping the insoluble carrier which is bound with the βG-binding protein involved in the present invention obtained as described above into a solution containing a protein unrelated to the βG-binding protein such as, for example, a human serum albumin, a bovine serum albumin, a milk protein such as a skimmed milk, an egg albumin, a commercially available blocking agent (for example, Blockace (produced by Dainippon Sumitomo Pharma Co. Ltd.)), and the like, from the viewpoint of preventing nonspecific reaction during the measurement.

In addition, the above described "βG-binding protein immobilized to an insoluble carrier" may be immobilized directly to an insoluble carrier, or may be immobilized to an insoluble carrier through anti-βG-binding protein antibody which is immobilized to an insoluble carrier. The anti-βG-binding protein antibody to be used therefor may be either a monoclonal antibody or a polyclonal antibody. In addition, a specific example of the insoluble carrier to which the anti-βG-binding protein antibody is immobilized includes the same insoluble carrier as used for immobilization of the above described βG-binding protein. To immobilize the anti-βG-binding protein antibody, immobilization may be carried out according to the above described method for immobilizing βG-binding protein to an insoluble carrier.

It should be noted that it is also possible to immobilize the βG-binding protein to an insoluble carrier by using very firm binding reaction like the avidin-biotin reaction commonly used in this field.

The labeling substance to be used for labeling the βG-binding protein in the present invention includes all of the labeling substances usually used in this field, for example, enzymes used in the usual immunoassay methods such as peroxidase, microperoxidase, alkaline phosphatase, β-galactosidase, glucose oxidase, glucose-6-phosphate dehydrogenase, acetylcholinesterase, malic dehydrogenase, and luciferase, radioactive isotopes as used in the radioimmunoassay (RIA), for example, $^{99m}Tc$, $^{131}I$, $^{125}I$, $^{14}C$, $^{3}H$, $^{32}P$ and $^{35}S$, fluorescent substances as used in the fluoroimmunoassay (FIA), for example, fluorescein, dansyl, fluorescamine, coumarin, naphthylamine fluorescein isothiocyanate (FITC), rhodamine, rhodamine X isothiocyanate, sulforhodamine 101, lucifer yellow, acridine, acridine isothiocyanate, riboflavine, or derivatives thereof, luminescent substances such as luciferin, isoluminol, luminol, and a bis(2,4, 6-trifluorophenyl)oxalate, a substance having absorption in ultraviolet region, such as phenol, naphthol, anthracene, or the derivatives thereof, a substance having a property as a spin-labeling agent represented by the compound having an oxyl group, for example, 4-amino-2,2,6,6-tetramethylpiperidine-1-oxyl, 3-amino-2,2,5,5-tetramethylpyrmlidine-1-oxyl, and 2,6-di-t-butyl-α-(3,5-di-t-butyl-4-oxo-2,5-cyclohexadiene-1-yiliden)-p-toryloxyl.

Moreover, in addition to the labeling substance mentioned above, for example, HiLyte series dye such as HiLyte Fluor 647, HiLyte Fluor 488, HiLyte Fluor 555, HiLyte Fluor 680, and HiLyte Fluor 750 (all of them are trade names of HiLyte Bioscience, Inc.), Alexa series dye such as Alexa Fluor Dye 350, Alexa Fluor Dye 430, Alexa Fluor Dye 488, Alexa Fluor Dye 532, Alexa Fluor Dye 546, Alexa Fluor Dye 555, Alexa Fluor Dye 568, Alexa Fluor Dye 594, Alexa Fluor Dye 633, Alexa Fluor Dye 647, Alexa Fluor Dye 660, Alexa Fluor Dye 680, Alexa Fluor Dye 700, and Alexa Fluor Dye 750 (all of them are trade names of Molecular Probes, Inc.), CyDye series dye such as Cy3, Cy3.5, Cy5, Cy5.5, and Cy7 (all of them are trade names of Amersham Biosciences Corp.), and for example, the dye such as Coomassie Brilliant Blue R250, and methyl orange can be also used.

In addition, in order to bind the above described labeling substance (labeling) to the βG-binding protein, for example, the labeling method well known per se which is used commonly in the immunoassay method (EIA, RIA, FIA) well known per se (for example the method described in "Course on Experimental Medical Chemistry", vol. 8, supervised by Yuichi Yamamura, the 1st edition, Nakayama Shoten, 1971; "Illustrative Description of Fluorescent Antibody", Akira Kawaoi, the 1st edition, Soft Science Inc., 1983; "Enzyme Immunoassay", Eiji Ishikawa, Tadashi Kawai, Kiyoshi Muroi ed, the 2nd edition, Igaku Shoin Ltd., 1982; "Molecular Cloning A Laboratory Manual Second Edition", J. Sambrook, E. F. Frisch, T. Maniatis, Cold Spring Harbor Laboratory Press), or a conventional procedure utilizing reaction of avidin (streptavidin) and biotin, or the like may be carried out appropriately.

Furthermore, the βG-binding protein may be labeled by a method in which a labeling substance is bound to the βG-binding protein through one or several amino acids, or one or several amino acids and linkers. The βG-binding protein which is bound to the labeling substance through amino acid or amino acid and linker makes a distance between βG-binding site and labeling substance in the βG-binding protein longer. By this reason, since a possibility to interfere binding of a βG in a sample to the βG-binding site by the labeling substance becomes low, this labeling method is more preferable. To obtain the βG-binding protein bound with amino acid, the amino acid may be bound to N-terminal of βG involved in the present invention by the conventional procedure. In addition, the βG-binding protein which was bound with the amino acid can also be obtained by carrying out the PCR using F primer which is added with a nucleotide sequence encoding the aforementioned amino acid on N-terminal, the obtained PCR product is incorporated in a suitable expression vector DNA and followed by obtaining a transformant by the routine procedures, then the βG-binding protein of the present invention is expressed.

Moreover, since various types of kit for binding (labeling) the labeling substance as described above to protein is also available in the market, the labeling may be carried out using them according to instruction manual attached to the kit.

Furthermore, the above described "labeled βG-binding protein which is labeled with a labeling substance" may be the one which is labeled indirectly by binding a labeled anti-βG-binding protein antibody which is labeled with a labeling substance. The anti-βG-binding protein antibody to be used therefor may be either a monoclonal antibody or a polyclonal antibody. Moreover, a specific example of the labeling substance for labeling anti-βG-binding protein antibody and a method for measuring the aforementioned label, are as mentioned in the description regarding the labeled βG-binding protein. Furthermore, to label the anti-βG-binding protein antibody with the aforementioned labeling substance, the labeling may be performed according to the above described method for labeling βG-binding protein with a labeling substance.

Moreover, a nucleic acid chain can also be used as a labeling substance.

A nucleic acid chain is a polynucleotide, which comprises nucleotide residue as a basic unit consisted of a purine base or a pyrimidine base, a sugar moiety of pentose and phosphoric acid, and this phosphoric acid connects each nucleotide through diester bond between 3' carbon of the sugar moiety of one nucleotide and 5' carbon of sugar moiety of another nucleotides and polymerized, and for example, RNA whose sugar portion is ribose or/and DNA whose sugar portion is deoxyribose are included. In addition, the aforementioned nucleic acid chain may be the one which consists of single chain, double or more of multiple nucleic acid chain.

Length of the nucleic acid chain to be used may be the one which can attain the purpose of the present invention, and it is normally 1 bp to 1000 kbp, preferably 5 bp to 100 kbp, and more preferably 10 bp to 50 kbp.

It should be noted that the nucleic acid chain used in the present invention may be optionally modified by an appropriate substance, within a range where the purpose of the present invention can be attained.

The method for binding the βG-binding protein involved in the present invention to the nucleic acid chain includes, for example, a known method disclosed in JP-B-4214779.

For example, the respective functional groups possessed by the βG-binding protein involved in the present invention and a nucleic acid chain may be bonded directly or through a linker [for example, N-(ε-maleimidecaproyloxy)succinimide (EMCS), Sulfosuccinimidyl 4-(p-maleimidophenyl)butyrate (Sulfo-SMPB), Sulfosuccinimidyl 4-(N-maleimidomethyl)-cyclohexane-1-carboxylate (Sulfo-SMCC), and the like], and the like.

Moreover, after introducing reactive functional group into a nucleic acid chain in advance, the βG-binding protein involved in the present invention and the nucleic acid chain where a reactive functional group is introduced may be bound together according to the method described in JP-B-4214779. The method for introducing a reactive functional group to the nucleic acid chain includes the method well known per se.

In addition, as to the method for binding βG-binding protein involved in the present invention to the nucleic acid chain, the reactive functional group can be introduced into the 5'-terminal of nucleic acid, for example, by a method of obtaining nucleic acid chain as a PCR product where a reactive functional group is introduced into the 5'-terminal by carrying out the PCR using a PCR primer where a reactive functional group is introduced into the 5'-terminal ("Molecular Cloning A Laboratory Manual Second Edition", J. Sambrook, E. F. Frisch, T. Maniatis, Cold Spring Harbor Laboratory Press, etc.).

In addition, the above described "labeled MG-binding protein which is labeled with a labeling substance" may be the one which binds a labeled nucleic acid chain labeled with the labeling substance. A nucleic acid to be used therefor and a method for binding the nucleic acid to the βG-binding protein is as described above.

The method for binding nucleic acid to a labeling substance includes, for example, a method described in JP-B-4214779.

It should be noted that the solution containing βG-binding protein which is labeled with a labeling substance (labeled βG-binding protein) may comprise one which is usually used as a stabilizer in this field, for example, a sugar, a protein, a surface active agent, and the like at a concentration within a range which is usually used in this field.

Moreover, a method for measuring an amount of labeling in the complex produced as a result of practicing the measurement method of the present invention may vary depending on kinds of labeling substances used, however, the method may be carried out according to the prescribed procedures each corresponding to a property possessed by the labeling substance which can be detected by some sort of method. For example, in the case where the labeling substance is enzyme, the measurement may be carried out according to the conventional immunoassay method, for example, the method described in "Enzyme Immunoassay Method" (PROTEIN, NUCLEIC ACID AND ENZYME, Separate vol. No. 31, Tsunehiro Kitagawa, Toshio Nanbara, Akio Tsuji, and Eiji Ishikawa ed., pp. 51-63, Kyoritsu Shuppan Co., Ltd., 1987), and in the case where the labeling substance is a radioactive substance, the measurement can be performed, for example, according to a routine procedure which is currently carried out in RIA, and using by appropriately selecting and using a measurement apparatus such as an immersion GM counter, a liquid scintillation counter, a well-type scintillation counter, and a counter for HPLC, depending on the kind and intensity of radiation generated by the radioactive substance (see for example, "Course on Experimental Medical Chemistry", vol. 8, Yuichi Yamamura editorial supervision, the 1st edition, Nakayama Shoten, 1971). In addition, in the case where the labeling substance is a fluorescent substance, the measurement may be carried out according to the routine procedure performed in FIA using a measurement apparatus such as a fluorescence spectrophotometer, for example according to the method described in "Illustrative Description of Fluorescent Antibody", Akira Kawaoi, the 1st edition, Soft Science Inc., 1983; and in the case where the labeling substance is a luminescent substance, the measurement may be carried out according to the routine procedure using a measurement apparatus such as a photo counter, for example, according to the method described in "Enzyme Immunoassay Method" (PROTEIN, NUCLEIC ACID AND ENZYME, Separate vol. No. 31, Tsunehiro Kitagawa, Toshio Nanbara, Akio Tsuji, and Eiji Ishikawa ed., pp. 252-263, Kyoritsu Shuppan Co., Ltd., 1987). Furthermore, in the case where the labeling substance is a substance which has absorption in the ultraviolet region, the measurement may be carried out by a routine procedure using a measurement apparatus such as a spectrophotometer; and in the case where the labeling substance has a character of spin, the measurement may be carried out by the routine procedure using electron spin resonance equipment, for example, according to a method described in "Enzyme Immunoassay Method" (PROTEIN, NUCLEIC ACID AND ENZYME, Separate vol. No. 31, Tsunehiro Kitagawa, Toshio Nanbara, Akio Tsuji, and Eiji Ishikawa ed., pp. 264-271, Kyoritsu Shuppan Co., Ltd., 1987).

More specifically, for example, in the case where the labeling substance is enzyme, the methods well known per se such as a method where the labeling substance is reacted with a coloring reagent to lead to chromogenic reaction, and intensity of the color generated as a result is measured by a spectrophotometer, or the like, are included.

The coloring reagent used for such purpose includes the coloring reagents usually used in this field, for example, tetramethylbenzidine (TMB), o-phenylenediamine, o-nitrophenyl-β-D-galactoside, 2,2'-azino-bis(3-ethylbenzothiazoline-6-sulfonic acid) (ABTS), N-ethyl-N-sulfopropyl-m-anisidine (ADPS) and p-nitrophenylphosphate, etc. In addition, concentrations of these coloring reagents to be used may be set appropriately from the range of concentration usually used in this field.

In addition, in order to terminate the chromogenic reaction, the method for terminating reaction usually carried out in this field, for example, addition of enzyme inhibitor such as 1 N to 6 N sulfuric acid, or a reaction terminating agent attached to the kit to the reaction solution may be utilized In addition, a method for measuring βG using unlabeled βG-binding protein includes, for example, a measurement method utilizing a property derived from a complex obtained, specifically, a method for measuring enzyme activity such as protease activity or a degree of fluorescent deflection possessed by a complex itself as absorbance, or else a homogeneous immunoassay system such as surface plasmon resonance, and the like.

Moreover, the carrier such as latex particle to be used for the method where immobilized βG-binding protein 1 to an insoluble carrier such as latex particle and immobilized βG-binding protein 2 to an insoluble carrier such as latex particle are used includes, for example, the one which is used in the immunoassay method, for example, the one which is prepared using assembly of molecule such as liposome, and polymer micelle; synthetic polymer compound such as polystyrene, polyacrylic acid, polymethacrylic acid, polyacrylamide, polyglycidyl methacrylate, polypropylene, polyvinyl chloride, polyethylene, polychlorocarbonate, silicone resin, and silicone rubber; inorganic substance such as porous glass, ground-glass, alumina, silica gel, activated charcoal, and metal oxide; and the like as a material. Moreover, among them, the latex particle is particularly preferable from the viewpoints that it is easy to carry out chemical treatment of the carrier surface depending on the purpose and non-specific reaction does not occur easily, because it is artificial carrier. Although a material thereof is not particularly limited, but styrene-based latex particle such as polystyrene latex particle and acrylic-acid-based latex particle and the like are included as a preferable one.

Form thereof includes the one having a form of bead, microparticle, and latex particle. In addition, particle size is not particularly limited, however, the one which has mean particle size of usually 0.05 μm to 0.5 μm, and preferably 0.1 μm to 0.4 μm is preferable.

The method for supporting the βG-binding protein involved in the present invention by the above described carrier is not particularly limited, as long as the βG-binding protein is brought into contact with the carrier. The supporting method includes the one well known per se and usually used in this field (for example, so-called physical adsorption method) as a representative example.

Moreover, in the case where the commercially available carrier is used, the βG-binding protein involved in the present invention may be supported to the carrier according to the supporting method recommended by the instruction manual attached.

In the method which uses immobilized βG-binding protein 1 to an insoluble carrier such as latex particle and immobilized βG-binding protein 2 to an insoluble carrier such as latex particle, a method for measuring quantity of complex formed by immobilized βG-binding protein 1 to an insoluble carrier such as latex particle, βG in a sample and immobilized βG-binding protein 2 to an insoluble carrier such as latex particle includes routine methods such as, for example, so-called turbidimetric method where determination of objective component is carried out by measuring change in turbidity caused by generation of the aforementioned complex, so-called nephelometry where determination of objective component is carried out by measuring change of scattered light intensity, and the latex aggregation method and so on.

To obtain the βG concentration in a sample by the above described methods, a standard curve which shows relationship between βG concentration and change of turbidity or scattered light intensity obtained in advance by performing same operation using the samples of known βG concentrations is prepared, and by fitting the measurement value to the standard curve, βG concentration in a sample can be determined In the method for measuring βG of the present invention, concentrations of βG-binding protein 1 and MG-binding protein 2 involved in the present invention at each reaction varies depending on how wide range to be measured for βG, or on the specific measurement method.

For example, in the case where 0.1 pg to 1 μg of βG is measured and the measurement using two molecules of free βG-binding protein is carried out, amounts of the free βG-binding protein 1 and the free βG-binding protein 2 to be used are each 0.1 ng to 0.1 mg, respectively.

In the case where the measurement is carried out using an immobilized βG-binding protein 1 to an insoluble carrier and the labeled βG-binding protein 2, and by chemiluminescence method or chromogenic method, amount of the immobilized βG-binding protein 1 to an insoluble carrier to be used is about 0.1 ng to 0.1 mg, and amount of the labeled βG-binding protein 2 to be used is about 0.1 ng to 0.1 mg.

In addition, for example, in the case where 0.1 pg to 1 μg of βG is measured and measurement using two molecules of the immobilized βG-binding protein to an insoluble carrier is carried out, amount of the βG-binding protein 1 and the βG-binding protein 2 to be used are each about 0.1 ng to 0.1 mg, respectively.

When a sample containing βG and the free βG-binding protein are reacted, amount of the βG-binding protein involved in the present invention to be used is normally 1 μL to 1000 μL (containing 0.1 ng to 0.1 mg as βG-binding protein), preferably 2 μL to 500 μL, to the sample containing βG 1 μL to 1000 μL, preferably 10 μL to 100 μL (containing 0.1 pg to 1 μg of βG).

In addition, temperature during the reaction is 25° C. to 40° C., and preferably 30° C. to 37° C., and reaction time is usually for 10 seconds to 30 hours, preferably 5 minutes to 20 hours, and more preferably it is 30 minutes to 10 hours.

The βG-binding protein 1 and the βG-binding protein 2 may be reacted with a sample simultaneously or sequentially.

As a specific example of the method for measuring βG concentration of the present invention, a method for measuring βG concentration in a sample derived from biological body using peroxides (POD) as a labeling substance, and an immobilized βG-binding protein 1 to an insoluble carrier and a POD-labeled βG-binding protein 2 is explained as follows.

That is, a 50 μL, of sample containing βG (0.1 pg to 1 μg of βG is contained) is brought into contact with a solid phase where the βG-binding protein 1 involved in the present invention is immobilized to an insoluble carrier (containing 0.1 ng to 0.1 mg of βG-binding protein 1), and reacted at 4° C. to 40° C. for 3 minutes to 20 hours to form a complex of the βG and the βG-binding protein 1 (referred to as complex-1) on the insoluble carrier. Subsequently, the complex-1 is reacted with 50 μL to 100 μL of a solution (containing 0.1 ng to 0.1 mg of βG-binding protein 2) containing POD-labeled βG-binding protein 2 involved in the present invention at 4° C. to 40° C. for 3 minutes to 16 hours to form a complex of immobilized βG-binding protein 1-βG-labeled βG-binding protein (referred to as complex-2) on the insoluble carrier. Then, after adding, for example, TMB solution of an appropriate concentration, the complex-2 is reacted for predetermined time. After that, the reaction is terminated by adding reaction terminating solution such as 1 M phosphoric acid. Absorbance at 450 nm is measured. The βG concentration in the sample can be determined by fitting the measurement value obtained to a standard curve which is obtained in advance by carrying out the same operation for the samples of known βG concentrations using the same reagents, and shows a relationship between the measurement value and βG concentration.

When βG is detected by carrying out capillary chip electrophoresis, the detection may be performed by an instrument such as differential refractive detector, fluorescence detector, and UV detector, and the UV detector and the fluorescence detector are preferable among them, and the fluorescence detector is more preferable.

In the case where the method for measuring βG of the present invention is carried out, for example, by separating by the capillary chip electrophoresis and measuring by the fluorescence detector, the measurement may be carried out as follows. The βG-binding protein 1 and the βG-binding protein 2 which to be used may be labeled with a labeling substance.

That is, 1 μL to 50 μL of βG sample is mixed with a 20 to 50 μl of a reagent solution containing, usually 0.001 μM to 10

μM, and preferably 0.01 μM to 1 μM of the βG-binding protein 1 involved in the present invention and usually 0.01 μM to 10 μM, and preferably 0.01 μM to 1 μM of the βG-binding protein 2 involved in the present invention, and reacted under warming 25° C. to 40° C. for 5 minutes to 30 minutes, and preferably for 10 seconds to 15 minutes. After that, the obtained solution is separated by an appropriate separation method, for example, by capillary chip electrophoresis, and measured, for example, by a fluorescence detector and the like. The βG concentration in the sample can be determined by fitting the measurement value obtained to a standard curve which is obtained in advance using solutions of known βG concentrations, and shows a relationship between the βG concentration and the aforementioned measurement value.

It should be noted that the measurement of βG can also be carried out using, for example, the βG-binding protein 1 which is labeled with Alexa Fluor-488 tetrafluorophenyl ester or the like and, for example, the βG-binding protein 2 which is labeled with Alexa Fluor-647 succinimidyl ester or the like, and by carrying out so-called well-known fluorescence correlation spectroscopy (FCCS).

The sample involved in the present invention includes a clinical sample such as, for example, blood, serum, plasma, urine, lymph, cerebrospinal fluid, pleural effusion, and ascites fluid; medical drug; medical device; food; and the like, however, the sample is not limited thereto.

A specific example of buffer solution for dissolving the βG-binding protein to be used in the measurement method of the present invention includes all of buffer solutions usually used for the measurement method using antigen-antibody reaction such as a Tris buffer solution, a phosphate buffer solution, a veronal buffer solution, a borate buffer solution, a Good's buffer solution, and the like, and pH thereof is not particularly limited, so long as it is in a range where the reaction of protein of the present invention and βG is not inhibited, but usually a range of pH 5 to pH 9 is preferable.

It should be noted that the present invention can be sufficiently utilized not only in manual operation but also in a measurement system using automated analyzer, and can perform the measurement easily and rapidly. Moreover, when measurement is carried out in manual operation or using an automated analyzer, combination of reagents and the like is not particularly limited, and the best combination of reagents and the like in accordance with a circumstance and a model of automated analyzer to be applied, or taking other factors into consideration may be selected and used.

The reagent for measuring βG of the present invention includes "a reagent for measuring βG containing a protein comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having the β-glucan binding activity". The βG-binding protein may be immobilized to an insoluble carrier.

In addition, the βG-binding protein may be labeled with a labeling substance. Preferable aspects and the like of the insoluble carrier and the labeling substance are as described above. Moreover, the above described insoluble carrier to which the βG-binding protein is immobilized may be either of the insoluble carrier to which only one kind of βG-binding protein is immobilized or the insoluble carrier to which plural kinds of βG-binding proteins have been immobilized.

Concentration of the βG-binding protein contained in the reagent of the present invention is usually 0.1 ng/mL to 100 mg/mL, and preferably 1 ng/mL to 10 mg/mL.

Moreover, in the reagent of the present invention, other appropriate reagents usually used in this field such as a buffering agent and an alkaline earth metal salt may be further contained, and these reagents may be selected appropriately from those used in the so-called biochemical reactions and the like and used. Specifically, the above described buffering agent includes buffer solution usually used in this field such as a Trishydroxylaminomethan buffer solution, a phosphate buffer solution, a borate buffer buffer solution, a Good's buffer solution, and the like, and concentration of the aforementioned buffering agent in the reagent may vary somewhat depending on the reagent to be used, but usually it is 5 mM to 500 mM, and preferably 20 mM to 200 mM. It should be noted that the βG-binding protein involved in the present invention may be a freeze-dried material.

The kit for measuring βG of the present invention includes the one consisting of the followings as a constituent:

(1) a reagent comprising protein 1 comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having the β-glucan binding activity (βG-binding protein 1), and (2) a reagent comprising protein 2 comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, SEQ ID NO: 16, SEQ ID NO: 18, or SEQ ID NO: 20, and having the β-glucan binding activity (βG-binding protein 2).

The βG-binding protein may be supported by an insoluble carrier. In addition, the βG-binding protein may be labeled with a labeling substance.

Preferable aspect and specific example of the constituents are as described above.

Moreover, the βG-binding protein 1 and the βG-binding protein 2 which constitute the above (1) and (2) of the aforementioned kit, respectively, may be each the one of one type or the one of two or more types. In addition, the βG-binding protein 1 which constitutes (1) and the βG-binding protein 2 which constitutes (2) may be the same or different from each other.

Moreover, the kit for measuring βG of the present invention may be, if necessary, added with a reagent usually used in this field such as sugar alcohols like mannitol and sorbitol, saccharoses like sucrose and trehalose, polysaccharides like dextran, proteins like bovine serum albumin, stabilizing agents such as surface active agent, and concentrations thereof and the like may be set within the range usually used in this field. In addition, in the reagent containing the βG-binding protein of the present invention, buffering agent, alkali earth metal salt, and the like which are described in the section of the reagent of the present invention may be uses, and concentration thereof and the like may be used within the same range as described above. Further, the kit may comprise standard βG to prepare a standard curve in combination. As for the aforementioned standard βG, either of a commercially available standard preparation of βG manufactured by Wako Pure Chemical Industries, Ltd. or the one manufactured according to the method described in JP-B-3652738 may be used. Moreover, these reagents in the reagent kit may be a freeze-dried material.

The βG-binding protein of the present invention is the factor G-subunit α which is capable of binding to βG in the hemocyte component of horseshoe crab and a fragment derived from the aforementioned subunit α, and hence a protein which has the β-glucan binding activity.

For example, a protein which is the factor G-subunit α of the hemocyte component of horseshoe crab (*Limulus polyphemus*) and a fragment thereof, and has the β-glucan binding activity, and a protein which is the factor G-subunit α of the hemocyte component of horseshoe crab (*Tachypleus tridentatus*) and a fragment thereof, and has the β-glucan binding activity.

An example of such βG-binding protein of the present invention includes "a protein comprising an amino acid sequence identical or substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having the β-glucan binding activity".

In the βG-binding protein of the present invention, "a protein having an amino acid sequence identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having βG binding activity" corresponds to each fragment of the factor G-subunit α of horseshoe crab (*Limulus polyphemus*), or each fragment of the factor G-subunit α of horseshoe crab (*Tachypleus tridentatus*), explained in the above described "method for measuring βG".

In addition, an "amino acid sequence substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20" includes an amino acid sequence which has about 70% or more, preferably about 80% or more, more preferably about 90% or more, further preferably about 95% or more of homology to an amino acid sequence shown in any one of SEQ ID NO: 4, SEQ ID NO: 6, SEQ ID NO: 8, SEQ ID NO: 10, SEQ ID NO: 14, or SEQ ID NO: 20.

In addition, "a protein having an amino acid sequence substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20" includes, for example, a protein having an amino acid sequence substantially identical to an amino acid sequence shown in any one of SEQ ID NO: 4, SEQ ID NO: 6, SEQ ID NO: 8, SEQ ID NO: 10, SEQ ID NO: 14, or SEQ ID NO: 20, and having βG binding activity.

In more specifically, for example, it is a protein or the like having an amino acid sequence shown in SEQ ID NO: 4, SEQ ID NO: 6, SEQ ID NO: 8, SEQ ID NO: 10, SEQ ID NO: 14, or SEQ ID NO: 20, in which 1 to 5 (preferably, 1 to 3) amino acids are replaced or deleted, or 1 to 5 (preferably, 1 to 3) amino acids are inserted or added, and having βG binding activity.

Replacement, deletion, insertion, and addition may take place in two or more sites in one amino acid sequence, as long as the βG-binding activity of this protein is not lost.

The βG-binding protein of the present invention can be produced by a general chemical production process according to the amino acid sequence. The βG-binding protein of the present invention can be obtained by a conventional chemical synthetic method such as, for example, fluorenylmethyloxycarbonyl method (Fmoc method) and t-butyloxycarbonyl method (tBoc method). In addition, it can also be obtained by chemical synthesis using a commercially available peptide synthesizer.

Furthermore, the βG-binding protein of the present invention can also be obtained by the well known method using gene-recombination technology, where a nucleic acid molecule which encodes the βG-binding protein of the present invention is incorporated into an appropriate expression vector such as plasmid and phage; host cell is transformed (or transduced) using this recombinant expression vector; the obtained host cell is cultured to secrete the βG-binding protein of the present invention intracellularly or extracellularly.

The nucleic acid molecule encoding the βG-binding protein of the present invention is "a nucleic acid molecule comprising a nucleotide sequence identical or substantially identical to a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19.

"A nucleic acid molecule comprising a nucleotide sequence identical to a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19" encoding βG-binding protein of the present invention includes "a nucleic acid molecule consisting of a nucleotide sequence identical to a nucleotide sequence shown in any one of SEQ ID NO: 1, SEQ ID NO: 3, SEQ ID NO: 5, SEQ ID NO: 7, SEQ ID NO: 9, or SEQ ID NO: 13" and "a nucleic acid molecule comprising an entire nucleotide sequence identical to a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19".

"A nucleic acid molecule comprising a nucleotide sequence substantially identical to a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19" includes a nucleic acid molecule having a nucleotide sequence shown in any one of SEQ ID NO: 1, SEQ ID NO: 3, SEQ ID NO: 5, SEQ ID NO: 7, SEQ ID NO: 9, SEQ ID NO: 13, or SEQ ID NO: 19, in which 1 to several nucleotides are partially deleted, added, replaced, or inserted. The deletion, addition, replacement, or insertion may take place in one site or two or more sites of one nucleic acid molecule simultaneously.

In addition, the nucleic acid molecule encoding the βG-binding protein of the present invention also includes "a nucleic acid molecule encoding a protein comprising an amino acid sequence identical or substantially identical to an amino acid sequence shown in any one of SEQ ID NO:2, SEQ ID NO: 4, SEQ ID NO: 6, SEQ ID NO: 8, SEQ ID NO: 10, SEQ ID NO: 14, or SEQ ID NO: 20, and having βG binding activity (the βG-binding protein of the present invention)". Specific example of "the βG-binding protein of the present invention" mentioned here is as described in the above explanation on "the βG-binding protein involved in the present invention".

The nucleic acid molecule may be either DNA or RNA.

An example of a method for preparing the βG-binding protein involved in the present invention (including the βG-binding protein of the present invention) by a genetic method is explained below.

1. Preparation of Recombinant Vector for Expression (1) Preparation of cDNA

Total RNA is extracted from the hemocyte of horseshoe crabs (*Limulus polyphemus*) by a conventional method, and purified mRNA is obtained by utilizing a conventional method such as, for example, extraction with a poly (A) chain possessed by the mRNA. Using the obtained purified mRNA as a template, cDNA is synthesized by a routine procedure of reverse transcription reaction. This cDNA is used as a template in the case of following PCR as a cDNA library containing horseshoe crab factor G-subunit α gene.

(2) Preparation of Recombinant Expression Vector Incorporating a Nucleotide Sequence For the βG-Binding Protein Involved in the Present Invention 1) Preparation of Recombinant Expression Vector Incorporating a Sequence Comprising Horseshoe Crab Factor G-Subunit α Gene For example, by a routine procedures, an objective DNA fragment of the sequence comprising horseshoe crab factor G-subunit α gene (for example, SEQ ID NO:1 or SEQ ID NO:11) is amplified by a nucleic acid amplification method such as PCR using a reverse primer (R primer) designed from an arbitrary position selected from 3'-terminal region of the nucleotide sequence of cDNA (SEQ ID NO:1 or SEQ ID NO:11) which encodes horseshoe crab factor G-subunit α, and a forward primer (F primer) designed from an arbitrary position from 5'-terminal region to initiation codon of SEQ ID NO:1 or SEQ ID NO:11, and using a cDNA library comprising horseshoe crab factor G-subunit α gene (the above described cDNA library and the like) as a template. The PCR product obtained is incorporated in an appropriate vector DNA for expression according to a routine procedure to obtain a recombinant expression vector.

If need arises, the nucleotide sequence of the DNA fragment integrated into the recombinant expression vector is analyzed to confirm that the sequence comprising the objective horseshoe crab factor G-subunit α gene has surely been incorporated.

2) Preparation of Recombinant Expression Vector Incorporating a Sequence Comprising Gene for a Fragment Derived from Horseshoe Crab Factor G-Subunit α (1)

First, for example, by a routine procedures, a DNA fragment of the sequence comprising horseshoe crab factor G-subunit α gene (for example, SEQ ID NO: 1 or SEQ ID NO: 11) is amplified by a nucleic acid amplification method such as PCR, using R primer designed from an arbitrary position selected from 3'-terminal region of the nucleotide sequence of cDNA (SEQ ID NO: 1 or SEQ ID NO: 11) which encodes horseshoe crab factor G-subunit α, F primer designed from an arbitrary position from 5'-terminal region to initiation codon of SEQ ID NO: 1 or SEQ ID NO: 11, and a cDNA library comprising horseshoe crab factor G-subunit α gene (cDNA and the like) as a template. The PCR product obtained is incorporated in an appropriate vector DNA for expression according to a routine procedure to obtain a recombinant vector.

A vector to be used here includes, for example, a cloning vector such as TA cloning vector. The procedure is simple and easy if commercially available cloning vector is used. For example, pGEM-T Easy (produced by Progema Corp.) and the like are used widely.

If need arises, the nucleotide sequence of the DNA fragment integrated into the recombinant vector is analyzed, to confirm that the sequence comprising a gene derived from the horseshoe crab factor G-subunit α has surely been incorporated.

Subsequently, a DNA fragment of the sequence comprising a gene for a fragment of the objective horseshoe crab factor G-subunit α (for example, SEC ID NO: 3, SEC ID NO: 5, SEC ID NO: 7, SEC ID NO: 9, SEC ID NO: 13, SEC ID NO: 15, SEC ID NO: 17, SEC ID NO: 19) or a sequence containing the gene for the fragment thereof is amplified by a nucleic acid amplification method such as PCR, using R primer designed from an arbitrary position selected from 3'-terminal region of the nucleotide sequence of cDNA (SEC ID NO: 3, SEC ID NO: 5, SEC ID NO: 7, SEC ID NO: 9, SEC ID NO: 13, SEC ID NO: 15, SEC ID NO: 17, SEC ID NO: 19) which encodes a fragment derived from horseshoe crab factor G-subunit α, F primer designed from an arbitrary position from 5'-terminal region to initiation codon of the same sequence, and a cDNA library comprising the fragment derived from horseshoe crab factor G-subunit α gene (cDNA, the above-obtained recombinant vector incorporating a sequence comprising horseshoe crab factor G-subunit α gene, and the like) as a template. The PCR product obtained is incorporated in an appropriate vector DNA for expression according to a routine procedure to obtain a recombinant expression vector incorporating a sequence comprising the objective gene for a fragment derived from horseshoe crab factor G-subunit α.

If need arises, the nucleotide sequence of the DNA fragment integrated into the recombinant expression vector is analyzed, to confirm if a sequence comprising the objective gene for a fragment derived from the horseshoe crab factor G-subunit α has surely been incorporated.

3) Preparation of Recombinant Expression Vector Incorporating a Sequence Comprising a Gene for a Fragment Derived from Horseshoe Crab Factor G-Subunit α (2)

For example, by a routine procedures, a DNA fragment of the sequence comprising an objective gene for a fragment derived from horseshoe crab factor G-subunit α (SEC ID NO: 3, SEC ID NO: 5, SEC ID NO: 7, SEC ID NO: 9, SEC ID NO: 13, SEC ID NO: 15, SEC ID NO: 17, SEC ID NO: 19) is amplified by a nucleic acid amplification method such as PCR, using R primer designed from an arbitrary position selected from 3'-terminal region of the nucleotide sequence of cDNA (SEC ID NO: 3, SEC ID NO: 5, SEC ID NO: 7, SEC ID NO: 9, SEC ID NO: 13, SEC ID NO: 15, SEC ID NO: 17, SEC ID NO: 19) which encodes a fragment derived from horseshoe crab factor G-subunit α, F primer designed from an arbitrary position from 5'-terminal region to initiation codon of the same sequence, and a cDNA library comprising a gene for a fragment derived from horseshoe crab factor G-subunit α (cDNA and the like) as a template. The PCR product obtained is incorporated in an appropriate vector DNA for expression according to a routine procedure to obtain a recombinant expression vector incorporating a sequence comprising the objective gene for a fragment derived from horseshoe crab factor G-subunit α.

If need arises, the nucleotide sequence of the DNA fragment integrated into the recombinant expression vector is analyzed, to confirm if a sequence comprising the objective gene for a fragment or a sequence containing the fragment thereof derived from the horseshoe crab factor G-subunit α has surely been incorporated.

It should be noted that the DNA fragment which is incorporated in a recombinant vector for expression (including a nucleotide sequence for the horseshoe crab factor G-subunit α or fragment thereof) can be used as it is for a given purpose, or used after digestion with restriction enzyme or after addition of linker, and so on, if desired.

The expression vector to be used in the method of the above 1) to 3) is not particularly limited, as long as it expresses the βG-binding protein involved in the present invention in various species of prokaryotic and/or eukaryotic host cells and has a function of producing these proteins. For example, plasmid vector, phage vector, and virus vector are included.

Specifically, for example, plasmid vectors such as pTrcHis2 vector, pcDNA3.1/myc-His vector (produced by Invitrogen Corp.), pUC119 (produced by TAKARA SHUZO Co., Ltd.), pBR322 (produced by TAKARA SHUZO Co., Ltd.), pBluescript II KS+ (produced by Stratagene Corp.), Pqe-tri (produced by Qiagen Corp.), pET, pGEM-3Z, pGEX, and pMAL, bacteriophage vectors such as λ ENBL3 (produced by Stratagene Corp.), and λ DASHII (produced by Funakoshi Co., Ltd.), cosmid vectors such as Charomid DNA (produced by Wako Pure Chemical Industries, Ltd.), and Lorist6 (produced by Wako Pure Chemical Industries, Ltd.) are included.

In addition, besides plasmid derived from *E. coli* (for example, pTrc99A, pKK223, pET3a), plasmid derived from Bacillus subtilis (for example, pUB110, pTP5, pC194), plasmid derived from yeast (for example, pSH19, pSH15), bacteriophage such as λ phage, animal viruses such as retrovirus, vaccinia virus, and baculovirus, pA1-11, pXT1, pRc/CMV, pRc/RSV, pcDNA I/Neo, p3×FLAG-CMV-14, pCAT3, pcDNA3.1, pCMV, and the like are included.

It should be noted that in order to make detection and purification easy, the objective βG-binding protein involved in the present invention (horseshoe crab factor G-subunit α or a fragment thereof) may be expressed as a fusion protein with other tag peptide or protein. The tag peptide to be fused includes FLAG tag, 3×FLAG tag, His tag (His tag, for example, 6×His tag), and the like; and the protein includes β-galactosidase (β-Gal), green fluorescent protein (GFP), maltose binding protein (MBP), and the like.

In practice, the βG-binding protein involved in the present invention is expressed as a fusion protein with these peptides or proteins, by carrying out subcloning of the PCR product resulted from PCR reaction using a primer designed to have a sequence which encodes the tag peptide as described above in the front or the rear of an open reading frame; or by inserting a linker having a sequence which encodes the tag peptide between the aforementioned gene and an expression vector; or by using an expression vector comprising a sequence which encodes the tag peptide or protein in advance. For example, using pTrcHis 2 vector (produced by Invitrogen Corp.) incorporating His tag gene as an expression vector, and if a sequence which comprises a gene for βG-binding protein has been incorporated in the upstream of the His tag gene, expression of the gene for βG-binding protein in the upstream region can be also confirmed by confirming the expression of this His tag.

The recombinant construct of the present invention means a recombinant in which the nucleic acid molecule of the present invention as described above is incorporated, and a recombinant vector for expression in which the gene for βG-binding protein involved in the present invention is incorporated is included. The specific example is the same as described above.

2. Preparation of Transformant

The transformant (transductant) of the present invention can be prepared by carrying out transformation (transduction) of an appropriate host cell using the obtained recombinant vector for expression.

A host cell to be used for this purpose includes for example, microorganism [bacteria (for example, Escherichia species and Bacillus species), yeast (for example, Saccharomyces species, etc.), animal cell, insect cell, and so on]. In addition, cell-free expression system and plant cell system which are usually used in this field can also be carried out.

Specifically, for Escherichia species, coli bacillus (Escherichia coli, for example, BL21, BL21 (DE3), K-12, DH1, DH5, DH5α, M15, HB101, C600, XL-1 Blue, JM109, JM105, JM127, XL1-Blue, VCS257, TOP10, and the like) are included. For Bacillus species, B. subtilis, B. brevis, B. borstelenis, and the like are included. Yeast strain such as S. cerevisiae, Scizo. pombe, A. nidulans, Pichia pastoria, and the like, or Aspergillus filamentous bacteria such as Asperigillus nidulans are also included. As to animal cell, monkey cell COS-7, Vero, Chinese hamster ovary cell CHO, mouse L cell, human Hela cell, FL cell, and the like are included. As to insect cell, BmN4, Sf9, and the like are included, but not particularly limited thereto.

In addition to this, Competent Cell which has a higher transduction efficiency for plasmid or phage DNA may also be used. For example, E. coli DH5α Competent Cell, E. coli JM109 Competent Cell (produced by TAKARA BIO Inc.), and the like are included.

Transformation (or transduction) of the host cell by expression vector can be performed using heretofore known method.

For example, in the case where the host cell is bacterium (for example, in the case of E. coli), transformation (or transduction) of the host cell can be performed by a routine procedure such as, for example, Cohen et al. method (Proc. Natl. Acad. Sci. U.S.A. (1972), 9, 2110), protoplast method (Mol. Gen. Genet. (1979) 168, 111), Competent method (J. Mol. Biol. (1971), 56, 209), or M. Morrison's method (Methods in Enzymology, 68, 326-331, 1979). In addition, when commercially available Competent Cell is used, transformation (or transduction) of the host cell may be performed according to the protocol attached to the product.

Here, a method for confirming whether the transformant which is transformed by "a recombinant vector for expression incorporating a fragment comprising a genome sequence encoding objective βG-binding protein" is obtained includes, for example, a method in which by utilizing a gene for drug resistance possessed preliminarily by the expression vector which is used for obtaining the recombinant vector, the drug resistance of the transductant is checked and confirmed. For example, when pTrcHis2 vector is used as an expression vector, the aforementioned vector has a gene for ampicillin resistance (amp'). And so, this method is the one in which the transformant obtained is cultured in a medium added with ampicillin, and the cultured transformant (ampicillin resistant strain) is confirmed to be a transformant which is transformed by a recombinant vector for expression incorporating a nucleotide sequence encoding objective βG-binding protein.

To make certain that the obtained transformant (transductant) produces the objective βG-binding protein involved in the present invention (hereafter, sometimes referred to as "recombinant βG-binding protein") (the gene for βG-binding protein is expressed), for example, in addition to a routine procedure of hybridization such as Southern hybridization and colony hybridization using a probe, there is, for example, a method as described below.

In the case where the recombinant βG-binding protein is not excreted in a culture solution of the transformant, for example, when it is expressed as a transmembrane type protein, the transformant obtained is treated by a routine procedure for homogenizing or lysing cell (for example, supersonic treatment, treatment with homogenizer or the like, treatment with membrane-lysing agent such as an appropriate surface active agent, and the like), to obtain the lysate thereof. And, for the lysate (if need arises, after carrying out further purification of protein), for example, a usual immunological measurement method (dot Western blotting method, Western blotting method, and the like) is carried out using anti-tag peptide antibody, and by selecting the transductant which is confirmed to express tag peptide in the culture supernatant, the transformant which expresses objective recombinant βG-binding protein can be obtained.

In addition, when a recombinant fragment derived from horseshoe crab factor G-subunit α is excreted in the culture solution (culture supernatant) of the aforementioned transductant, a usual immunological measurement method is carried out for the culture solution (culture supernatant) by the same procedure as carried out for the above described lysate, and the transformant which expresses objective recombinant βG-binding protein may be selected and obtained by the same procedure.

3. Expression of βG-Binding Protein

The βG-binding protein involved in the present invention can be obtained by culturing the transformant which is transformed by plasmid vector for expression incorporating a sequence comprising gene for βG-binding protein obtained by the way as described above in a nutrient medium, and by allowing the transformant to produce the recombinant βG-binding protein.

The nutrient medium preferably contains a carbon source, an inorganic nitrogen source or an organic nitrogen source, which are required for the growth of host cell (transformant). The carbon source includes, for example, glucose, dextran, soluble starch, sucrose, and the like; the inorganic nitrogen source or the organic nitrogen source includes, for example, ammonium salts, nitrate salts, amino acid, corn steep liquor, peptone, casein, meat extract, soybean cake, potato extraction solution, and the like. Moreover, upon request, other nutrients (for example, calcium chloride, sodium dihydrogen phosphate, and magnesium chloride), vitamin, antibiotics, growth factor, and the like may be contained. As for pH of the medium, a range of about pH 5 to pH 8 is desirable.

Cultivation is carried out by the method known in this industry. Cultural conditions such as, for example, temperature, pH of the medium, and fermentation time are selected so that highest titer of the βG-binding protein involved in the present invention can be obtained.

When a transformant (transductant) in which host of the transformant is *E. coli* is cultured, the cultivation may be carried out under the conditions of a routine procedure for culturing *E. coli* in a medium usually used, however, as the medium to be used for the cultivation, liquid medium is suitable.

Medium to be used when a transformant in which the host is *E. coli* is cultured may be the medium usually used when *E. coli* is cultured. For example, synthetic medium such as D-MEM and RPMI, LB medium, 2×YT medium, Terrific Broth, M9 medium (Miller, Journal of Experiments in Molecular Genetics, 431-433, Cold Spring Harbor Laboratory, New York, 1972), and the like are included. Cultivation can be carried out usually at 14° C. to 42° C., and preferably 28° C. to 39° C., for about 3 hours to 24 hours with aeration and agitation, if necessary. In addition, as need arises, drug such as isopropyl-β-D-thiogalactopyranoside (IPTG), 3β-indolylacrylic acid may be added.

4. Recovery of Recombinant βG-Binding Protein

The βG-binding protein involved in the present invention can be obtained from the culture obtained as described above by the following procedure.

That is, in the case where the βG-binding protein involved in the present invention is present in periplasm or cytoplasm of the cultured transformant, the culture is subjected to a routine procedure such as filtration or centrifugal separation to collect bacterial body or cells, and the bacterial body or cells are suspended in an appropriate buffer solution, and after homogenizing cell wall and/or cell membrane of the cell and the like by the method, such as, for example, treatment with surface active agent, supersonic treatment, lysozyme treatment, freezing and thawing, a crude extraction solution containing the βG-binding protein involved in the present invention is obtained by the method such as centrifugal separation or filtration. And, from the aforementioned crude extraction solution, the βG-binding protein involved in the present invention is purified and isolated according to a common procedure used to purify and isolate natural protein or synthetic protein so as not to get mixed in with βG.

Method for isolating and purifying the βG-binding protein includes, for example, a method using solubility such as salting-out, solvent precipitation method; a method using molecular weight difference such as dialysis, ultrafiltration, gel filtration, sodium dodecyl sulfate-polyacrylamide gel electrophoresis; a method using electric charge such as ion exchange chromatography; a method using specific affinity such as affinity chromatography, a method using difference in hydrophobicity such as reversed phase high performance liquid chromatography; and a method using difference in isoelectric point such as isoelectric focusing electrophoresis.

For example, when an expression vector such as pTrcHis2 vector comprising preliminarily a sequence encoding a tag peptide such as His tag gene tag peptide is used, the expressed recombinant βG-binding protein has a His tag. Therefore, by subjecting a solution containing the recombinant βG-binding protein to affinity chromatography using a column packing material containing nickel ion, such as Ni-NTA (nickel-nitrilotriacetic acid), the objective recombinant βG-binding protein can be refined.

In addition, a solution containing the recombinant βG-binding protein purified by the above described method may be further subjected to affinity chromatography using a column packing material bound with the β-binding protein involved in the present invention. Especially, when the host cell used for the expression of recombinant βG-binding protein is eukaryotic organism such as yeast, βG produced by the host may also be contained in the host cell product. Therefore, to remove the βG derived from host cell and to obtain the objective recombinant βG-binding protein, it is preferable to add this affinity chromatography process further to the above described purification process.

Existence of the βG-binding protein involved in the present invention which is isolated and purified in this way can be measured and determined, for example, by ELISA and the like using anti-His antibody.

Hereinafter, the present invention will be further explained in detail by referring to the following Examples, but the scope of the present invention is by no means limited thereto.

EXAMPLES

Example 1

(1) Recovery of RNA

Using a reagent for extracting RNA, ISOGEN (produced by Nippon Gene Co., Ltd.), and according to a protocol attached to the product, total RNA was recovered from the hemocyte of horseshoe crab (*Limulus polyphemus*) as follows.

First, 640 mg of hemocyte of horseshoe crab (*Limulus polyphemus*) (American-grown) was added to a tube in which 7 mL of ISOGEN was placed previously, and the hemocyte was homogenized using POLYTRON homogenizer (manufactured by Kinematica AG).

After the hemocyte homogenate obtained was incubated at room temperature for 5 minutes, 1.4 mL of chloroform was added thereto, and agitated for 15 seconds, and further incubated at room temperature for 3 minutes. After that, centrifugal separation of the homogenate was carried out by 12000G at 4° C. for 15 minutes, then aqueous phase was transferred to a new tube and 3.5 mL of isopropanol was added and agitated, and followed by incubation at room temperature for 10 minutes. Subsequently, centrifugal separation of the homogenate was carried out at 4° C. and 12000G for 10 minutes, and precipitate was obtained. The obtained precipitate was washed with 7 mL of 70% ethanol, and then dried, and the RNA precipitate was obtained. The obtained RNA precipitate was dissolved in 800 µL of sterile water. Absorbance of the obtained RNA solution was measured and the quantity of total RNA obtained was determined A 779 μg of total RNA was obtained from 640 mg of the hemocyte of horseshoe crab (*Limulus polyphemus*).

(2) Purification of mRNA

Using Oligotex™-dT30<Super>(produced by TAKARA BIO Inc.), mRNA was purified by the following method.

First, to 250 μL of aqueous total RNA solution (about 243 μg as total RNA) obtained in the above (1), 250 μL of buffer solution (10 mM Tris-HCl, 1 mM EDTA, 0.1% SDS, pH7.5) was added, and further 500 μL of Oligotex™-dT30 was added, then the mixture was reacted by incubating at 65° C. for 5 minutes. The reaction solution was left on ice for 3 minutes. Subsequently, the reaction solution was added with 0.1 mL of 5 M NaCl, and incubated at 37° C. for 10 minutes. After that, the reaction solution was subjected to centrifugal separation at 15000 rpm for 3 minutes to remove supernatant solution, and pellet was dissolved in 450 μL of TE (Tris-EDTA buffer, pH 8.0). After the pellet solution was incubated at 65° C. for 5 minutes, the solution was left on ice for 3 minutes. After that, the pellet solution was centrifuged at 20000G for 3 minutes; and a 400 μL portion of supernatant was recovered. After the supernatant was treated by usual ethanol precipitation process, the obtained precipitate was dissolved in 10 μL of TE to obtain a purified mRNA solution.

(3) Production and PCR Cloning of cDNA 1) cDNA

Using the purified mRNA obtained in the above (2) as a template, usual reverse transcription reaction was carried out using Oligo (dT)$_{12-18}$ (produced by Wako Pure Chemical Industries, Ltd.) and Reverscript II (produced by Nippon Gene Co., Ltd.) to synthesize cDNA.

2) PCR

The genome sequence encoding *Limulus polyphemus* factor G-subunit α had not been determined. Therefore, considering that the primers which amplify the genome sequence encoding *Tachypleus tridentatus* factor G-subunit α were designed from nucleotide sequence encoding *Tachypleus tridentatus* factor G-subunit α, and if the PCR was carried out using this primer, the nucleotide sequence encoding *Limulus polyphemus* factor G-subunit α could be amplified, the idea was put into practice as described below.

First, on the basis of the genome sequence of *Tachypleus tridentatus* factor G-subunit α (shown in SEQ ID NO: 11) disclosed in NCBI (National Center for Biotechnology Information) database, primer sequence described below was designed and synthesized by Sigma-Aldrich Corp. on consignment.

Primer Sequence:

```
primer F1:
5'-gcaatgttggtgttgc-3'          (SEQ ID NO: 21)

primer R1:
5'-gaagaaacaacagctgttgacc-3'    (SEQ ID NO: 22)
```

The primer F1 among the above described primers corresponds to a sequence of 16 nucleotides comprising 3 nucleotides (gca: the part of the sequence considered to encode signal sequence) in 5' side from initiation codon and a sequence from subsequent initiation codon to 13th nucleotide of 3' side of the genome encoding *Tachypleus tridentatus* factor G-subunit α disclosed in the NCBI (National Center for Biotechnology Information) database. In addition, the R1 primer encodes several amino acids in C-terminal side of the above described *Tachypleus tridentatus* factor G-subunit α.

The PCR was carried out using this primer pair and using cDNA obtained in the above (3)-1) as a template, under the reaction conditions described below. After heating at 98° C. for 2 minutes, the reaction was repeated 30 cycles of a reaction cycle composed of heating at 95° C. for 15 seconds, 50° C. for 30 seconds and 68° C. for 2 minutes and in every cycle, and finally the reaction was performed at 68° C. for 5 minutes.

Reaction Conditions of the PCR:
  sterile water: 12 μL;
  cDNA: 2 μL;
  primer F1: 1 μL;
  primer R1: 1 μL;
  0.2 mM dNTP (mixture of dATP, dGTP, dCTP, and dTTP) (produced by Nippon Gene Co., Ltd.): 2 μL;
  2×TOPOTAQ Amplification Buffer with 6 mM $MgCl_2$ (produced by Wako Pure Chemical Industries, Ltd.): 20 μL;
  TOPOTAQ DNA Polymerase (produced by Wako Pure Chemical Industries, Ltd.): 2 μL.

The PCR product obtained was subjected to 1% agarose gel electrophoresis containing 1 μg/mL ethidium bromide, and a gel portion around 1.2 Kbp band was cut out. The PCR product was purified from the gel cut out using QIAquick Gel Extraction kit (produced by Qiagen GmbH).

(4) Preparation of Recombinant Vector and Determination of Nucleotide Sequence

After mixing 0.1 μg of pGEM-T Easy (produced by Promega Corp.) with about 5 μg of the PCR product obtained in the above (3)-2) and 5 μL of DNA ligation kit Ver. 2, I solution (produced by TAKARA BIO Inc.), total volume was made to 10 μL with sterile distilled water. Subsequently, ligation reaction was carried out at 16° C. for 1 hour to obtain the recombinant vector. In the obtained recombinant vector, the same nucleotide sequence as the cDNA obtained in the above (3)-1), that is, the nucleotide sequence encoding *Limulus polyphemus* factor G-subunit α was inserted. Therefore, the obtained recombinant vector was named "*Limulus polyphemus* factor G α/pGEM-T".

Using 200 ng of the obtained recombinant vector *Limulus polyphemus* factor G α/pGEM-T as a template, and using the same primer pair as used in the above (3)-2), sequencing reaction was carried out using DYEnamic ET Terminator Cycle Sequencing Kit (produced by GE Healthcare Bio-Science AB) according to the method given in a manual supplied.

(5) Homology Search of Nucleotide Sequence

Decoding of nucleotide sequence of the obtained sequencing reaction product [having the same nucleotide sequence as the cDNA obtained in the above (3)-1)] was carried out using BaseStation (Bio-Rad Laboratories, Inc.). The nucleotide sequence encoding *Limulus polyphemus* factor G-subunit α obtained by decoding is shown in SEQ ID NO: 1, and amino acid sequence which is deduced from the nucleotide sequence and is encoded by this nucleotide sequence is shown in SEQ ID NO: 2, respectively.

Subsequently, using NCBI (National Center for Biotechnology Information) database, homology search (BLAST) on nucleotide sequence of the PCR product inserted in the vector was performed. As a result, it became clear that nucleotide sequence of the PCR product inserted in the vector, i.e., nucleotide sequence of cDNA showed high homology to the known genome sequence of *Tachypleus tridentatus* factor G-subunit α, however, these were different from each other. That is, homology between the known genome sequence of *Tachypleus tridentatus* factor G-subunit α and the genome sequence corresponding to *Limulus polyphemus* factor G-subunit α (signal peptide and partial sequence of N-terminal side, and stop codon were excluded) was 85.6%. In addition, from comparison of the amino acid sequences deduced from respective nucleotide sequences, homology of both sequences was 79.5%.

Furthermore, on the basis of amino acid sequence (SEQ ID NO: 2) which is deduced from obtained nucleotide sequence of cDNA and encoded by this nucleotide sequence, structure of *Limulus polyphemus* factor G-subunit α was analyzed in detail. Consequently, it became clear that in the *Limulus polyphemus* factor G-subunit α, there existed β-1,3-glucanase like domain at N-terminal side, dimeric xylanase Z (XlnZ) like domain which was presumed to be βG-binding domain at C-terminal side, and xylanase A (XlnA)-like domain at the center. Points of difference from the known amino acid sequence of *Tachypleus tridentatus* factor G-subunit α was: (i) a linker sequence between dimeric sequences of βG-binding domain present at C-terminal side was completely different; (ii) QQES motif which was a structural motif present in the xylanase A-like domain at the center of the sequence was repeated 3 times in *Tachypleus tridentatus* factor G-subunit α, while that in *Limulus polyphemus* factor G-subunit α was repeated twice.

Based on the above described analytical results, nucleotide sequence, amino acid sequence, and protein structures were compared between *Limulus polyphemus* factor G-subunit α and *Tachypleus tridentatus* factor G-subunit α. Results are collectively shown in Table 2 below.

TABLE 2

| | | Factor G-subunit α | |
| --- | --- | --- | --- |
| | | *Limulus polyphemus* | *Tachypleus tridentatus* |
| Number of amino acid | | 649 | 654 |
| Number of amino acid in gap structure | | 5 | |
| Deduced molecular mass | Whole length | 72.5 KDa | 73.9 KDa |
| | XlnZ-like domain (dimer) | 28.6 KDa | 29.2 KDa |
| Deduced isoelectric point | Whole length | 5.20 | 5.94 |
| | XlnZ-like domain (dimer) | 8.57 | 6.19 |
| Homology between *Limulus polyphemus* and *Tachypleus tridentatus* | Whole length | Amino acid sequence: 79.5% (nucleotide sequence: 85.6%) | |
| | XlnZ-like domain (dimer) | Amino acid sequence: 83.3% (nucleotide sequence: 85.9%) | |
| | XlnZ-like domain | Amino acid sequence: 78.8% (nucleotide sequence: 87.4%) | |
| | Glucanase-like domain | Amino acid sequence: 77.2% (nucleotide sequence: 85.1%) | |
| QQWS motif | | Twice repetition | Three times repetition |

In addition, schematic diagram of structure of *Limulus polyphemus* factor G-subunit α predicted from the above-mentioned analysis is shown in FIG. 1, and schematic diagram of the known structure of *Tachypleus tridentatus* factor G-subunit α is shown in FIG. 2, respectively.

(6) Preparation of Expression Vector

First, using recombinant vector *Limulus polyphemus* factor Gα/pGEM-T obtained in the above (4) as a template, PCR was carried out. As to the primer, primer sequences described below which were designed from the nucleotide sequence clarified in the above (5) (SEQ ID NO: 1) and synthesized by a routine synthesis method by Sigma-Aldrich Corp. were used. By the PCR using these primers, a nucleotide sequence of the 696th to the 1947th from 5'-terminal in the nucleotide sequence clarified in the above (5) and shown in SEQ ID NO: 1 encoding *Limulus polyphemus* factor G-subunit α, that is, a nucleotide sequence encoding "an amino acid sequence from the 233rd (asparagine) to the 649th (valine) in the amino acid sequence of *Limulus polyphemus* factor G-subunit α shown in SEQ ID NO: 1" can be amplified.

Primer Sequence:

```
primer F2:
5'-aatacaccttctcctgttgacg-3';     (SEQ ID NO: 23)

primer R2:
5'-ctggattaagattacaaaggtt-3'.     (SEQ ID NO: 24)
```

It should be noted that the peptide having amino acid sequence from the 233rd to the 649th of *Limulus polyphemus* factor G-subunit α was named "fragment-a derived from *Limulus polyphemus* factor G-subunit α". That is, the "fragment-a derived from *Limulus polyphemus* factor G-subunit α" has an amino acid sequence shown in SEQ ID NO: 4. Further, amino acid sequence of the aforementioned fragment-a is encoded by the nucleotide sequence shown in SEQ ID NO: 3.

A schematic diagram of the fragment-a derived from *Limulus polyphemus* factor G-subunit α is shown in the lower drawing of FIG. 1 so that it can be compared with the schematic diagram of *Limulus polyphemus* factor G-subunit α. That is, the fragment-a derived form *Limulus polyphemus* factor G-subunit α possesses xylanase A-like domain (existing two QQWS motifs therein) and a dimeric xylanase Z like domain (XlnZ) which is presumed to be βG-binding domain of *Limulus polyphemus* factor G-subunit α.

PCR was carried out under the reaction conditions described below. After heating at 98° C. for 2 minutes, sequential heating at 95° C. for 15 seconds, 63° C. for 30 seconds and 68° C. for 1 minute was repeated for 30 times, and finally heated at 68° C. for 5 minutes.

Reaction conditions of the PCR:
sterile water: 12 µL;
*Limulus polyphemus* factor G α/pGEM-T: 2 µL;
primer F2: 1 µL;
primer R2: 1 µL;
0.2 mM dNTP (mixture of dATP, dGTP, dCTP, and dTTP) (produced by Nippon Gene Co., Ltd.): 2 µL;
2×TOPOTAQ Amplification Buffer with 6 mM $MgCl_2$ (produced by Wako Pure Chemical Industries, Ltd.): 20 µL;
TOPOTAQ DNA Polymerase (produced by Wako Pure Chemical Industries, Ltd.): 2 µL.

The PCR product obtained was subjected to 1% agarose gel electrophoresis containing 1 µg/mL ethidium bromide, and a gel portion around 1.3 Kbp band was cut out. The PCR product was purified from the gel cut out using QIAquick Gel Extraction kit (produced by Qiagen GmbH).

Subsequently, 1 µL portion of pTrcHis2 vector (produced by Invitrogen Corp.) and 4 µL of the obtained PCR product were mixed, and the total volume was adjusted to 5 µL with sterile water. Subsequently, ligation reaction was carried out by incubating at 25° C. for 5 minutes to prepare a recombinant vector. Using this recombinant vector, DH5α competent cell line derived from *E. coli* K strain (produced by Nippon Gene Co., Ltd.) was transformed by a routine procedure. This transformant was cultured on an LB agar medium containing ampicillin (produced by Wako Pure Chemical Industries, Ltd., 100 µg/mL) at 37° C. for 1 day, and allowed to grow colony.

From transformant of each colony, DNA was extracted, respectively, by a routine procedure, and nucleotide sequence was confirmed using BaseStation (produced by Bio-Rad Laboratories, Inc.). And, the transformant having a nucleotide sequence as a reading frame encoding an amino acid sequence of SEQ ID NO: 4 was named "fragment-a derived from *Limulus polyphemus* factor G-subunit α (233-649 aa)/DH5α".

(7) Expression of Fragment-a Derived from *Limulus polyphemus* Factor G-Subunit α (233-649 aa)

The transformant of fragment-a derived from *Limulus polyphemus* factor G-subunit α (233-649 aa)/DH5α selected in the above (6) was cultured overnight. The culture solution (5 mL) was inoculated into 1 L of LB medium containing 0.100 mg/L ampicillin, and cultured at 37° C. for 4 hours. At the time when $OD_{600nm}$ of culture broth reached 0.8, 1 mM final concentration of isopropyl-β-thiogalactopyranoside (IPTG) (produced by Wako Pure Chemical Industries, Ltd.) was added to the culture medium, and further cultured with stirring at 20° C. for 48 hours.

After cultivation, culture solution was subjected to centrifugal separation, and the resultant precipitate (bacterial body) was collected. After washing the precipitate with distilled water (produced by Otsuka Pharmaceutical Co., Ltd.), the bacterial body was homogenized by ultrasonic wave, then subjected to centrifugal separation (5000g×10 minutes) to obtain supernatant fraction.

The expressed protein has six of His which are derived from pTrcHis2 vector attaching in the C-terminal side. And so, using Ni-agarose (produced by Wako Pure Chemical Industries, Ltd.), protein was purified from the supernatant fraction obtained as described above by carrying out affinity purification with Ni-agarose according to the method described in the manual supplied.

(8) Confirmation of Expression of the Fragment-a Derived from *Limulus polyphemus* Factor G-Subunit α (233-649 aa)

First, after the expressed protein purified in the above (7) (recombinant fragment-a derived from *Limulus polyphemus* factor G-subunit α) was subjected to SDS-PAGE using polyacrylamide gel (produced by Wako Pure Chemical Industries, Ltd.), the protein was transferred to PVDF membrane using iBlot (produced by Invitrogen Corp.). After subjecting the PVDF membrane to blocking process with 1% Blockace, the membrane was reacted with peroxidase-labeled anti-His antibody (produced by GE Healthcare Bio-Science AB) at room temperature for 1 hour. The PVDF membrane after the reaction was washed 3 times with PBS-T (containing 0.05% polyoxyethylene(20)sorbitan monolaurate) (produced by Wako Pure Chemical Industries, Ltd.), then allowed to emit light using ECLplus (produced by GE Healthcare Bio-Science AB), which was imaged on an X-ray film (produced by GE Healthcare Bio-Science AB).

Separately, the gel after SDS-PAGE was stained using silver staining kit (produced by Wako Pure Chemical Industries, Ltd.) according to the method given in the manual supplied.

Figure 3:
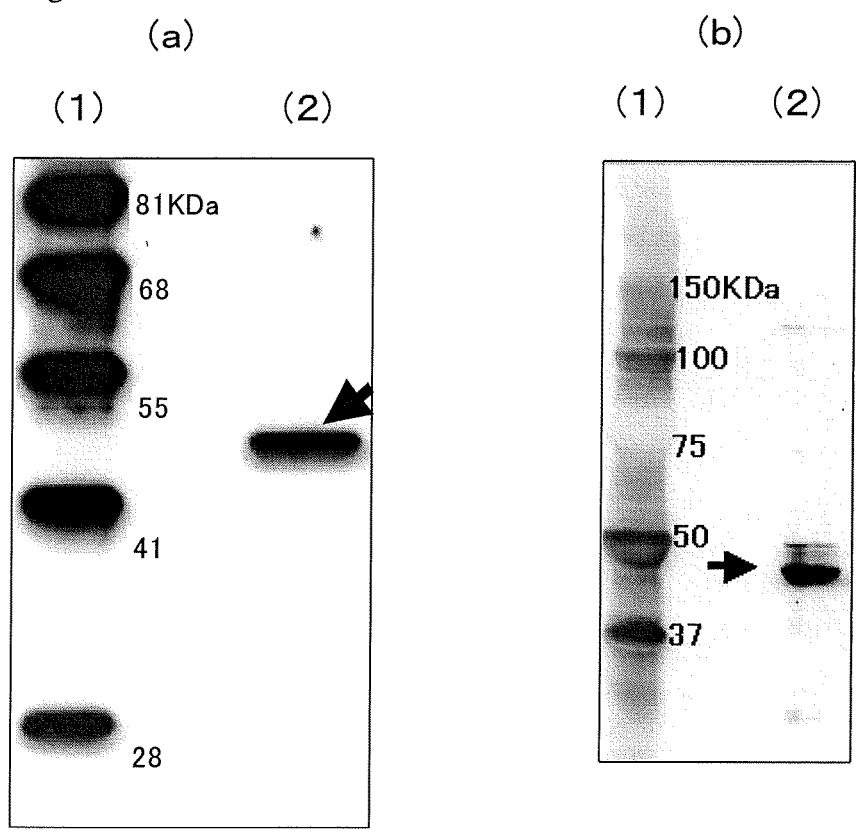
FIG. 3 shows the results of protein expression of the fragment-a (233-649 aa) derived from *Limulus polyphemus* factor G-subunit α obtained in Example 1. (a) shows the results of Western blotting, (b) shows the results of silver staining of the gel after SDS-PAGE, respectively. In addition, in FIG. 3 (*a*) and FIG. 3 (*b*), lane (1) and lane (2) show the results of protein molecular weight markers and affinity purified fragment-a were used as a sample, respectively.

Results are shown in FIG. 3(*a*) and (*b*). FIG. 3 (*a*) shows the results of Western blotting, and FIG. 3 (*b*) shows the results of silver staining of the gel after SDS-PAGE, respectively.

In addition, in FIG. 3 (*a*), lane (1) is a result when molecular weight marker Dr. Western (produced by Oriental Yeast Co., Ltd.) was used as a sample, and lane (2) is a result when affinity-purified fragment-a was used as a sample.

In FIG. 3 (*b*), lane (1) is a result when protein molecular weight marker Precision Plus Protein Standards (produced by Bio-Rad Laboratories, Inc.) was used as a sample, and lane (2) is a result when affinity-purified fragment-a was used as a sample.

As is clear from the results shown in FIG. 3 (*a*), a band showing the expressed protein reacted with peroxidase-labeled anti-His antibody (indicated by arrow) could be detected.

Moreover, molecular weight of the fragment-a derived from *Limulus polyphemus* factor G-subunit α, presumed from the amino acid sequence shown in SEQ ID NO: 4 is about 48 kDa. As is clear from the results shown in FIG. 3 (*b*), size of protein of the band (FIG. 3 (*a*)) identified by SDS-PAGE, and reacted with peroxidase-labeled anti-His antibody is about 48 kDa, and the band was confirmed in the same position as the molecular weight of the fragment-a derived from *Limulus polyphemus* factor G-subunit α.

Therefore, it was confirmed that the fragment-a derived from *Limulus polyphemus* factor G-subunit α (233-649 aa) could be expressed by the above described method, and a recombinant fragment-a derived from *Limulus polyphemus* factor G-subunit α could be obtained.

Example 2

Measurement of βG by Various βG-Binding Proteins (1) Preparation of Various βG-Binding Proteins
1) Fragment-a Derived from Horseshoe Crab (*Limulus polyphemus*) Factor G-Subunit α

The recombinant fragment-a derived from *Limulus polyphemus* factor G-subunit α obtained in Example 1 was used.

2) Preparation of β Recognition Protein (1-479 aa) Derived from Silkworm

In FIG. 3 of Ochiai M. et al., J. Biol. Chem., vol. 275, No. 7, p. 4995-5002 (2000), amino acid sequence of β-1,3-glucan recognition protein derived from silkworm, and nucleotide sequence of gene encoding it have been described. The aforementioned protein is a protein consisting of 479 amino acids, which is encoded by a nucleotide sequence of 1575 bp. According to the method described in the above described literature and a method given in the above described Example 1, β-1,3-glucan recognition protein derived from silkworm disclosed in FIG. 3 of the above described literature was obtained (hereinafter, referred to as "βG recognition protein (1-479 aa) derived from silkworm" in the present description).

That is, mRNA was purified from an extract obtained from hemocyte of silkworm larva, and cDNA was obtained by reverse transcription reaction. Using the obtained cDNA as a template, and using 5'-tacgaggcaccaccg-3' (SEQ ID NO: 39) as F primer and 5'-gttaaagtttttgcaata-3' (SEQ ID NO: 40) as R primer, PCR was carried out under the conditions described in the aforementioned literature. The obtained PCR product was subjected to 1% agarose gel electrophoresis in the presence of 1 µg/mL ethidium bromide, and a gel portion of the band around 1.5 kbp was cut out. The PCR product was purified from the gel portion using QIAquick Gel Extraction kit.

Subsequently, preparation of expression vector using the same expression vector (pTrcHis2 vector) as in Example 1 (6), and transformation of the DH5α competent cell line derived from K coli K strain were carried out. Then, by the same method as in Example 1 (7), the transformant was cultured and "βG recognition protein (1-479 aa) derived from silkworm" was expressed. After cultivation, protein was purified from culture solution by the same method as in Example 1 (7).

3) Preparation of βG Recognition Binding Protein (1-454 aa) Derived from Silkworm An amino acid sequence of Gram-negative bacteria-binding protein derived from silkworm and a nucleotide sequence encoding the protein have been described in FIG. 3 of Proc. Natl. Acad. Sci. USA vol. 93, p. 7888-7893 (1996). The aforementioned protein is the one which consists of 467 amino acids, and encoded by nucleotide sequence of 2257 bp. Since it is described in the above described literature that the structure of the aforementioned protein "comprises glucanase-like domain and has a resemblance to factor G domain a", this protein is assumed to have a property to bind with βG.

And so, according to the method described in the above described literature and a method given in the above described Example 1, Gram-negative bacteria-binding protein derived from silkworm disclosed in FIG. 3 of Proc. Natl. Acad. Sci. USA, vol. 93, p. 7888-7893 (1996) (hereinafter, referred to "βG recognition binding protein (1-454 aa) derived from silkworm" in the present description) was obtained.

That is, mRNA was purified from an extract obtained from hemocyte of silkworm larva, and cDNA was obtained by reverse transcription reaction. Using the obtained cDNA as a template, and using 5'-atatcgtacgctcaaatgcc-3' (SEQ ID NO: 41) as F primer and 5'-ctttgtcaaagttatcgcctta-3' (SEQ ID NO: 42) as R primer, PCR was carried out under the conditions described in the aforementioned literature. The obtained PCR product was subjected to 1% agarose gel electrophoresis in the presence of 1 μg/mL ethidium bromide, and a gel portion of the band around 1.5 kbp was cut out. The PCR product was purified from the gel portion using QIAquick Gel Extraction kit.

Subsequently, preparation of expression vector using the same expression vector (pTrcHis2 vector) as in Example 1 (6), and transformation of the DH5α competent cell line derived from E. coli K strain were carried out. Then, by the same method as in Example 1-(7), the transformant was cultured and "βG recognition binding protein (1-454 aa) derived from silkworm" was expressed. After cultivation, the protein was purified from culture solution by the same method as in Example 1 (7).

4) Preparation of βG Recognition Protein (181-471 aa) Derived from Indian Meal Moth In the hemolymph of Indian meal moth (*Plodia interpunctella*), there exists βG recognition protein (β-1,3-glucan recognition protein). In Fabrick J. A., et al., Insect Biochem. Mol. Biol., vol. 33, p. 579-594, 2003, an amino acid sequence of the protein and a nucleotide sequence encoding the protein have been described. It consists of 471 amino acids and has glucanase-like part (glucanase-like domain) in the C-terminal side (Fabrick J. A., et al., J. Biol. Chem., vol. 279, No. 25, p. 26605-26611, 2004, FIG. 1).

And so, according to the method described in Fabrick J. A., et al., Insect Biochem. Mol. Biol., vol. 33, p. 579-594, 2003 and a method given in the above described Example 1, the protein of the glucanase-like domain of the βG recognition protein which consists of an amino acid sequence from 181st to 471st in C-terminal side of this Indian meal moth (hereinafter, referred to as "βG recognition protein (181-471 aa) derived from Indian meal moth" in the present description) was obtained.

That is, mRNA was purified from an extract obtained from hemolymph of Indian meal moth, and cDNA was obtained by reverse transcription reaction. Using the obtained cDNA as a template, and using 5'-gaggtcaagtttcctgaag-3' (SEQ ID NO: 43) as F primer and 5'-gtcagagtctatgcgctg-3' (SEQ ID NO: 44) as R primer, PCR was carried out under the conditions described in the aforementioned literature. The obtained PCR product was subjected to 1% agarose gel electrophoresis in the presence of 1 μg/mL ethidium bromide, and a gel portion of the band around 1.5 kbp was cut out. The PCR product was purified from the gel portion using QIAquick Gel Extraction kit.

Subsequently, preparation of an expression vector using the same expression vector (pTrcHis2 vector) as in Example 1-(6), and transformation of the DH5α competent cell line derived from E. coli K strain were carried out. Then, by the same method as in Example 1 (7), the transformant was cultured and "βG recognition protein (181-471 aa) derived from Indian meal moth" was expressed. After cultivation, the protein was purified from culture solution by the same method as described in Example 1 (7).

5) Preparation of Other βG-Binding Protein

In addition, the followings were used as a βG-binding protein.

Dectin-1 derived from mouse (produced by R&D Systems, Inc.);

Mouse anti-(1, 3) βG antibody (produced by Bio supplies Australia Pty Ltd.).

(2) Peroxidase Labeling of the βG-Binding Protein

Using Peroxidase Labeling Kit-NH2 (produced by Dojindo Laboratories Co., Ltd.), and according to the method given in the manual supplied to the kit, each βG-binding protein prepared in the above described (1) was labeled with peroxidase.

(3) Sandwich Measurement

1) Preparation of βG-Binding Protein-Immobilized Microplate for ELISA

The βG-binding proteins prepared in the above (1) were each adjusted to give 5 μg/mL with 50 mM MOPS buffer solution (pH7.0), and each 50 μL aliquot was placed in each well of a microplate for ELISA (produced by Nunk), and by standing still at 10° C. for 16 hours, each βG-binding protein was immobilized to the aforementioned microplate (about 250 ng/well as βG-binding protein).

Subsequently, as a blocking operation for reducing non-specific adsorption, 0.2 mL aliquot of 1% Blockace (produced by Dainippon Sumitomo Pharma Co., Ltd.) solution dissolved in 50 mM phosphate buffered saline (pH 7.0) was dispensed in each well, and after standing still at room temperature for 1 hour, washing of each well was carried out.

2) Preparation of Peroxidase-Labeled βG-Binding Protein

Each peroxidase-labeled βG-binding protein obtained in the above (2) was diluted 8000 times with 1% Blockace solution dissolved in 50 mM phosphate buffered saline (pH 7.0).

3) Preparation of Sample

β-Glucan test Wako "β-glucan standard preparation" (produced by Wako Pure Chemical Industries, Ltd.) was prepared to give 1000 pg/mL in the reduced value of lentinan with 1% Blockace solution dissolved in 50 mM phosphate buffered saline (pH7.0). This was used as a sample.

4) Measurement

A 50 μL of sample (50 pg in the reduced value of lentinan) prepared in the above 3) was added to each well of the βG-binding protein-immobilized microplate for ELISA prepared in the above 1), and reacted at 37° C. for 1 hour. Subsequently, each well was washed 3 times with PBS-T (produced by Wako Pure Chemical Industries, Ltd.). A 50 μL of the peroxidase-labeled βG-binding protein (2 μg/mL) prepared in the above 2) was dispensed in each well, and reacted at 37° C. for 1 hour. After washing each well 3 times with PBS-T and once with distilled water, 50 μL of TMB (3,3',5,5'-tetramethylbenzidine) solution (produced by Wako Pure Chemical Industries, Ltd.) was added to each well, and reacted at 25° C. for 30 minutes. Then, 50 μL of reaction terminating solution (1 M phosphoric acid solution) was added to each well to terminate the reaction. Absorbance at 450 nm was measured using Vmax (produced by Molecular Devices Inc.).

It should be noted that measurement was carried out in a similar way using a sample of 0 pg/mL in the reduced value of lentinan to use as a blank value.

(4) Results

Obtained results are shown in Table 3.

TABLE 3

OD450 nm (×1000)

| | | Peroxidase-labeled protein | | | | | |
|---|---|---|---|---|---|---|---|
| | | i | ii | iii | iv | v | vi |
| Protein immobilized to a plate | i | 41 | 7 | 70 | 51 | 43 | 38 |
| | ii | 38 | 15 | 77 | 61 | 38 | 32 |
| | iii | 36 | 6 | 412 | 24 | 10 | 39 |
| | iv | 20 | 11 | 8 | 18 | 17 | 28 |
| | v | 18 | 7 | 42 | 31 | 15 | 31 |
| | vi | 31 | 8 | 38 | 4 | 21 | 42 |

It should be noted that the numerical value indicated in Table 3 is a value which is obtained by subtracting blank value from the absorbance obtained at 450 nm and multiplied by 1000.

In addition, in Table 3, each symbol is a result when the following sample is used.

i: βG recognition protein derived from silkworm;

ii: βG recognition binding protein derived from silkworm;

iii: Fragment-a derived from factor G-subunit α of horseshoe crab (*Limulus polyphemus*);

iv: βG recognition protein derived from indian meal moth;

v: Dectin-1 derived from mouse;

vi: Mouse anti-(1, 3) βG antibody.

That is, in the above Table 3, for example, when the value is "412" for "immobilized protein on the plate: iii" and "peroxidase-labeled protein: iii", it means that the above described reaction was carried out using "microplate for ELISA immobilized with fragment-a derived from factor G-subunit α of horseshoe crab (*Limulus polyphemus*)" and "peroxidase labeled fragment-a derived from factor G-subunit α of horseshoe crab (*Limulus polyphemus*)", and the value of the obtained absorbance measurement value at 450 nm multiplied by 1000 was "412".

Next, S/N ratios obtained by dividing each measurement value of the obtained absorbance by blank value are shown in the following Table 4.

TABLE 4

S/N

| | | Peroxidase-labeled protein | | | | | |
|---|---|---|---|---|---|---|---|
| | | i | ii | iii | iv | v | vi |
| Protein immobilized to a plate | i | 1.4 | 1.2 | 1.1 | 1.2 | 1.4 | 1.1 |
| | ii | 1.3 | 1.3 | 1.1 | 1.2 | 1.2 | 1.1 |
| | iii | 1.3 | 1.1 | 3.5 | 1.2 | 1.3 | 1.2 |
| | iv | 1.2 | 1.2 | 1.1 | 1.1 | 1.2 | 1.1 |
| | v | 1.1 | 1.1 | 1.3 | 1.2 | 1.2 | 1.1 |
| | vi | 1.3 | 1.2 | 1.3 | 1.1 | 1.3 | 1.2 |

Furthermore, results of evaluation obtained based on the results of Table 3 and Table 4 are shown in the following Table 5.

TABLE 5

Evaluation

| | | Peroxidase-labeled protein | | | | | |
|---|---|---|---|---|---|---|---|
| | | i | ii | iii | iv | v | vi |
| Protein immobilized to a plate | i | X | X | Δ | Δ | X | X |
| | ii | X | X | Δ | Δ | X | X |
| | iii | X | X | ◎ | X | X | X |
| | iv | X | X | X | X | X | X |
| | v | X | X | X | X | X | X |
| | vi | X | X | X | X | X | X |

In Table 5, each symbol has the following meaning.

◎: OD450 nm (×1000) is 200 or more, and S/N is 3.0 or more;

○: OD450 nm (×1000) is 100 or more, and S/N is 1.5 or more;

Δ: OD450 nm (×1000) is 50-99, or S/N is 1.0 or more;

X: OD450 nm (×1000) is 0-49, or S/N is 1.0 or more.

It should be noted that in Table 5, the measurement method using both plate (v) which is immobilized with mouse Dectin I and peroxidase-labeled mouse Dectin I (v) is a measurement method by the sandwich method using 2 molecules of Dectin I which is described in the Non-Patent Literature 1.

On the other hand, in Table 5, the method for measuring βG using βG-binding protein involved in the present invention is a method using both plate (iii) which is immobilized with the fragment-a derived from factor G-subunit α of horseshoe crab (*Limulus polyphemus*) and the fragment-a derived from factor G-subunit α of horseshoe crab (*Limulus polyphemus*).

As is clear from the results of Table 5, the combination in which the value in Table 3 is 100 or more and the S/N ratio in Table 4 is 1.5 or more was a measurement system using the plate (iii) which is immobilized with the fragment-a derived from factor G-subunit α of horseshoe crab (*Limulus polyphemus*) and the fragment-a derived from factor G-subunit α of horseshoe crab (*Limulus polyphemus*).

By the method using 2 molecules of Dectin which is the well-known sandwich measurement system (the method using both a plate immobilized with Dectin and peroxidase-labeled Dectin), favorable result could not be obtained.

From the results mentioned above, it was shown that a sandwich measurement system using fragment-a (iii) derived from factor G-subunit α of horseshoe crab (*Limulus polyphemus*) which is a βG-binding protein involved in the present invention was useful for measuring βG.

Example 3

Sandwich Measurement Using a Fragment Derived from Factor G-Subunit α Of Horseshoe Crab (*Limulus polyphemus*) (1)

(1) Designing of a Fragment Derived from Factor G-Subunit α of Horseshoe Crab (*Limulus polyphemus*)

Based on the amino acid sequence of factor G-subunit α of horseshoe crab (*Limulus polyphemus*) (SEQ ID NO: 2) obtained in Example 1 (5), the following 4 kinds of fragments derived from factor G-subunit α of horseshoe crab (*Limulus polyphemus*) were designed. It should be noted that schematic diagram of each fragment is shown collectively in FIG. 1 so that it can be compared with the schematic diagram of factor G-subunit α of horseshoe crab (*Limulus polyphemus*).

1) Fragment-a derived from factor G-subunit α of horseshoe crab (*Limulus polyphemus*): the fragment-a obtained in Example 1. It consists of an amino acid sequence shown in SEQ ID NO: 4 which is encoded by a nucleotide sequence shown in SEQ ID NO: 3. It corresponds to an amino acid sequence of the part of the 233rd to the 649th from N-terminal of the amino acid sequence of the factor G-subunit α of horseshoe crab (*Limulus polyphemus*) shown in SEQ ID NO: 2. It has a xylanase A-like domain (two QQWS motifs exist) and a dimeric xylanase Z-like domain (XlnZ).

2) Fragment-b derived from factor G-subunit α of horseshoe crab (*Limulus polyphemus*): it consists of an amino acid sequence shown in SEQ ID NO: 6 which is encoded by a nucleotide sequence shown in SEQ ID NO: 5. It corresponds to an amino acid sequence of the part of the 387th to the 649th from N-terminal of the amino acid sequence of the factor G-subunit α of horseshoe crab (*Limulus polyphemus*) shown in SEQ ID NO: 2. It has a dimeric xylanase Z-like domain (XlnZ).

3) Fragment-c derived from factor G-subunit α of horseshoe crab (*Limulus polyphemus*): it consists of an amino acid sequence shown in SEQ ID NO: 8 which is encoded by a nucleotide sequence shown in SEQ ID NO: 7. It corresponds to an amino acid sequence of the part of the 524th to the 649th from N-terminal of the amino acid sequence of the factor G-subunit α of horseshoe crab (*Limulus polyphemus*) shown in SEQ ID NO: 2. It has one xylanase Z-like domain in C-terminal side of the dimeric xylanase Z-like domain (XlnZ) possessed by *Limulus polyphemus* factor G-subunit α.

4) Fragment-d derived from factor G-subunit α of horseshoe crab (*Limulus polyphemus*): it consists of an amino acid sequence shown in SEQ ID NO: 10 which is encoded by a nucleotide sequence shown in SEQ ID NO: 9. It corresponds to an amino acid sequence of the part of the 233rd to the 515th from N-terminal of the amino acid sequence of the factor G-subunit α of horseshoe crab (*Limulus polyphemus*) shown in SEQ ID NO: 2. It has a xylanase A-like domain (two QQWS motifs exist) and one xylanase Z-like domain in N-terminal side of the dimeric xylanase Z-like domain (XlnZ) possessed by *Limulus polyphemus* factor G-subunit α.

(2) Designing of a Fragment Derived from Factor G-Subunit α of Horseshoe Crab (*Tachypleus Tridentatus*)

Based on the nucleotide sequence of factor G-subunit α of horseshoe crab (*Tachypleus tridentatus*) (SEQ ID NO: 11) disclosed in NCBI (National Center for Biotechnology Information) database, the following 4 kinds of fragments derived from factor G-subunit α of horseshoe crab (*Tachypleus tridentatus*) were designed. It should be noted that schematic diagram of each fragment is shown collectively in FIG. 2 so that it can be compared with the schematic diagram of factor G-subunit α of horseshoe crab (*Tachypleus tridentatus*).

1) Fragment-e derived from factor G-subunit α of horseshoe crab (*Tachypleus tridentatus*): it consists of an amino acid sequence shown in SEQ ID NO: 14 which is encoded by a nucleotide sequence shown in SEQ ID NO: 13. It corresponds to an amino acid sequence of the part of the 299th to the 673rd from N-terminal of the amino acid sequence of the factor G-subunit α of horseshoe crab (*Tachypleus tridentatus*) shown in SEQ ID NO: 12. It has a xylanase A-like domain (three QQWS motifs exist) and a dimeric xylanase Z-like domain (XlnZ)

2) Fragment-f derived from factor G-subunit α of horseshoe crab (*Tachypleus tridentatus*): it consists of an amino acid sequence shown in SEQ ID NO: 16 which is encoded by a nucleotide sequence shown in SEQ ID NO: 15. It corresponds to an amino acid sequence of the part of the 410th to the 673rd from N-terminal of the amino acid sequence of the factor G-subunit α of horseshoe crab (*Tachypleus tridentatus*) shown in SEQ ID NO: 12. It has a dimeric xylanase Z-like domain (XlnZ).

3) Fragment-g derived from factor G-subunit α of horseshoe crab (*Tachypleus tridentatus*): it consists of an amino acid sequence shown in SEQ ID NO: 18 which is encoded by a nucleotide sequence shown in SEQ ID NO: 17. It corresponds to an amino acid sequence of the part of the 548th to the 673rd from N-terminal of the amino acid sequence of the factor G-subunit α of horseshoe crab (*Tachypleus tridentatus*) shown in SEQ ID NO: 12. It has one xylanase Z-like domain in C-terminal side of the dimeric xylanase Z-like domain (XlnZ) possessed by *Tachypleus tridentatus* factor G-subunit α.

4) Fragment-h derived from factor G-subunit α of horseshoe crab (*Tachypleus tridentatus*): it consists of an amino acid sequence shown in SEQ ID NO: 20 which is encoded by a nucleotide sequence shown in SEQ ID NO: 19. It corresponds to an amino acid sequence of the part of the 299th to the 547th from N-terminal of the amino acid sequence of the factor G-subunit α of horseshoe crab (*Tachypleus tridentatus*) shown in SEQ ID NO: 12. It has a xylanase A-like domain (three QQWS motifs exist) and one xylanase Z-like domain in N-terminal side of the dimeric xylanase Z-like domain (XlnZ).

(3) Expression of the Fragment Derived from Horseshoe Crab Factor G-Subunit α Subunit Origin Fragment From each nucleotide sequence encoding the amino acid sequence of respective fragments designed in the above (1) and (2), PCR primers which amplify a nucleotide sequence encoding each fragment were designed.

SEQ ID NO of the amino acid sequence of each fragment, SEQ ID NO of the nucleotide sequence encoding the amino acid sequence, and the nucleotide sequence and its SEQ ID NO of primer pair used for cloning respective nucleotide sequences are summarized in the following Table 6.

TABLE 6

| Fragment | | | Used Primer | |
|---|---|---|---|---|
| Name | Nucleotide sequence | Amino acid sequence | primer F | SEQ ID NO: |
| a | SEQ ID NO: 1 | SEQ ID NO: 4 | 5'-aatacaccttctcctgttgacg-3' | 23 |
| b | SEQ ID NO: 5 | SEQ ID NO: 6 | 5'-tctaaattgattcaggccag-3' | 25 |
| c | SEQ ID NO: 7 | SEQ ID NO: 8 | 5'-tctagagtaattcaggcagaaag-3' | 27 |
| d | SEQ ID NO: 9 | SEQ ID NO: 10 | 5'-aatacaccttctcctgttgacg-3' | 29 |

TABLE 6-continued

| | | | Used Primer | |
|---|---|---|---|---|
| e | SEQ ID NO: 13 | SEQ ID NO: 14 | 5'-ggttactattttgtccaaaacagg-3' | 31 |
| f | SEQ ID NO: 15 | SEQ ID NO: 16 | 5'-tctaaattaattcaggcag-3' | 33 |
| g | SEQ ID NO: 17 | SEQ ID NO: 18 | 5'-tctaaattaattcaggcag-3' | 35 |
| h | SEQ ID NO: 19 | SEQ ID NO: 20 | 5'-ggttactattttgtccaaaacagg-3' | 37 |

| Fragment Name | primer R | SEQ ID NO: |
|---|---|---|
| a | 5'-ctggattaagattacaaaggtt-3' | 24 |
| b | 5'-ctggattaagattacaaaggtt-3' | 26 |
| c | 5'-ctggattaagattacaaaggtt-3' | 28 |
| d | 5'-aatattacaaaagtatccagtcag-3' | 30 |
| e | 5'-ggaatatcaattggattagaattacaaaagtg-3' | 32 |
| f | 5'-ggaatatcaattggattagaattacaaaagtg-3' | 34 |
| g | 5'-ggaatatcaattggattagaattacaaaagtg-3' | 36 |
| h | 5'-aatttgaatcaagggcgtcgtaat-3' | 38 |

Each primer having nucleotide sequence described in Table 6 was synthesized by Sigma-Aldrich Corp. on consignment. Subsequently, PCR was carried out by the same method as in Example 1 (6) except for using the aforementioned primer, using recombinant vector *Limulus polyphemus* factor G α/pGEM-T as a template. The obtained PCR product was subjected to 1% agarose gel electrophoresis in the presence of 1 μg/mL ethidium bromide, and a gel portion of the band around 1.5 kbp was cut out. The PCR product was purified from the gel portion using QIAquick Gel Extraction kit.

Subsequently, preparation of expression vector using the same expression vector (pTrcHis2 vector) as in Example 1 (6), and transformation of the DH5α competent cell line derived from *E. coli* K strain were carried out. Then, by the same method as in Example 1 (7), the transformant was cultured and each fragment was expressed. After cultivation, the protein was purified from culture solution by the same method as in Example 1 (7). Mass production of each fragment was carried out by the method described above.

(4) Peroxidase Labeling of the Fragment Derived from Horseshoe Crab Factor G-Subunit α, Using Peroxidase Labeling Kit-SH (produced by Dojindo Laboratories Co., Ltd.), and according to the method given in the manual attached to the kit, each fragment derived from the factor G-subunit α of horseshoe crab (*Limulus polyphemus*) and the factor G-subunit α of horseshoe crab (*Tachypleus tridentatus*) were labeled with peroxidase.

(5) Sandwich Measurement

1) Preparation of Each Horseshoe Crab Factor G-Subunit α Fragment-Immobilized Microplate for ELISA The each *Limulus polyphemus* horseshoe crab factor G-subunit α fragment-immobilized microplate for ELISA and the each *Tachypleus tridentatus* horseshoe crab factor G-subunit α fragment-immobilized microplate for ELISA were prepared by the same method as in Example 2 (3)1) except for using each fragment derived from factor G-subunit α of horseshoe crab (*Limulus polyphemus*) and the factor G-subunit α of horseshoe crab (*Tachypleus tridentatus*) as βG-binding protein.

2) Preparation of Peroxidase Labeled βG-Binding Protein

Peroxidase-labeled each fragment derived from factor G-subunit α of horseshoe crab (*Limulus polyphemus*) and peroxidase-labeled each fragment derived from factor G-subunit α of horseshoe crab (*Tachypleus tridentatus*) were diluted 8000 times with 1% Blockace solution dissolved in 50 mM phosphate buffered saline (pH 7.0).

3) Preparation of Sample

Sample was prepared by the same method using the same reagents as in Example 2 (3) 3).

4) Measurement

A 50 μL of sample (50 pg in the reduced value of lentinan) prepared in the above 3) was added to each well of the microplate prepared in the above 1). Hereafter, absorbance at 450 nm was measured using Vmax (produced by Molecular Devices Inc.) by the same method as in Example 2(3)4).

It should be noted that similar measurement was carried out using a sample of 0 pg/mL in the reduced value of lentinan to use as a blank value.

(6) Results

Obtained results are shown in Table 7.

TABLE 7

OD450 nm (×1000)

| | | Peroxidase-labeled protein | | | | | | | |
|---|---|---|---|---|---|---|---|---|---|
| | | a | b | c | d | e | f | g | h |
| Protein immobilized to a plate | a | 353 | 8 | 32 | 411 | 211 | 376 | 58 | 168 |
| | b | 270 | 3 | 132 | 258 | 167 | 430 | 61 | 27 |
| | c | 114 | 8 | 24 | 260 | 154 | 217 | 29 | 153 |
| | d | NT | NT | NT | 340 | NT | NT | NT | 53 |
| | e | 290 | NT | 164 | 197 | 257 | 355 | NT | 237 |
| | f | 300 | 9 | 50 | 77 | 237 | 429 | 63 | 201 |
| | g | 114 | 12 | 38 | 329 | 62 | 118 | 54 | 226 |
| | h | NT | NT | NT | 305 | NT | NT | NT | 39 |

NT: not test

It should be noted that the numerical value indicated in Table 7 is a value which is obtained by subtracting blank value from the absorbance obtained OD at 450 nm, and multiplied by 1000.

In addition, in Table 7, each symbol is a result when the following fragments derived from horseshoe crab factor G-subunit α is used.

a: fragment-a derived from *Limulus polyphemus* factor G-subunit α;

b: fragment-b derived from *Limulus polyphemus* factor G-subunit α;

c: fragment-c derived from *Limulus polyphemus* factor G-subunit α;

d: fragment-d derived from *Limulus polyphemus* factor G-subunit α;

e: fragment-e derived from *Tachypleus tridentatus* factor G-subunit α;

f: fragment-f derived from *Tachypleus tridentatus* factor G-subunit α;

g: fragment-g derived from *Tachypleus tridentatus* factor G-subunit α;

h: fragment-h derived from *Tachypleus tridentatus* factor G-subunit α.

Reading of the data in Table 7 is the same as that in the case of Table 3.

Next, the value of S/N ratio obtained by dividing each obtained measurement value of absorbance by blank value is shown in the following Table 8.

TABLE 8

| | | | | | S/N | | | | |
|---|---|---|---|---|---|---|---|---|---|
| | | | | | Peroxidase-labeled protein | | | | |
| | | a | b | c | d | e | f | g | h |
| Protein immobilized to a plate | a | 4.8 | 1.2 | 1.2 | 2.0 | 1.6 | 3.8 | 1.4 | 1.5 |
| | b | 3.1 | 1.1 | 1.5 | 3.2 | 1.8 | 4.5 | 1.1 | 1.9 |
| | c | 1.6 | 1.4 | 1.5 | 2.3 | 1.8 | 3.2 | 1.2 | 1.7 |
| | d | NT | NT | NT | 1.9 | NT | NT | NT | 1.6 |
| | e | 3.6 | NT | 1.6 | 1.6 | 2.1 | 3.0 | NT | 1.5 |
| | f | 3.3 | 1.4 | 1.6 | 1.1 | 2.0 | 4.0 | 1.3 | 2.1 |
| | g | 1.6 | 1.5 | 1.6 | 1.8 | 1.6 | 1.6 | 1.4 | 2.3 |
| | h | NT | NT | NT | 1.6 | NT | NT | NT | 1.4 |

NT: not test

Furthermore, the results of evaluation carried out based on the results of Table 7 and Table 8 are shown in the following Table 9.

TABLE 9

| | | | | | Evaluatation | | | | |
|---|---|---|---|---|---|---|---|---|---|
| | | | | | Peroxidase-labeled protein | | | | |
| | | a | b | c | d | e | f | g | h |
| Protein immobilized to a plate | a | ⊚ | X | X | ○ | ○ | ⊚ | ○ | ○ |
| | b | ⊚ | X | ○ | ⊚ | ○ | ⊚ | Δ | X |
| | c | ○ | X | X | ○ | ○ | ○ | X | ○ |
| | d | NT | NT | NT | ○ | NT | NT | NT | Δ |
| | e | ⊚ | NT | ○ | ○ | ○ | ⊚ | NT | ○ |
| | f | ⊚ | X | Δ | Δ | ○ | ⊚ | ○ | ○ |
| | g | ○ | X | X | ○ | Δ | ○ | Δ | ○ |
| | h | NT | NT | NT | ○ | NT | NT | NT | X |

In addition, each symbol in Table 9 has the following meaning

⊚: OD450 nm (×1000) is 200 or more, and S/N is 3.0 or more;

○: OD450 nm (×1000) is 100 or more, and S/N is 1.5 or more;

Δ: OD450 nm (×1000) is 50-99, or S/N is 1.0 or more;

X: OD450 nm (×1000) is 0-49, or S/N is 1.0 or more;

NT: not tested.

As is clear from the results of Table 9, when the combination of immobilized fragment on a plate with peroxidase-labeled fragment (fragment immobilized on a plate-fragment labeled with peroxidase) is classified by the origin of horseshoe crab from which such fragments are derived, it turns out that measurement of the βG can be carried out even when the measurement is carried out using any combination of (*Limulus polyphemus-Limulus polyphemus*), (*Limulus polyphemus-Tachypleus tridentatus*), (*Tachypleus tridentatus-Limulus polyphemus*), and (*Tachypleus tridentatus-Tachypleus tridentatus*).

Moreover, as is clear from the results of Table 9, in the case where βG is measured by the method of the present Example, more preferable combination of (fragment immobilized to a plate-fragment labeled with peroxidase) was (fragment-a-fragment-a), (fragment-a-fragment-f), (fragment-b-fragment-a), (fragment-b-fragment-d), (fragment-b-fragment-f), (fragment-e-fragment-f), and (fragment-f-fragment-f).

Moreover, among the fragment used for measurement, *Limulus polyphemus* factor G-subunit α fragment-a, *Limulus polyphemus* factor G-subunit α fragment-b, *Tachypleus tridentatus* factor G-subunit α fragment-e and *Tachypleus tridentatus* factor G-subunit α fragment-f has two repeated sequence (dimer) of xylanase Z-like domain.

On the other hand, all of *Limulus polyphemus* factor G-subunit α fragment-c, *Limulus polyphemus* factor G-subunit α fragment-d, *Tachypleus tridentatus* factor G-subunit α fragment-g and *Tachypleus tridentatus* factor G-subunit α fragment-h have one xylanase Z-like domain (monomer).

And so, when the combination of the fragment immobilized to a plate with peroxidase-labeled fragment which are used for measurement (fragment immobilized to a plate-fragment labeled with peroxidase) is classified by the structure of xylanase Z-like domain, it turns out that measurement of the βG can be carried out even when the measurement is carried out using any combination of (dimer-dimer), (dimer-monomer), (monomer-dimer), and (monomer-monomer).

Moreover, from these results, it is also suggested that measurement becomes possible if conditions are adjusted, even for some combinations from which good results are not obtained under the measurement conditions of this Example.

From the results mentioned above, it turns out that the measurement of βG can be performed if the sandwich measurement system is practiced using a plate immobilized with βG-binding protein 1 involved in the present invention and a βG-binding protein 2 involved in the present invention which is labeled with a labeling substance, irrespective of the original horseshoe crab from which fragment to be used for measurement is derived and the structure of xylanase Z-like domain of the fragment to be used for measurement.

Example 4

Sandwich Measurement Using Fragment Derived from Horseshoe Crab Factor G-Subunit α (2)

(1) Preparation of Fragment Derived from Horseshoe Crab Factor G-Subunit α

1) Preparation of Fragment-B Derived from *Limulus polyphemus* Factor G-Subunit α and Fragment-G Derived from *Tachypleus tridentatus* Factor G-Subunit α

The fragment-b derived from *Limulus polyphemus* factor G-subunit α and the fragment-g derived from *Tachypleus tridentatus* factor G-subunit α were expressed and purified by carrying out the same method as in Example 3 (3) except for using protease-deficient and B strain-derived BL21 (DE3) as *E. coli* for transformation.

2) Preparation of Fragment-g/Cys Derived from *Tachypleus tridentatus* Factor G-Subunit α

The fragment-g/Cys derived from *Tachypleus tridentatus* factor G-subunit α in which one cysteine residue is introduced in N-terminal of fragment-g (547 aa-673 aa) derived from *Tachypleus tridentatus* factor G-subunit α was designed. Subsequently, the fragment-g/Cys derived from *Tachypleus tridentatus* factor G-subunit α was expressed and purified by carrying out the same method as in Example 3 (3) except for using a primer having a nucleotide sequence (5'-tgttctaaattaattcaggcag-3') described in SEQ ID NO: 45 as primer F, and a primer having a nucleotide sequence described in SEQ ID NO: 36 as primer R (primer F and primer R were synthesized by Sigma-Aldrich Corp. on consignment).

(2) Sandwich Measurement
1) βG-Binding Protein-Immobilized Microplate for ELISA
The same one as prepared in Example 3 (5) 1) was used.
2) Preparation of Peroxidase-Labeled Expression Fragment
Using Peroxidase Labeling Kit-SH, each fragment obtained in the above (1) was labeled with peroxidase according to the method given in the manual attached.
3) Sample:
Sample was prepared by the same method using the same reagents as in Example 2 (3)3).
4) Measurement
A 50 µL of sample (50 pg in the reduced value of lentinan) prepared in the above 3) was added to each well of the microplate prepared in the above (2) 1). Hereafter, absorbance at 450 nm was measured using Vmax (produced by Molecular Devices Inc.) by the same method as in Example 2 (3) 4).

It should be noted that similar measurement was carried out using a sample of 0 pg/mL in the reduced value of lentinan to use as a blank value.

(3) Results
Obtained results are shown in Table 10 and Table 11. Table 10 shows the results in the case where a peroxidase-labeled fragment-b derived from *Limulus polyphemus* factor G-subunit α or a peroxidase-labeled fragment-g derived from *Tachypleus tridentatus* factor G-subunit α which were obtained in the above (1) 1) are used as a peroxidase-labeled fragment.

TABLE 10

| Sequence | | Peroxidaze-labeled fragment | |
|---|---|---|---|
| | | Fragment b | Fragment g |
| Fragment immobilized to a plate | a | ○ | x |
| | b | ○ | x |
| | c | ○ | x |
| | d | N.T | N.T |
| | e | ○ | ○ |
| | f | ○ | x |
| | g | ○ | ○ |
| | h | N.T | N.T |

N.T: not test

In addition, Table 11 shows results in the case where a peroxidase-labeled fragment-g/Cys derived from *Tachypleus tridentatus* factor G-subunit α is used as a peroxidase-labeled fragment.

TABLE 11

| Sequence | | Peroxidaze-laeled fragment (Fragment g/Cys) |
|---|---|---|
| Fragment immobilized to a plate | a | ○ |
| | b | ○ |
| | c | ○ |
| | d | x |
| | e | x |
| | f | x |
| | g | x |
| | h | ○ |

As compared the results of Table 10 and 11 with the results of Table 9 obtained in Example 3, when the fragment-b derived from *Limulus polyphemus* factor G-subunit α obtained in the above (1) 1) is used as a peroxidase-labeled fragment, measurement of βG could be carried out with sufficient sensitivity even in the cases of (fragment-a-fragment-b), (fragment-b-fragment-b), (fragment-c-fragment-b), (fragment-f-fragment-b), and (fragment-g-fragment-b), although measurement of βG could not be carried out by the combination of (fragment immobilized to a plate-fragment labeled with peroxidase) in Example 3.

In addition, when the fragment-g derived from *Tachypleus tridentatus* factor G-subunit α obtained in the above described (1) 1) is used as a peroxidase-labeled fragment, measurement of βG could be carried out with sufficient sensitivity, although the sensitivity was insufficient by (fragment-g-fragment-g) in Example 3.

Furthermore, in the case of Example 3, by a combination of (fragment-c-fragment-g) as the combination of (fragment immobilized to a plate-fragment labeled with peroxidase), βG could not be measured, and also, by a combination of (fragment-b-fragment-g), βG could not be measured in sufficient sensitivity. However, when the fragment-g/Cys derived from *Tachypleus tridentatus* factor G-subunit α obtained in the above (1) 2) was used as peroxidase-labeled fragment, by the combination of (fragment-c-fragment-g/Cys) and (fragment-b-fragment-g/Cys), βG could be measured with sufficient sensitivity.

As a reason for that, the following can be considered. That is, in Example 3, peroxidase is bound to two Cys residues in the βG-binding domain of factor G-subunit α. However, when labeled fragment and sample are reacted for measuring βG, the peroxidase bound to the fragment is considered to interfere the binding between fragment and βG And so, in the present Example, Cys residue was introduced into N-terminal of the fragment and peroxidase was bound thereto. Thereby, peroxidase became not to interfere the binding between fragment and βG, and the measurement of βG is considered to become possible with sufficient sensibility.

As mentioned above, it turned out that three kinds of peroxidase-labeled fragments used in the present Example could react also even in the combination by which the reaction did not occur in Example 3.

Example 5

Sandwich Measurement Using Fragment Derived from Horseshoe Crab Factor G-subunit α (3)

(1) Preparation of Fragment-a/Cys Derived from *Limulus polyphemus* Factor G-Subunit α

Fragment-a/Cys derived from *Limulus polyphemus* factor G-subunit α in which one residue of cysteine was introduced into N-terminal of the fragment-a derived from *Limulus polyphemus* factor G-subunit α was designed. Subsequently, fragment-a/Cys derived from *Limulus polyphemus* factor G-subunit α was expressed and purified by carrying out the same method as in Example 1 (6) to (8) except for using a primer having a nucleotide sequence shown in SEQ ID NO: 46 (5'-tgtctggattaagattacaaagg-3') as primer F, and a primer having a nucleotide sequence shown in SEQ ID NO: 24 as primer R (primer F and primer R were synthesized by Sigma-Aldrich Corp. on consignment).

(2) Peroxidase Labeling of Fragment-a/Cys Derived from *Limulus polyphemus* Factor G-Subunit α

Using Peroxidase Labeling Kit-SH, and according to the method given in the manual attached to the kit, recombinant fragment-a/Cys derived from *Limulus polyphemus* factor G-subunit α obtained in the above (1) was labeled with peroxidase.

This labeled product was diluted 8000 times with 1% Blockace solution dissolved in 50 mM phosphate buffered saline containing casein (pH 7.5) and used for measurement.

(3) Preparation of Sample

"β-glucan standard" attached to β-Glucan test Wako which is a kit for βG measurement (produced by Wako Pure Chemical. Industries, Ltd.) was diluted with 0.5% serum albumen dissolved in 50 mM PBS (pH7.5) to give 1000 pg/mL in the reduced value of lentinan (described in the instruction attached to the "βG standard": 35 pg of indicated value corresponds to 1 ng of lentinan). And further diluted with 0.5% serum albumin dissolved in 50 mM phosphate buffered saline to give 0, 20, 50, 100, 250, 400, and 500 pg/mL in the reduced value of lentinan. These were used as a sample.

(4) Preparation of a Microplate for ELISA Immobilized with Fragment-b Derived from *Limulus Polyphemus* Factor G-Subunit α

The recombinant fragment-b derived from *Limulus polyphemus* factor G-subunit α obtained in Example 3 was adjusted with 50 mM MOPS buffer solution (pH 7.0) to 5 μg/mL, and 50 μL aliquot was dispensed in each well of microplate for ELISA, and by standing still at 10° C. for 16 hours, the fragment-b derived from *Limulus polyphemus* factor G-subunit α was immobilized to the aforementioned microplate.

Subsequently, as a blocking treatment for decreasing non-specific adsorption, 0.2 ml of 0.5% serum albumen dissolved in 50 mM phosphate buffered saline (pH 7.0) was added to each well; after standing still at room temperature for 1 hour, each well was washed.

(5) Sandwich Measurement

A 50 μL of sample having each lentinan concentration prepared in the above (3) was added to each well of the microplate prepared in the above (4), and reacted at 37° C. for 1 hour. Subsequently, each well was washed 3 times with PBS-T (produced by Wako Pure Chemical Industries, Ltd.). A 50 μL of peroxidase-labeled fragment-a derived from *Limulus polyphemus* factor G-subunit α prepared in the above (1) was added to each well, and reacted at 37° C. for 1 hour. Each well was washed 3 times with PBS-T, then once with distilled water. Subsequently, 50 μL of TMB solution (produced by Wako Pure Chemical Industries, Ltd.) was added to each well, and reacted at 25° C. for 30 minutes. Then, 50 μL of reaction terminating solution of the kit (1 M phosphoric acid solution) was added to each well to terminate the reaction. Absorbance at 450 nm was measured using Vmax (produced by Molecular Devices Inc.).

Based on the measurement value obtained, a standard curve was prepared by plotting absorbance at 450 nm (OD450 nm, y-axis) against lentinan concentration in the sample (reduced value, pg/mL, x-axis).

(6) Results

Figure 4:
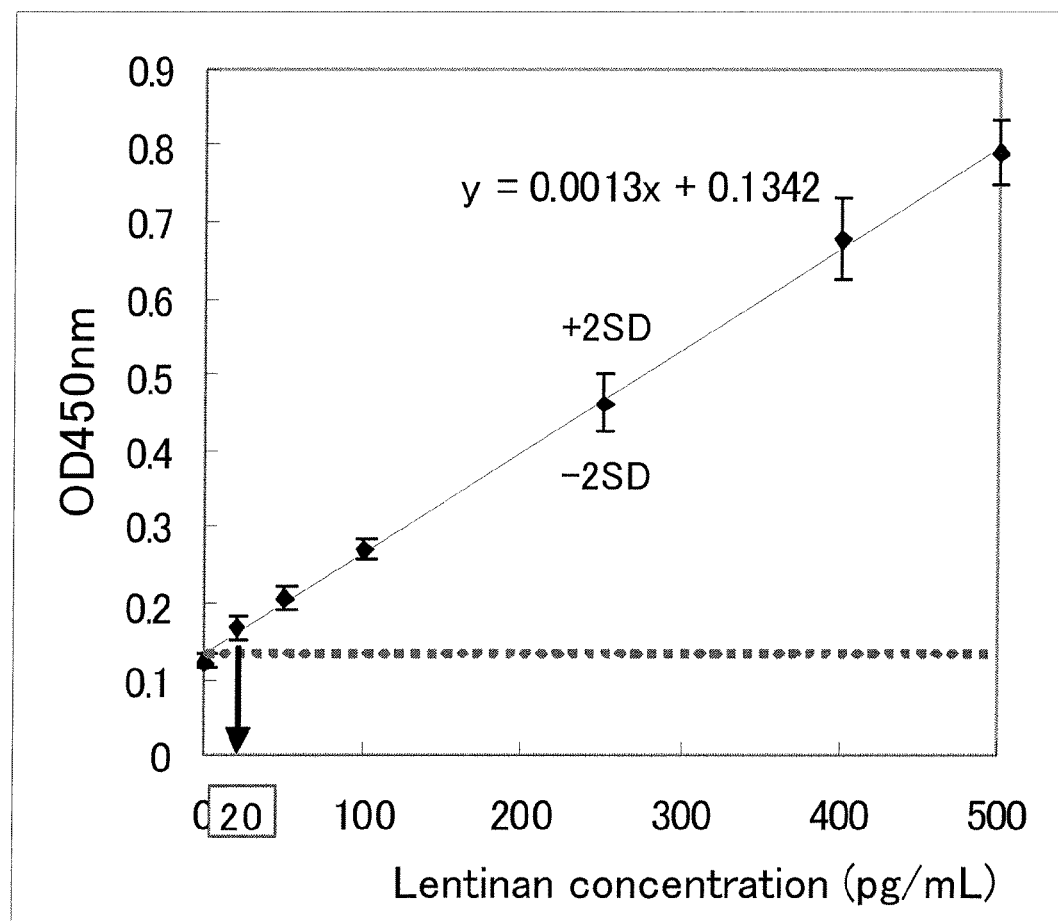
FIG. 4 is a standard curve obtained in Example 5, which shows the relationship between lentinan concentration (reduced value) in a sample and absorbance at 450 nm of the sample. Error bars indicate the value of 2SD.

The standard curve obtained is shown in FIG. 4. In FIG. 4, error bar shows a value of 2 SD.

In addition, regression line formula and correlation coefficient which were calculated by least-square method from the measurement values are as follows.

$y=0.0013x+0.1342$ $R^2=0.9989$

As is clear from FIG. 4, it turns out that when the measurement of βG is carried out using the βG-binding protein involved in the present invention, a favorable standard curve in which absorbance is proportional to the βG concentration (0 to 500 pg/mL in the reduced value of lentinan) in a sample can be obtained, and it can be used for the determination of βG Particularly, it was confirmed that of lentinan concentration could be detected significantly to 20 pg/mL of the lower limit. It should be noted that, the 20 pg/mL of lentinan concentration corresponds to 0.7 pg/mL of glucan in blood (cut-off value: 11 pg/mL or less) when the measurement is carried out by β-Glucan test Wako which is a kit for βG measurement.

Example 6

Confirmation of Peroxidase-Like Activity of the Fragment Derived from Horseshoe Crab Factor G-Subunit α

(1) βG-Binding Protein

The recombinant fragment-a derived from horseshoe crab factor G-subunit α obtained in Example 1, and the recombinant fragment-b derived from horseshoe crab factor G-subunit α obtained in Example 3 were used.

It should be noted that as described above, the fragment-a derived from *Limulus polyphemus* factor G-subunit α has an amino acid sequence of 233rd to 649th amino acid from N-terminal of *Limulus polyphemus* factor G-subunit α, and the fragment-b derived from *Limulus polyphemus* factor G-subunit α has an amino acid sequence of 387th to 649th amino acid from N-terminal of *Limulus polyphemus* factor G-subunit α. That is, the fragment-b derived from *Limulus polyphemus* factor G-subunit α lacks amino acid sequence of 233rd to 386th amino acid from N-terminal of *Limulus polyphemus* factor G-subunit α as compared with the fragment-a derived from *Limulus polyphemus* factor G-subunit α.

(2) Measurement of Peroxidase Activity

The βG-binding protein of the above described (1) was prepared to give 0, 3, 4, 5, 6, and 7 μg/mL with 50 mM MOPS buffer solution (pH 7.0), and a 50 μL was placed in each well of the microplate for ELISA. By standing still at 10° C. for 16 hours, each βG-binding protein was immobilized to the microplate.

Subsequently, as a blocking operation for reducing non-specific adsorption, 0.2 mL aliquot of 1% Blockace solution or 0.1% serum albumin dissolved in 50 mM phosphate buffered saline (pH 7.0) was dispensed in each well, and after standing still at room temperature for 1 hour, each well was washed.

Subsequently, 50 μL of TMB solution (produced by Wako Pure Chemical Industries, Ltd.) was added to each well, and reacted at 25° C. for 30 minutes. Then, 50 μL of reaction terminating solution (1 M phosphoric acid solution) was added to each well to terminate the reaction. Absorbance at 450 nm was measured using Vmax (produced by Molecular Devices Inc.).

It should be noted that using a sample of only 0.1% serum albumin instead of βG-binding protein, similar measurement was carried out to use as a blank value.

(3) Results

Figure 5:
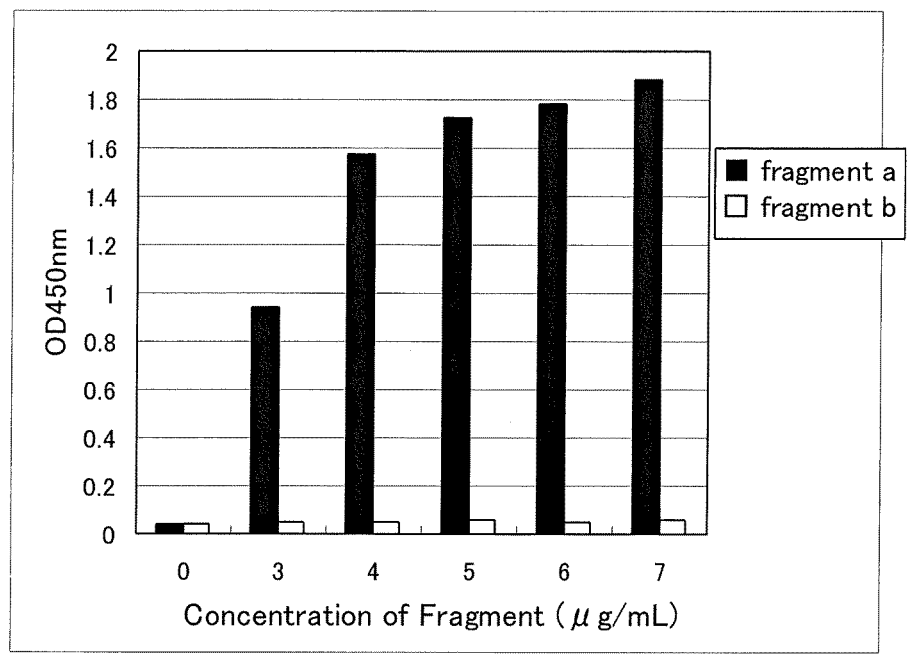
FIG. 5 shows the results of measurement for peroxidase activity in each concentration of the fragment-a derived from *Limulus polyphemus* factor G-subunit α and the fragment-b derived from *Limulus polyphemus* factor G-subunit α obtained in Example 6.

Obtained results are shown in FIG. 5. In FIG. 5, each bar shows a result obtained when the following βG-binding proteins were used.

Fragment-a derived from *Limulus polyphemus* factor G-subunit α
Fragment-b derived from *Limulus polyphemus* factor G-subunit α

As is clear from FIG. 5, the fragment-b derived from *Limulus polyphemus* factor G-subunit α did not show any peroxidase activity within the concentration range of 0, 3, 4, 5, 6, and 7 μg/mL. On the other hand, as for the fragment-a derived from *Limulus polyphemus* factor G-subunit α, peroxidase activity dependent on the fragment concentration was confirmed within the concentration range of 0, 3, 4, 5, 6, and 7 μg/mL.

From the results mentioned above, it is considered that the amino acid sequence of 233rd to 386th from N-terminal of the fragment derived from *Limulus polyphemus* factor G-subunit α is essential for having peroxidase activity.

Example 7

Participation of Metal Ion to the Peroxidase Activity of the Fragment-a Derived from *Limulus polyphemus* Factor G-Subunit α

(1) Measurement of Peroxidase Activity

Into a 10 μg/mL solution (50 mM MOPS buffer solution (pH7.0)) of the recombinant fragment-a derived from *Limulus polyphemus* factor G-subunit α, disodium ethylenediaminetetraacetate (EDTA) or NaN$_3$ was mixed to give final concentration of 70 m or 0.05%, respectively, and the mixture was incubated at 25° C. for 1 hour. As a reference, a 10 μg/mL solution of fragment-a derived from *Limulus polyphemus* factor G-subunit α which does not contain these metal-chelating agents was prepared.

Subsequently, each solution after incubation was prepared to give 5 μg/mL solution of fragment-a derived from *Limulus polyphemus* factor G-subunit α with 50 mM MOPS buffer solution (pH7.0), and 50 μL aliquot was placed in each well of the microplate for ELISA, and immobilized by standing still at 10° C. for 12 hours to 20 hours. As a blocking operation for reducing nonspecific adsorption, 0.2 mL aliquot of 1% Blockace solution or 0.1% serum albumin dissolved in 50 mM phosphate buffered saline (pH 7.0) was dispensed in each well, and after standing still at room temperature for 1 hour, each well was washed.

A 50 μL aliquot of TMB solution (produced by Wako Pure Chemical Industries, Ltd.) was added to each well, and reacted at 25° C. for 30 minutes. Then, 50 μL of reaction terminating solution (1 M phosphoric acid solution) was added to each well, and absorbance at 450 nm wave length was measured using Vmax (produced by Molecular Devices Inc.).

(2) Results

Figure 6:
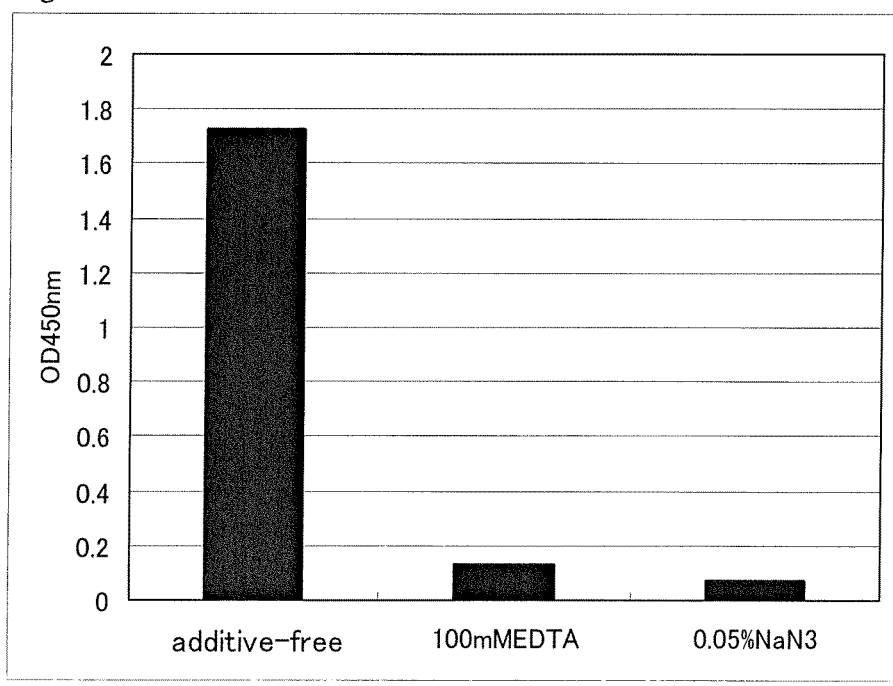
FIG. 6 shows the results of measurement under the presence or absence of a metal chelating agent for peroxidase activity of the fragment-a derived from *Limulus polyphemus* factor G-subunit α obtained in Example 7.

Obtained results are shown in FIG. 6.

As is clear from FIG. 6, as to the fragment-a derived from *Limulus polyphemus* factor G-subunit α, it was confirmed that the peroxidase activity of the fragment-a derived from *Limulus polyphemus* factor G-subunit α was lost when EDTA or NaN$_3$ which was a metal-chelating agent existed. In consequent, it is conceivable that in order for *Limulus polyphemus* factor G to exert peroxidase activity, metal ion may be involved.

Example 8

Sandwich Measurement Using Fragment Derived from Horseshoe Crab Factor G-Subunit α (4)

(1) Preparation of Fragment-a/Cys Derived from *Limulus polyphemus* Factor G-Subunit α

Fragment-a/Cys derived from *Limulus polyphemus* factor G-subunit α in which one residue of cysteine was introduced into N-terminal of the fragment-a derived from *Limulus polyphemus* factor G-subunit α was designed. Subsequently, fragment-a/Cys derived from *Limulus polyphemus* factor G-subunit α was expressed and purified by carrying out the same method as in Example 1 (6) to (8) except for using a primer having a nucleotide sequence shown in SEQ ID NO: 46 (5'-tgtctggattaagattacaaagg-3') as primer F, and a primer having a nucleotide sequence shown in SEQ ID NO: 24 as primer R (primer F and primer R were synthesized by Sigma-Aldrich Corp. on consignment).

(2) DNA Labeling of Fragment-a Derived from *Limulus polyphemus* Factor G-Subunit α

(i) Preparation of 250 bp DNA Fragment for Labeling

Primer 1 (5'-gcctagcaaactcggaagatt-3', SEQ ID NO: 47) and primer 2 in which C6 amino linker (produced by Sigma-Aldrich Corporation) had been introduced into 5'-terminal in advance (nucleotide sequence: 5'-atctatgactgtacgccaatgtc-cctag-3', SEQ ID NO: 48) were synthesized by Sigma-Aldrich Corp. on consignment. Using this primer pair and using λDNA (produced by Nippon Gene Co., Ltd.) as a template, PCR was carried out, and the 250 bp DNA having C6 amino linker on the other end was prepared. This PCR product was purified by DEAE ion-exchange chromatography and isopropanol precipitation, the 250 bp DNA fragment for labeling was obtained.

(ii) Binding of 250 bp DNA Fragment to the Fragment-a Derived from *Limulus polyphemus* Factor G-Subunit α

After reacting NH$_2$ group of C6 amino linker introduced into the DNA fragment with N-(ε-maleimidocaproyloxy)succinimide ester (EMCS) linker (produced by Thermo Fisher Scientific Inc.) by the method given in the direction attached to EMCS, unreacted EMCS linker was removed by gel filtration treatment, and the DNA fragment bound with EMCS linker was obtained. This EMCS linker-attached DNA fragment and the fragment-a of the above (1) were reacted by the method given in the direction attached to EMCS. The obtained reaction product was purified by DEAF ion-exchange chromatography and gel filtration chromatography, DNA-labeled fragment-a derived from *Limulus polyphemus* factor G-subunit α was obtained.

(3) Fluorescent Labeling of Fragments-a/Cys Derived from *Limulus polyphemus* Factor G-Subunit α

Using HiLyte Fluor 647 C2 maleimide (produced by AnaSpec Inc.) and according to the method described in the manual attached, the fragment-a/Cys obtained in the above (1) was fluorescently labeled with HiLyte Fluor 647.

(4) Preparation of βG Sample

"β-Glucan standard" attached to β-Glucan test Wako which is a kit for βG measurement (produced by Wako Pure Chemical. Industries, Ltd.) was dissolved in the standard β-glucan dissolving solution attached to the kit to prepare a standard solution (stock solution). Further, the stock solution was diluted with the standard β-glucan dissolving solution attached to the kit to provide 0, 25, 50, 100, 200, 400, and 800 pg/mL in the reduced value of lentinan. These were used as a sample.

(5) Sandwich Measurement by Capillary Electrophoresis

1) Capillary Chip

A capillary chip having a layout shown in FIG. 7 was prepared as follows according to the method described in "Micro Chemical. Chip Technology and Applications", pp. 185-217 [Takehiko Kitamori, et al., published 2004 (Maruzen Co., Ltd.)].

That is, a photoresist film was formed on a Si coated quartz plate. This photoresist was exposed through a mask which has a capillary design (layout) shown in FIG. 7, and developed. After removing Si of the part where photoresist was removed by development by sputter, capillary channel (tubule) was made on the quartz plate by carrying out wet etching using hydrofluoric acid solution. After removing the photoresist and Si film which remain on the quartz plate, the aforementioned quartz plate and a cover plate which has holes for introducing or discharging various reagents into/from various wells were pasted together by HF connection method to prepare the capillary chip.

Figure 7:
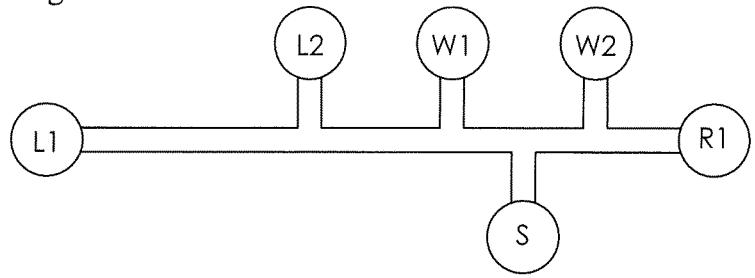
FIG. 7 shows the layout of the capillary chip used in Example 8.

It should be noted that in FIG. 7, L1 and L2 indicate wells for introducing leading buffer; R1 indicates well for introducing trailing buffer; S indicates well for introducing sample for electrophoresis; and W1 and W2 indicate wells for drain, respectively. Moreover, in the figure, the distance between L1 to R1 is 6.3 cm, and L1 to L2 is 2.8 cm.

2) Sample for Electrophoresis

Using DNA-labeled fragment-a/Cys derived from *Limulus polyphemus* factor G-subunit α obtained in the above (2) and fluorescently-labeled fragment-a/Cys derived from *Limulus polyphemus* factor G-subunit α obtained in the above item (3), reagent solution for reaction of the following composition was prepared.

25 nM DNA labeled fragment-a/Cys derived from *Limulus polyphemus* factor G-subunit α;
6 nM fluorescently-labeled fragment-a/Cys derived from *Limulus polyphemus* factor G-subunit α;
150 mM BisTris;
100 mM magnesium chloride;
0.56% pDMA22 (poly(N,N-dimethylacrylamide));
3.33% glycerol;
0.056% Tween20;
0.01% BSA;
1% lithium heparin.
pH was adjusted to 7.0.

A 45 μL of this reagent solution for reaction and 5 μL of βG sample prepared in the above (4) were mixed at room temperature for 1 minute, and thereby the βG in the sample and the DNA-labeled fragment-a/Cys derived from *Limulus polyphemus* factor G-subunit α and fluorescently-labeled fragment-a/Cys derived from *Limulus polyphemus* factor G-subunit α were reacted to use as a sample for electrophoresis.

3) Reagents for Electrophoresis a) Trailing buffer: 125 mM HEPES containing 75 mM Tris base, 0.5% pDMA 22, 3% Glycerol, 0.05% Tween 20, and 0.01% BSA;

b) Leading buffer: 75 mM Tris-HCl (pH 8.0) containing 50 mM NaCl, 0.5% pDMA22, 3% Glycerol, 0.05% Tween20, 0.01% BSA, and 1% Heparin Li.

4) Introduction of Sample for Electrophoresis and Reagent Solution

In FIG. 7, 10 μL of sample for electrophoresis obtained in the above 2) was dripped into well S (a well for introducing sample for electrophoresis), 10 μL of trailing buffer into well R1 (a well for introducing reagent solution), 10 μL of leading buffer into well L1 and well L2, respectively; then the sample for electrophoresis and leading buffer were introduced into the channel by applying −5 psi in between well W1 (a well for drain) and well W2 (a well for drain) for 100 seconds.

5) Concentration/Separation/Detection

A voltage of 2500V was applied between well R1-well L1 in FIG. 7, and electrophoresis was carried out in the R1→L1 direction at 30° C., while the sample was condensed. By monitoring the voltage between well L1-well L2, passage over the joining point of channel L2 and main channel was checked. At the time of passage, by applying a voltage of 1500V between well L2 and well L1 for 120 seconds, electrophoresis was run in the direction of well L2→well L1, unreacted fluorescently-labeled fragment-a/Cys derived from *Limulus polyphemus* factor G-subunit α in the aforementioned sample, and a complex formed by βG in the sample, DNA-labeled product of fragment-a/Cys derived from *Limulus polyphemus* factor G-subunit α and fluorescently-labeled fragment-a/Cys derived from *Limulus polyphemus* factor G-subunit α were separated, and amount of the aforementioned complex was detected.

It should be noted that the detection was carried out by measuring fluorescence intensity with time by laser excitation at 650 nm using a fluorescence microscope (BX-50; produced by KS Olympus Co., Ltd.) at a capillary section apart by 2 cm from the joining point of L2 towards L1.

Based on the results, a standard curve, which was made by plotting a time-integrated value of the fluorescence intensity of the aforementioned complex (a value which was obtained by monitoring the fluorescence intensity and integrating the intensity of the corresponding peak for time, y-axis) versus a lentinan concentration in the sample (a reduced value, pg/mL, x-axis), was prepared.

(6) Results

Figure 8:
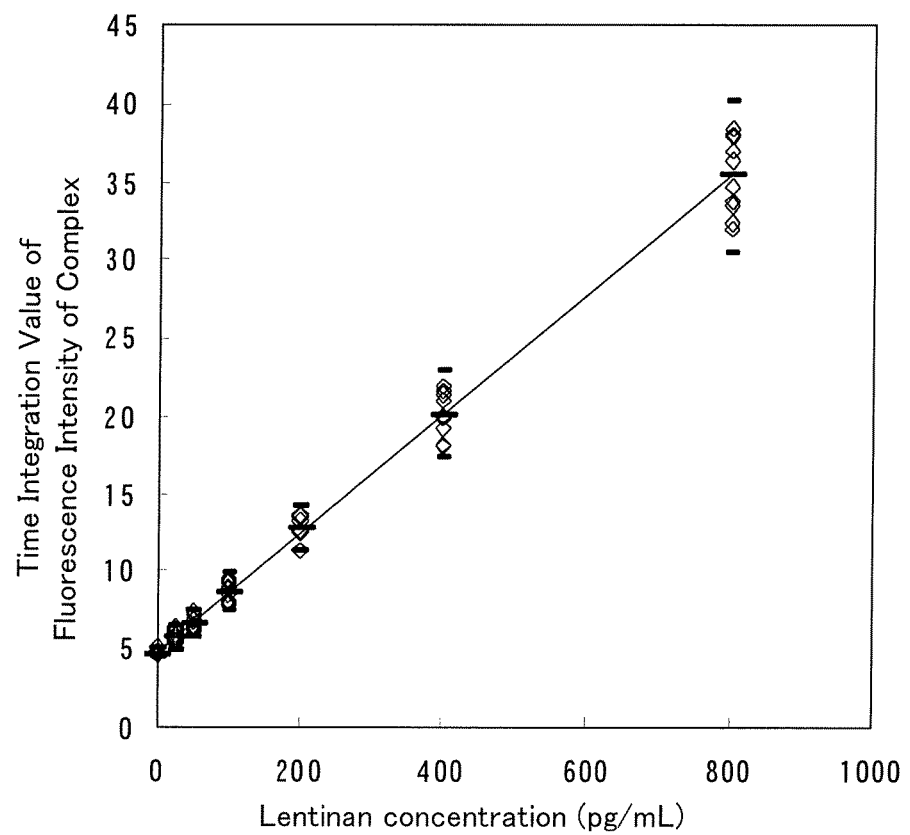
FIG. 8 shows a standard curve obtained in Example 6, which shows the relationship between lentinan concentration (reduced value) in a sample and time integration value of fluorescence intensity of the complex. Error bars indicate the value of 2SD.

The standard curve obtained is shown in FIG. 8. In FIG. 8, the error bar shows 2SD.

In addition, regression line formula and correlation coefficient which were calculated by the least-square method from the measurement values are as follows.

$$y=0.0370x+5.1$$

$$R^2=0.9999$$

As is clear from FIG. 8, it turns out that when the measurement of βG is carried out using the βG-binding protein involved in the present invention, a favorable standard curve is proportional to the βG concentration (0 to 800 pg/mL in the reduced value of lentinan) in a sample can be obtained and it can be used for the measurement of βG Particularly, it was confirmed that the concentration could be detected significantly to the lower limit of 50 pg/mL in lentinan concentration. It should be noted that the 50 pg/mL in lentinan concentration corresponds to 1.75 pg/mL of glucan in blood (cutoff value: 11 pg/mL) when the measurement is performed using β-Glucan test Wako which is a kit for βG measurement.

Example 9

Sandwich Measurement Using Fragment Derived from Horseshoe Crab Factor G-Subunit α (5)

(1) Fragment-a/Cys derived from *Limulus polyphemus* factor G-subunit α

The recombinant fragment-a/Cys derived from *Limulus polyphemus* factor G-subunit α obtained in Example 8 was used.

(2) Peroxidases labeling of fragment-a/Cys derived from *Limulus polyphemus* factor G-subunit α

Using Peroxidase Labeling Kit-SH, and according to the method given in the manual attached to the kit, recombinant fragment-a/Cys derived from *Limulus polyphemus* factor G-subunit α of the above (1) was labeled with peroxidase.

This labeled-product was diluted 8000 times with 1% Blockace solution dissolved in 50 mM phosphate buffered saline containing casein (pH 7.5) and used for measurement.

(3) Preparation of Plasma Sample

Humans plasma was diluted 10 times with 50 mM PBS (pH 7.5, containing 0.5% serum albumin), and one-half of the solution was subjected to heat treatment on a hot water bath at 70° C. for 10 minutes (pretreatment). The pretreated plasma and the plasma which was not pretreated were used as a plasma sample, respectively.

(4) Preparation of a Microplate for ELISA Immobilized with Fragment-a Derived from *Limulus polyphemus* Factor G-Subunit α

The recombinant fragment-a derived from *Limulus polyphemus* factor G-subunit α obtained in Example 1 was adjusted with 50 mM MOPS buffer solution (pH 7.0) to 5 μg/mL, and 50 μL aliquot was dispensed in each well of microplate for ELISA, and by standing still at 10° C. for 16 hours, the fragment-a derived from *Limulus polyphemus* factor G-subunit α was immobilized to the aforementioned microplate.

Subsequently, as a blocking treatment for decreasing non-specific adsorption, 0.2 ml of 0.5% serum albumen dissolved in 50 mM phosphate buffered saline (pH 7.0) was added to each well; after standing still at room temperature for 1 hour, each well was washed.

(5) Sandwich Measurement

A 50 μL of plasma sample prepared in the above (3) was added to each well of the microplate prepared in the above (4), and reacted at 37° C. for 1 hour. Subsequently, each well was washed 3 times with PBS-T (produced by Wako Pure Chemical Industries, Ltd.). A 50 μL of peroxidase-labeled fragment-a derived from *Limulus polyphemus* factor G-subunit α prepared in the above (1) was added to each well, and reacted at 37° C. for 1 hour. Each well was washed 3 times with PBS-T, then once with distilled water. Subsequently, 50 μL of TMB solution (produced by Wako Pure Chemical Industries, Ltd.) was added to each well, and reacted at 25° C. for 30 minutes. Then, 50 μL of reaction terminating solution of the kit (1 M phosphoric acid solution) was added to each well to terminate the reaction. Absorbance at 450 nm was measured using Vmax (produced by Molecular Devices Inc.).

Aside from this, as for β-glucan standard, similar measurement was carried out using samples prepared by the method of Example 5 (3), a standard curve was prepared.

By fitting the absorbance value obtained with using the plasma sample to the aforementioned standard curve, amount of βG in the plasma sample was calculated.

It should be noted that an addition-recovery test by a routine procedure was carried out to confirm performance of the measurement method of the present invention. That is, using a plasma sample which is a βG-negative plasma added with a certain amount of βG, measurement of βG by the method of the present Example was carried out. As a result, addition-recovery rate was 72.8% to 93.9%, showing good recovery rate.

In addition, it was confirmed that the βG measurement method by the method of the present Example was not influenced by the heparin contained in the plasma.

(6) Results

Obtained results are shown in Table 12.

Comparative Example 1

(1) Plasma Sample

The pretreated plasma sample used in Example 9 was used.

(2) Measurement of βG Concentration

Using commercially available β-Glucan test Wako which is a kit for βG measurement (produced by Wako Pure Chemical Industries, Ltd.), βG concentration of plasma sample of the above (1) was measured according to the operation method described in a pamphlet attached to the aforementioned kit, and according to a common procedure of turbidimetric kinetic method, βG was measured as follows.

That is, 200 μL of pretreated plasma sample was added to *Limulus* reagent of the kit (lyophilized product: containing *Limulus* hemocyte extract (AL)). After agitating for several seconds using vortex mixer, a time required for transmitted light intensity through the aforementioned mixed solution to decrease by 5% from start of the measurement (hereinafter, abbreviated as Tg) was measured under warming at 37° C. using Toxinometer MT-5500 (produced by Wako Pure Chemical Industries, Ltd.). Aside from this, the same measurement was carried out using distilled water and βG solution of known concentration, and a standard curve showing a relationship between βG concentration and Tg was prepared. The concentration of βG in the sample was calculated based on this standard curve.

(3) Results

Obtained results are shown collectively in Table 12.

TABLE 12

| | βG concentration (pg/mL) | | |
|---|---|---|---|
| | Example 9 | | Comparative Example 1 |
| | Pretreated | Not pretreated | Pretreated |
| Plasma sample 1 | Below detection limit | Below detection limit | Below detection limit |
| Plasma sample 2 | Below detection limit | Below detection limit | Below detection limit |
| Plasma sample 3 | 126.1 | 129.6 | 174.5 |
| Plasma sample 4 | 288.1 | 287.6 | 300.1 |

The conventional method for measuring βG using hemocyte extract of horseshoe crab is a method using protease cascade, however, the cascade is inhibited by proteases contained in a blood sample. Therefore, in order to measure βG by the conventional method using hemocyte extract of horseshoe crab, a pretreatment in which the enzyme in the blood sample is deactivated in advance by heat-treatment of the blood sample is indispensable.

In Example 9, βG concentration in the pretreated and not pretreated plasma samples were measured by the sandwich ELISA method of the present invention. As a result, as is clear from Table 12, the βG concentrations measured using the plasma sample which was not pretreated were close to the βG concentrations measured using the pretreated plasma sample. In addition, the values were also close to the βG concentrations obtained by measuring the βG concentrations in the pretreated plasma sample by the conventional measurement method using hemocyte extract of horseshoe crab (Comparative Example 1). From the fact mentioned above, it turns out that if the method for measuring βG of the present invention is carried out, βG can be measured without retreating a sample. Moreover, the above results suggest that the method for measuring βG of the present invention can be a new detection system for detecting βG in a clinical sample.

Example 10

Correlation of the Plasma βG Value Between the Sandwich Measurement Method of the Present Invention and the Conventional Measurement Method Using Hemocyte Extract of Horseshoe Crab (1) Sandwich Measurement of the Present Invention
1) Peroxidase-Labeled Fragment-a/Cys Derived from *Limulus polyphemus* Factor G-Subunit α

The peroxidase-labeled fragment-a/Cys derived from *Limulus polyphemus* factor G-subunit α prepared in Example 9 was used.

2) Preparation of a Microplate for ELISA Immobilized with Fragment-a Derived from *Limulus polyphemus* Factor G-Subunit α

The microplate for ELISA immobilized with fragment-a derived from *Limulus polyphemus* factor G-subunit α prepared in Example 9 was used.

3) Preparation of Plasma Sample

The human plasma (N=50) in which the βG concentration had been confirmed to be below a cutoff value by the measurement using a commercially available β-Glucan test Wako (Wako Pure Chemical Industries, Ltd.) and pretreated by the same method as in Example 9 was used as a plasma sample.

4) Sandwich Measurement

Using the same equipment as used in Example 9, and by carrying out measurement under the same measurement conditions, the βG concentration in a plasma sample was calculated.

(2) Measurement Using Hemocyte Extract of Horseshoe Crab (Turbidimetric Kinetic Method)

Figure 9:
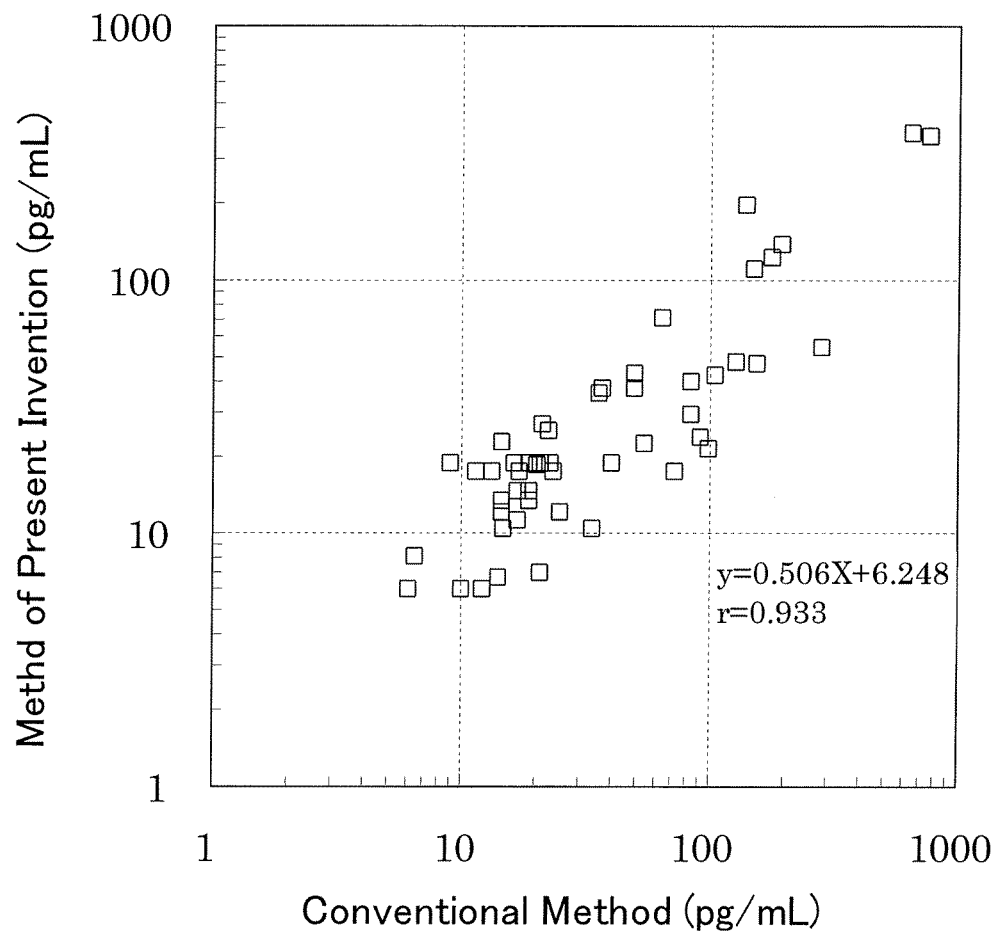
FIG. 9 shows a correlation between the βG concentrations obtained by the sandwich method of the present invention and the βG concentrations obtained by the conventional measurement method employing hemocyte extract of horseshoe crab, which was obtained in Example 10.

The βG concentration in a plasma sample was calculated in the same manner as in Comparative Example 1, except for using the same sample as used in the above (1) 3) as a plasma sample, (3) Results A correlation diagram between the βG concentration obtained by the sandwich measurement method of the present invention (the method for measuring βG of the present invention) and the βG concentration obtained using a commercially available kit of the conventional measurement method using hemocyte extract of horseshoe crab (the conventional measurement method) are shown in FIG. 9.

The regression line formula and correlation coefficient which were obtained by performing regression analysis for the results of FIG. 9 are as follows.

$$y=0.506x+6.248;$$

$$R=0.933.$$

As is clear from the results mentioned above, it turns out that the βG concentrations obtained by the method for measuring βG of the present invention show a good correlation with the βG concentrations obtained by the conventional measurement method using hemocyte extract of horseshoe crab. The above results suggest that the method for measuring βG of the present invention can be a new detection system for detecting βG in a clinical sample.

Example 11

Sandwich Measurement Using the Fragment Derived from *Limulus polyphemus* Factor G-Subunit α (6)

(1) Peroxidase-Labeled Fragment-a/Cys Derived from *Limulus polyphemus* Factor G-Subunit α

The peroxidase-labeled fragment-a/Cys derived from *Limulus polyphemus* factor G-subunit α prepared in Example 9 was used.

(2) a Microplate for ELISA Immobilized with Fragment-b Derived from *Limulus polyphemus* Factor G-Subunit α

The microplate for ELISA immobilized with fragment-b derived from *Limulus polyphemus* factor G-subunit α prepared in Example 5 (4) was used.

(3) Preparation of βG Sample

"β-Glucan standard" attached to β-Glucan test Wako which was a kit for βG measurement (produced by Wako Pure Chemical. Industries, Ltd.) was dissolved in standard β-glucan dissolving solution attached to the kit to prepare a standard solution (stock solution). Further, the stock solution was diluted with the standard β-glucan dissolving solution attached to the kit to provide 0, 1, 5, 10, 17, 50, and 100 pg/mL in the reduced value of lentinan. These were used as a sample.

(4) Sandwich Measurement

A 50 μL of sample prepared in the above (3) was added to each well of the microplate of the above (2), and reacted at 37° C. for 1 hour. Subsequently, each well was washed 3 times with PBS-T (produced by Wako Pure Chemical Industries, Ltd.). A 50 μL of peroxidase labeled fragment-a/Cys derived from *Limulus polyphemus* factor G-subunit α of the above (1) was added to each well, and reacted at 37° C. for 1 hour. Each well was washed 3 times with PBS-T, then once with distilled water. Subsequently, Super Signal ELISA Feta Maximum Sensitivity Substrate (produced by Thermo Fisher Scientific Inc.) was added thereto, and reacted according to the instruction for use attached to the kit.

Amount of luminescence (cps, count per second) was measured using Ultra Evolution (made by TECAN Group Ltd.).

(5) Results

Figure 10:
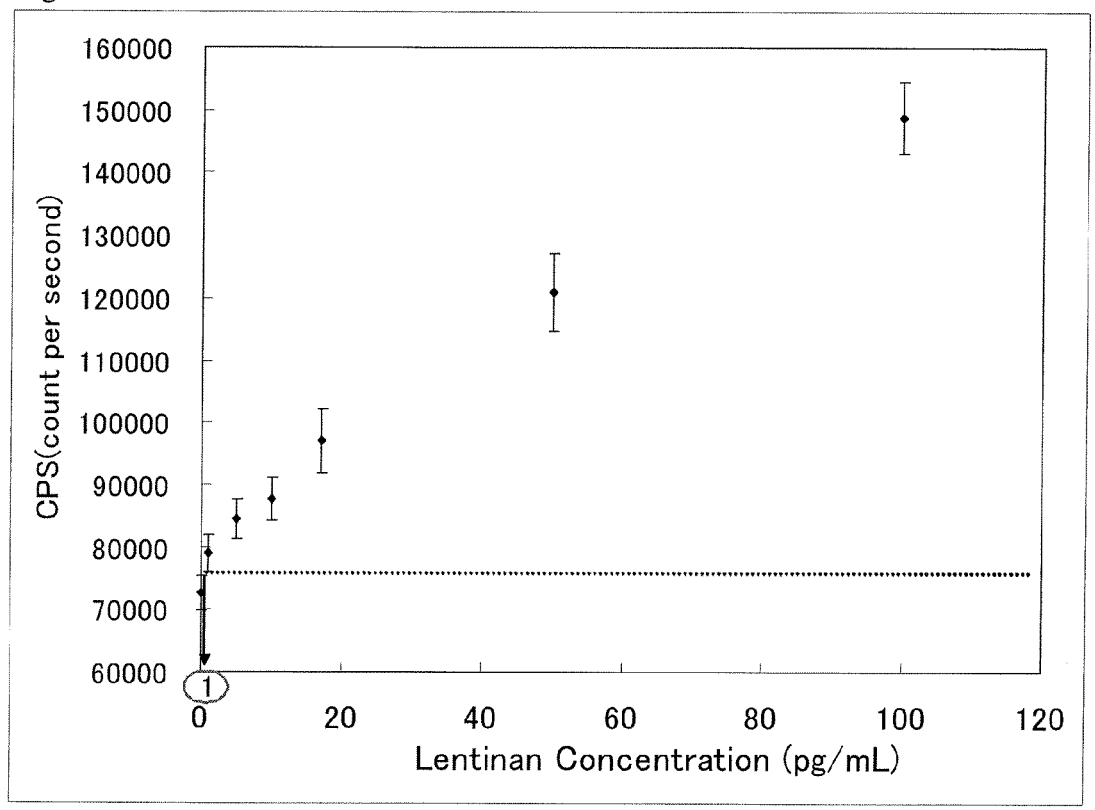
FIG. 10 shows a relationship between lentinan concentration (reduced value) in a sample and luminescence intensity (cps: count per second), which was obtained in Example 11. Error bars indicate the value of 1SD.

Results are shown in FIG. 10. In FIG. 10, error bar shows a value of 1 SD.

As is clear from FIG. 10, it was confirmed that when measurement of βG was carried out by measuring fluorescence using the βG-binding protein involved in the present invention, βG could be detected significantly to the lower limit of 1 pg/mL in lentinan concentration.

Moreover, the cutoff value of glucan in blood is 11 pg/mL when the measurement is performed by β-Glucan test Wako which is a commercially available kit for βG measurement. It is known that lentinan 1 pg is equivalent to glucan 0.035 pg. In the present Example, it turned out that the lower limit of detectable lentinan concentration was 1 pg/mL, and even if dilution rate of sample was taken into consideration, concentration lower than the cutoff value of the commercial kit for βG measurement can be measured, that is, βG can be measured in extremely high sensitivity.

This is considered that similarly to the case of Example 4, by carrying out the peroxidase labeling of the fragment-a in which Cys is introduced, a distance is generated between the peroxidase attached to the fragment-a and βG binding site in the fragment-a, and thereby the peroxidase becomes not to interfere the binding of fragment and βG, and measurement of βG can be performed with sufficient sensitivity.

Industrial Applicability

The method for measuring βG of the present invention can utilize a recombinant βG-binding protein and needs not to use natural materials. Therefore, the method does not have lot difference caused by reagent, and exerts an effect that a specific measurement of βG can be performed with a constant and yet high measurement sensitivity.

Description Of Symbols

L1, L2: well for leading buffer introduction;

R1: well for trailing buffer introduction;

S: well for introducing sample for electrophoresis;

W1, W2: well for drain

What is claimed is:

1. A method for measuring β-glucan (hereinafter, abbreviated as "βG"), which comprises:
   (1) contacting a sample with
      protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity (hereinafter, abbreviated as "βG-binding protein 1"), and
      protein 2 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, having a β-glucan binding activity (hereinafter, abbreviated as "βG-binding protein 2"), to form a complex of the βG-binding protein 1, βG in the sample and the βG-binding protein 2,
      wherein the βG-binding protein 2 is labeled with a labeling substance;
   (2) measuring a quantity of the labeling substance in the complex; and
   (3) determining a βG concentration in the sample based on the quantity measured in (2).

2. The method of measurement according to claim 1, wherein the βG-binding protein 1 is immobilized to an insoluble carrier.

3. The method of measurement according to claim 1, wherein each of the βG-binding protein 1 and the βG-binding protein 2 is labeled with a labeling substances that is different from one another.

4. The method of measurement according to claim 1, wherein the measurement comprises:
   (1) contacting a sample with the βG-binding protein 1 to form a complex-1 of βG in the sample and the βG-binding protein 1;
   (2) contacting the complex-1 with the βG-binding protein 2 which is labeled with a labeling substance, to form a complex-2 of the βG-binding protein 1, βG in the sample and the βG-binding protein 2;
   (3) measuring quantity of the labeling substance in the complex-2; and
   (4) determining a βG concentration in the sample based on the quantity of the complex-2 obtained.

5. The method of measurement according to claim 1, wherein the measurement comprises:
   (1) contacting a sample with βG-binding protein 1 which is immobilized to an insoluble carrier, to form a complex-1 of βG in the sample and the βG-binding protein 1 immobilized to the insoluble carrier;
   (2) contacting the complex-1 with the βG-binding protein 2 which is labeled with a labeling substance, to form a complex-2 of the complex-1 and the labeled βG-binding protein 2;
   (3) measuring quantity of the labeling substance in the complex-2; and
   (4) determining βG concentration in the sample based on the quantity obtained.

6. The method of measurement according to claim 1, wherein the βG-binding protein 1 and the βG-binding protein 2 are used without being immobilized to an insoluble carrier.

7. The method of measurement according to claim 6, wherein after the complex is formed, the complex is separated from free βG-binding protein 1 and free βG-binding protein 2 by capillary electrophoresis.

8. A kit for measuring β-glucan comprising the followings as constituents:
   (1) a reagent containing a protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any of the SEQ ID NO: 4, SEQ ID NO: 6, SEQ ID NO: 8 and SEQ ID NO: 10, and having a β-glucan binding activity (hereinafter, abbreviated as "βG-binding protein 1"); and (2) a reagent containing a protein 2 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of the SEQ ID NO: 4, SEQ ID NO: 6, SEQ ID NO: 8, and SEQ ID NO: 10, and having a β-glucan binding activity. (hereinafter, abbreviated as "βG-binding protein 2"), wherein the βG-binding protein 2 is labeled with a labeling substance.

9. The kit according to claim 8, wherein the βG-binding protein 1 is immobilized to an insoluble carrier.

10. The kit according to claim 8, wherein each of the βG-binding protein 1 and the βG-binding protein 2 is labeled with a labeling substance that is different from one another.

11. An isolated protein comprising an amino acid sequence identical to an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity.

12. A method for measuring βG comprising:
(1) contacting a sample with
βG-binding protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity (hereinafter, abbreviated as "βG-binding protein 1"), wherein the βG-binding protein 1 is immobilized to an insoluble carrier, and
βG-binding protein 2 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity (hereinafter, abbreviated as "βG-binding protein 2"), to form a complex of the βG-binding protein 1, βG in the sample and the βG-binding protein 2,
(2) measuring a quantity of the complex by a turbidimetric method, a nephelometric method, or a latex aggregation method; and
(3) determining a βG concentration in the sample based on the quantity measured in (2).

13. A method for measuring βG comprising:
(1) contacting a sample with
βG-binding protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity, and
βG-binding protein 2 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity, to form a complex of the βG-binding protein 1, βG in the sample and the βG-binding protein 2,
wherein the βG-binding protein 1 and βG-binding protein 2 are different each other, and
wherein at least one of the βG-binding protein 1 and the βG-binding protein 2 comprises an amino acid sequence shown in SEQ ID NO: 4 or SEQ ID NO: 10, or an amino acid sequence having 95% or more of homology to the amino acid sequence shown in SEQ ID NO: 4, or SEQ ID NO: 10, and having a β-glucan binding activity and peroxidase activity;
(2) measuring quantity of the complex by measuring a peroxidase activity derived from the βG-binding protein 1 and/or βG-binding protein 2; and
(3) determining a βG concentration in the sample based on the quantity.

14. The method of measurement according to claim 1, wherein the βG-binding protein 1 is not immobilized to an insoluble carrier, and is not labeled with a labeling substance.

15. The kit according to claim 8, wherein the βG-binding protein 1 and the βG-binding protein 2 are not immobilized to an insoluble carrier.

16. A kit for measuring β-glucan comprising the followings as constituents:
(1) a reagent containing a protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8m, and SEQ ID NO: 10, and having a β-glucan binding activity, wherein the βG-binding protein 1 is immobilized to an insoluble carrier, and
(2) a reagent containing a protein 2 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity.

17. A kit for measuring βG comprising the followings as constituents:
(1) a reagent contacting a protein 1 comprising an amino acid sequence shown in any one of SEQ ID NO: 4, SEQ ID NO: 6, SEQ ID NO: 8, and SEQ ID NO: 10, or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity, and
(2) a reagent containing a protein 2 comprising an amino acid sequence shown in any one of SEQ ID NO: 4, SEQ ID NO: 6, SEQ ID NO: 8, and SEQ ID NO: 10,or an amino acid sequence having 95% or more of homology to the amino acid sequence shown in any one of SEQ ID NO: 4, SEQ ID NO: 6, SEQ ID NO: 8, and SEQ ID NO: 10, and having a β-glucan binding activity,
wherein the βG-binding protein 1 and βG-binding protein 2 are different each other, and
wherein at least one of the βG-binding protein 1 and the βG-binding protein 2 comprises an amino acid sequence shown in SEQ ID NO: 4 or SEQ ID NO: 10, or an amino acid sequence having 95% or more of homology to the amino acid sequence shown in SEQ ID NO: 4, or SEQ ID NO: 10, and having a β-glucan binding activity and peroxidase activity.

18. The kit according to claim 8, wherein the βG-binding protein 1 is not immobilized to an insoluble carrier, and is not lableled with a labeling substance.

* * * * *

SEQUENCE LISTING

<160> NUMBER OF SEQ ID NOS: 48

<210> SEQ ID NO 1
<211> LENGTH: 1947
<212> TYPE: DNA
<213> ORGANISM: Limulus sp.
<220> FEATURE:
<221> NAME/KEY: CDS
<222> LOCATION: (1)..(1947)

<400> SEQUENCE: 1

| | | | | | | | | | | | | | | | | |
|---|---|---|---|---|---|---|---|---|---|---|---|---|---|---|---|---|
| agc | cag | gaa | cca | aaa | tgg | aag | ctc | gtc | tgg | tcg | gat | gaa | ttt | acc | aat | 48 |
| Ser | Gln | Glu | Pro | Lys | Trp | Lys | Leu | Val | Trp | Ser | Asp | Glu | Phe | Thr | Asn | |
| 1 | | | | 5 | | | | | 10 | | | | | 15 | | |

| gga | atc | agt | tca | gat | tgg | gaa | ttc | gaa | acg | ggc | aat | ggc | ccc | aac | ggt | 96 |
|---|---|---|---|---|---|---|---|---|---|---|---|---|---|---|---|---|
| Gly | Ile | Ser | Ser | Asp | Trp | Glu | Phe | Glu | Thr | Gly | Asn | Gly | Pro | Asn | Gly | |
| | | | 20 | | | | | 25 | | | | | 30 | | | |

| tgg | ggc | aat | aac | gaa | ctg | caa | tat | tat | cgt | cgt | gaa | aat | acc | cga | gtt | 144 |
|---|---|---|---|---|---|---|---|---|---|---|---|---|---|---|---|---|
| Trp | Gly | Asn | Asn | Glu | Leu | Gln | Tyr | Tyr | Arg | Arg | Glu | Asn | Thr | Arg | Val | |
| | | 35 | | | | | 40 | | | | | 45 | | | | |

| gag | ggc | ggg | aaa | tta | ata | att | aca | gct | aaa | gaa | gaa | gat | tat | gag | ggt | 192 |
|---|---|---|---|---|---|---|---|---|---|---|---|---|---|---|---|---|
| Glu | Gly | Gly | Lys | Leu | Ile | Ile | Thr | Ala | Lys | Glu | Glu | Asp | Tyr | Glu | Gly | |
| 50 | | | | | 55 | | | | | 60 | | | | | | |

| ttc | agg | tac | act | tct | gcc | aag | ctg | aaa | acc | cag | ttc | aat | aaa | cct | tgg | 240 |
|---|---|---|---|---|---|---|---|---|---|---|---|---|---|---|---|---|
| Phe | Arg | Tyr | Thr | Ser | Ala | Lys | Leu | Lys | Thr | Gln | Phe | Asn | Lys | Pro | Trp | |
| 65 | | | | 70 | | | | | 75 | | | | | 80 | | |

| aaa | gat | ggt | aaa | att | gaa | gcc | aga | atg | tcg | att | cca | tca | ttt | cgg | ggg | 288 |
|---|---|---|---|---|---|---|---|---|---|---|---|---|---|---|---|---|
| Lys | Asp | Gly | Lys | Ile | Glu | Ala | Arg | Met | Ser | Ile | Pro | Ser | Phe | Arg | Gly | |
| | | | | 85 | | | | | 90 | | | | | 95 | | |

| gtc | tgg | gtg | gcg | ttc | tgg | atg | tta | gga | gac | atc | acc | gat | act | gat | agc | 336 |
|---|---|---|---|---|---|---|---|---|---|---|---|---|---|---|---|---|
| Val | Trp | Val | Ala | Phe | Trp | Met | Leu | Gly | Asp | Ile | Thr | Asp | Thr | Asp | Ser | |
| | | | 100 | | | | | 105 | | | | | 110 | | | |

| tgg | ccc | tct | tcc | ggt | gaa | att | gac | ttt | gag | gaa | cat | ata | aat | acc | aac | 384 |
|---|---|---|---|---|---|---|---|---|---|---|---|---|---|---|---|---|
| Trp | Pro | Ser | Ser | Gly | Glu | Ile | Asp | Phe | Glu | Glu | His | Ile | Asn | Thr | Asn | |
| | | 115 | | | | | 120 | | | | | 125 | | | | |

| aat | gaa | gtt | aga | gga | act | att | cac | tgg | tct | act | tct | gat | gac | gct | gat | 432 |
|---|---|---|---|---|---|---|---|---|---|---|---|---|---|---|---|---|
| Asn | Glu | Val | Arg | Gly | Thr | Ile | His | Trp | Ser | Thr | Ser | Asp | Asp | Ala | Asp | |
| | 130 | | | | | 135 | | | | | 140 | | | | | |

| aca | ctt | cat | ggc | aga | gga | acc | aat | act | gac | tat | cac | att | tat | tct | gta | 480 |
|---|---|---|---|---|---|---|---|---|---|---|---|---|---|---|---|---|
| Thr | Leu | His | Gly | Arg | Gly | Thr | Asn | Thr | Asp | Tyr | His | Ile | Tyr | Ser | Val | |
| 145 | | | | | 150 | | | | | 155 | | | | | 160 | |

| gag | tgg | aat | tct | tcc | gtt | att | aga | tgg | ttt | gtt | gat | gga | aat | cag | tac | 528 |
|---|---|---|---|---|---|---|---|---|---|---|---|---|---|---|---|---|
| Glu | Trp | Asn | Ser | Ser | Val | Ile | Arg | Trp | Phe | Val | Asp | Gly | Asn | Gln | Tyr | |
| | | | | 165 | | | | | 170 | | | | | 175 | | |

| ttt | gat | gtg | aat | att | cag | aga | gga | gca | act | gga | aca | aac | gca | ttt | cat | 576 |
|---|---|---|---|---|---|---|---|---|---|---|---|---|---|---|---|---|
| Phe | Asp | Val | Asn | Ile | Gln | Arg | Gly | Ala | Thr | Gly | Thr | Asn | Ala | Phe | His | |
| | | | 180 | | | | | 185 | | | | | 190 | | | |

| aat | aac | gtt | ttc | gtt | att | tta | aac | atg | gct | att | ggt | gga | aac | tgg | cca | 624 |
|---|---|---|---|---|---|---|---|---|---|---|---|---|---|---|---|---|
| Asn | Asn | Val | Phe | Val | Ile | Leu | Asn | Met | Ala | Ile | Gly | Gly | Asn | Trp | Pro | |
| | | 195 | | | | | 200 | | | | | 205 | | | | |

| gga | ttc | aat | gtt | gct | gat | gag | gct | ttc | cct | gct | aac | atg | tat | gta | gat | 672 |
|---|---|---|---|---|---|---|---|---|---|---|---|---|---|---|---|---|
| Gly | Phe | Asn | Val | Ala | Asp | Glu | Ala | Phe | Pro | Ala | Asn | Met | Tyr | Val | Asp | |
| | 210 | | | | | 215 | | | | | 220 | | | | | |

| tat | gtc | cgt | gta | tat | cag | gat | gcc | aat | aca | cct | tct | cct | gtt | gac | gtt | 720 |
|---|---|---|---|---|---|---|---|---|---|---|---|---|---|---|---|---|
| Tyr | Val | Arg | Val | Tyr | Gln | Asp | Ala | Asn | Thr | Pro | Ser | Pro | Val | Asp | Val | |
| 225 | | | | | 230 | | | | | 235 | | | | | 240 | |

| act | cat | tta | tct | ggt | tac | tat | ttt | ctt | caa | aat | agg | cac | agt | gaa | ctg | 768 |
|---|---|---|---|---|---|---|---|---|---|---|---|---|---|---|---|---|
| Thr | His | Leu | Ser | Gly | Tyr | Tyr | Phe | Leu | Gln | Asn | Arg | His | Ser | Glu | Leu | |
| | | | | 245 | | | | | 250 | | | | | 255 | | |

| tat | ctt | gat | gtc | agt | ggt | tcc | agt | aac | gaa | gat | gga | gca | ttt | cta | caa | 816 |
|---|---|---|---|---|---|---|---|---|---|---|---|---|---|---|---|---|
| Tyr | Leu | Asp | Val | Ser | Gly | Ser | Ser | Asn | Glu | Asp | Gly | Ala | Phe | Leu | Gln | |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 260 |     |     |     |     | 265 |     |     |     |     | 270 |     |     |     |      |
| caa | tgg | cct | tat | agc | ggt | aat | gct | aac | caa | cag | ttt | gat | ttt | gta | cat | 864  |
| Gln | Trp | Pro | Tyr | Ser | Gly | Asn | Ala | Asn | Gln | Gln | Phe | Asp | Phe | Val | His |      |
|     |     | 275 |     |     |     |     | 280 |     |     |     |     | 285 |     |     |     |      |
| ctc | gga | aat | aag | gtt | tat | aaa | att | atc | aat | aaa | aat | agt | gga | aaa | tct | 912  |
| Leu | Gly | Asn | Lys | Val | Tyr | Lys | Ile | Ile | Asn | Lys | Asn | Ser | Gly | Lys | Ser |      |
|     |     | 290 |     |     |     |     | 295 |     |     |     |     | 300 |     |     |     |      |
| ctg | gat | gtt | tac | gag | tta | ggg | act | gat | aat | ggt | gtc | aga | atc | caa | cag | 960  |
| Leu | Asp | Val | Tyr | Glu | Leu | Gly | Thr | Asp | Asn | Gly | Val | Arg | Ile | Gln | Gln |      |
| 305 |     |     |     |     | 310 |     |     |     |     | 315 |     |     |     |     | 320 |      |
| tgg | tcg | tat | gga | ggg | ggc | tac | aat | cag | cag | ttt | att | gta | caa | gat | gtt | 1008 |
| Trp | Ser | Tyr | Gly | Gly | Gly | Tyr | Asn | Gln | Gln | Phe | Ile | Val | Gln | Asp | Val |      |
|     |     |     |     | 325 |     |     |     |     | 330 |     |     |     |     | 335 |     |      |
| gga | gat | ggt | tat | tat | aag | ata | ttt | gca | cgc | agc | act | gga | aag | tta | gtg | 1056 |
| Gly | Asp | Gly | Tyr | Tyr | Lys | Ile | Phe | Ala | Arg | Ser | Thr | Gly | Lys | Leu | Val |      |
|     |     |     | 340 |     |     |     |     | 345 |     |     |     |     | 350 |     |     |      |
| gaa | gta | gca | gat | ttg | aat | aaa | gac | cca | gga | gga | aag | ata | caa | caa | tgg | 1104 |
| Glu | Val | Ala | Asp | Leu | Asn | Lys | Asp | Pro | Gly | Gly | Lys | Ile | Gln | Gln | Trp |      |
|     |     | 355 |     |     |     |     | 360 |     |     |     |     | 365 |     |     |     |      |
| tct | gat | gat | ggc | caa | tta | tcc | gga | cag | tgg | aaa | ctt | att | cga | aat | aaa | 1152 |
| Ser | Asp | Asp | Gly | Gln | Leu | Ser | Gly | Gln | Trp | Lys | Leu | Ile | Arg | Asn | Lys |      |
|     |     | 370 |     |     |     |     | 375 |     |     |     |     | 380 |     |     |     |      |
| gct | aat | tct | aaa | ttg | att | cag | gca | gaa | agt | tat | ttt | gct | agt | tca | aaa | 1200 |
| Ala | Asn | Ser | Lys | Leu | Ile | Gln | Ala | Glu | Ser | Tyr | Phe | Ala | Ser | Ser | Lys |      |
| 385 |     |     |     |     | 390 |     |     |     |     | 395 |     |     |     |     | 400 |      |
| gta | caa | ttg | gaa | gat | acc | tcg | gat | gta | gga | ggc | ggg | aag | aat | gtc | aag | 1248 |
| Val | Gln | Leu | Glu | Asp | Thr | Ser | Asp | Val | Gly | Gly | Gly | Lys | Asn | Val | Lys |      |
|     |     |     |     |     | 405 |     |     |     |     | 410 |     |     |     |     | 415 |      |
| tgt | gat | aat | gaa | gga | gcc | tgg | atg | gct | tac | aag | gat | atc | aat | ttc | cca | 1296 |
| Cys | Asp | Asn | Glu | Gly | Ala | Trp | Met | Ala | Tyr | Lys | Asp | Ile | Asn | Phe | Pro |      |
|     |     |     | 420 |     |     |     |     | 425 |     |     |     |     | 430 |     |     |      |
| agt | tca | ggt | act | tat | caa | gta | gag | tac | aga | gtg | gca | agt | gaa | cgt | gca | 1344 |
| Ser | Ser | Gly | Thr | Tyr | Gln | Val | Glu | Tyr | Arg | Val | Ala | Ser | Glu | Arg | Ala |      |
|     |     | 435 |     |     |     |     | 440 |     |     |     |     | 445 |     |     |     |      |
| gga | gga | atg | ttg | tct | ctg | gat | ttg | aat | gca | ggt | tct | ata | gtg | ctt | ggc | 1392 |
| Gly | Gly | Met | Leu | Ser | Leu | Asp | Leu | Asn | Ala | Gly | Ser | Ile | Val | Leu | Gly |      |
| 450 |     |     |     |     | 455 |     |     |     |     | 460 |     |     |     |     |     |      |
| atg | ctg | aat | gtt | cct | tca | act | gga | gga | ttg | cag | aag | tgg | acc | acc | att | 1440 |
| Met | Leu | Asn | Val | Pro | Ser | Thr | Gly | Gly | Leu | Gln | Lys | Trp | Thr | Thr | Ile |      |
| 465 |     |     |     |     | 470 |     |     |     |     | 475 |     |     |     |     | 480 |      |
| tcc | cac | aca | gtg | aat | gta | agt | tca | ggt | acg | tac | aac | ttg | ggg | atc | agt | 1488 |
| Ser | His | Thr | Val | Asn | Val | Ser | Ser | Gly | Thr | Tyr | Asn | Leu | Gly | Ile | Ser |      |
|     |     |     |     | 485 |     |     |     |     | 490 |     |     |     |     | 495 |     |      |
| gtt | caa | cga | ccc | ggg | tgg | aat | atc | aac | tgg | att | aat | att | aca | aaa | gta | 1536 |
| Val | Gln | Arg | Pro | Gly | Trp | Asn | Ile | Asn | Trp | Ile | Asn | Ile | Thr | Lys | Val |      |
|     |     |     | 500 |     |     |     |     | 505 |     |     |     |     | 510 |     |     |      |
| tcc | agt | cag | ttg | aaa | tct | att | cca | agt | act | aat | tct | aga | gta | att | cag | 1584 |
| Ser | Ser | Gln | Leu | Lys | Ser | Ile | Pro | Ser | Thr | Asn | Ser | Arg | Val | Ile | Gln |      |
|     |     | 515 |     |     |     |     | 520 |     |     |     |     | 525 |     |     |     |      |
| gca | gaa | agt | tat | ttc | gat | agt | tca | aaa | gta | caa | ttg | gaa | gac | acc | tcg | 1632 |
| Ala | Glu | Ser | Tyr | Phe | Asp | Ser | Ser | Lys | Val | Gln | Leu | Glu | Asp | Thr | Ser |      |
|     |     | 530 |     |     |     |     | 535 |     |     |     |     | 540 |     |     |     |      |
| gat | gtt | gga | ggc | ggg | aag | aat | gtt | aag | tgt | gat | act | aaa | gga | gcc | tgg | 1680 |
| Asp | Val | Gly | Gly | Gly | Lys | Asn | Val | Lys | Cys | Asp | Thr | Lys | Gly | Ala | Trp |      |
| 545 |     |     |     |     | 550 |     |     |     |     | 555 |     |     |     |     | 560 |      |
| atg | gcc | tac | aag | gat | atc | aat | ttt | ccc | agt | tca | ggt | agt | tat | caa | ata | 1728 |
| Met | Ala | Tyr | Lys | Asp | Ile | Asn | Phe | Pro | Ser | Ser | Gly | Ser | Tyr | Gln | Ile |      |
|     |     |     |     | 565 |     |     |     |     | 570 |     |     |     |     | 575 |     |      |
| gag | tac | aga | gtg | gca | agt | gaa | cgt | gca | gga | gga | aag | ttg | tct | ctc | gat | 1776 |

```
Glu Tyr Arg Val Ala Ser Glu Arg Ala Gly Lys Leu Ser Leu Asp
              580                 585                 590 ttg aat gca ggt tct ata gtg ctt gga atg ctg gat gtt cct tca act      1824
Leu Asn Ala Gly Ser Ile Val Leu Gly Met Leu Asp Val Pro Ser Thr
              595                 600                 605 ggg gga tgg cag aag tgg acc acc att tcc cat aca gta aag gtg gat      1872
Gly Gly Trp Gln Lys Trp Thr Thr Ile Ser His Thr Val Lys Val Asp
    610                 615                 620 tca ggt act tat aac ttg ggg atc tac gtt caa caa ccc ggg tgg aat      1920
Ser Gly Thr Tyr Asn Leu Gly Ile Tyr Val Gln Gln Pro Gly Trp Asn
625                 630                 635                 640 atc aac tgg att aag att aca aag gtt                                   1947
Ile Asn Trp Ile Lys Ile Thr Lys Val
                645

<210> SEQ ID NO 2
<211> LENGTH: 649
<212> TYPE: PRT
<213> ORGANISM: Limulus sp.

<400> SEQUENCE: 2

Ser Gln Glu Pro Lys Trp Lys Leu Val Trp Ser Asp Glu Phe Thr Asn
1               5                   10                  15

Gly Ile Ser Ser Asp Trp Glu Phe Glu Thr Gly Asn Gly Pro Asn Gly
            20                  25                  30

Trp Gly Asn Asn Glu Leu Gln Tyr Tyr Arg Arg Glu Asn Thr Arg Val
        35                  40                  45

Glu Gly Gly Lys Leu Ile Ile Thr Ala Lys Glu Asp Tyr Glu Gly
    50                  55                  60

Phe Arg Tyr Thr Ser Ala Lys Leu Lys Thr Gln Phe Asn Lys Pro Trp
65                  70                  75                  80

Lys Asp Gly Lys Ile Glu Ala Arg Met Ser Ile Pro Ser Phe Arg Gly
                85                  90                  95

Val Trp Val Ala Phe Trp Met Leu Gly Asp Ile Thr Thr Asp Ser
            100                 105                 110

Trp Pro Ser Ser Gly Glu Ile Asp Phe Glu Glu His Ile Asn Thr Asn
        115                 120                 125

Asn Glu Val Arg Gly Thr Ile His Trp Ser Thr Ser Asp Asp Ala Asp
    130                 135                 140

Thr Leu His Gly Arg Gly Thr Asn Thr Asp Tyr His Ile Tyr Ser Val
145                 150                 155                 160

Glu Trp Asn Ser Ser Val Ile Arg Trp Phe Val Asp Gly Asn Gln Tyr
                165                 170                 175

Phe Asp Val Asn Ile Gln Arg Gly Ala Thr Gly Thr Asn Ala Phe His
            180                 185                 190

Asn Asn Val Phe Val Ile Leu Asn Met Ala Ile Gly Gly Asn Trp Pro
        195                 200                 205

Gly Phe Asn Val Ala Asp Glu Ala Phe Pro Ala Asn Met Tyr Val Asp
    210                 215                 220

Tyr Val Arg Val Tyr Gln Asp Ala Asn Thr Pro Ser Pro Val Asp Val
225                 230                 235                 240

Thr His Leu Ser Gly Tyr Tyr Phe Leu Gln Asn Arg His Ser Glu Leu
                245                 250                 255

Tyr Leu Asp Val Ser Gly Ser Ser Asn Glu Asp Gly Ala Phe Leu Gln
            260                 265                 270

Gln Trp Pro Tyr Ser Gly Asn Ala Asn Gln Gln Phe Asp Phe Val His
```

```
                   275                 280                 285
Leu Gly Asn Lys Val Tyr Lys Ile Ile Asn Lys Asn Ser Gly Lys Ser
    290                 295                 300

Leu Asp Val Tyr Glu Leu Gly Thr Asp Asn Gly Val Arg Ile Gln Gln
305                 310                 315                 320

Trp Ser Tyr Gly Gly Tyr Asn Gln Gln Phe Ile Val Gln Asp Val
                325                 330                 335

Gly Asp Gly Tyr Tyr Lys Ile Phe Ala Arg Ser Thr Gly Lys Leu Val
                340                 345                 350

Glu Val Ala Asp Leu Asn Lys Asp Pro Gly Gly Lys Ile Gln Gln Trp
                355                 360                 365

Ser Asp Asp Gly Gln Leu Ser Gly Gln Trp Lys Leu Ile Arg Asn Lys
    370                 375                 380

Ala Asn Ser Lys Leu Ile Gln Ala Glu Ser Tyr Phe Ala Ser Ser Lys
385                 390                 395                 400

Val Gln Leu Glu Asp Thr Ser Asp Val Gly Gly Lys Asn Val Lys
                405                 410                 415

Cys Asp Asn Glu Gly Ala Trp Met Ala Tyr Lys Asp Ile Asn Phe Pro
                420                 425                 430

Ser Ser Gly Thr Tyr Gln Val Glu Tyr Arg Val Ala Ser Glu Arg Ala
                435                 440                 445

Gly Gly Met Leu Ser Leu Asp Leu Asn Ala Gly Ser Ile Val Leu Gly
    450                 455                 460

Met Leu Asn Val Pro Ser Thr Gly Gly Leu Gln Lys Trp Thr Thr Ile
465                 470                 475                 480

Ser His Thr Val Asn Val Ser Ser Gly Thr Tyr Asn Leu Gly Ile Ser
                485                 490                 495

Val Gln Arg Pro Gly Trp Asn Ile Asn Trp Ile Asn Ile Thr Lys Val
                500                 505                 510

Ser Ser Gln Leu Lys Ser Ile Pro Ser Thr Asn Ser Arg Val Ile Gln
    515                 520                 525

Ala Glu Ser Tyr Phe Asp Ser Ser Lys Val Gln Leu Glu Asp Thr Ser
530                 535                 540

Asp Val Gly Gly Gly Lys Asn Val Lys Cys Asp Thr Lys Gly Ala Trp
545                 550                 555                 560

Met Ala Tyr Lys Asp Ile Asn Phe Pro Ser Ser Gly Ser Tyr Gln Ile
                565                 570                 575

Glu Tyr Arg Val Ala Ser Glu Arg Ala Gly Lys Leu Ser Leu Asp
                580                 585                 590

Leu Asn Ala Gly Ser Ile Val Leu Gly Met Leu Asp Val Pro Ser Thr
                595                 600                 605

Gly Gly Trp Gln Lys Trp Thr Thr Ile Ser His Thr Val Lys Val Asp
    610                 615                 620

Ser Gly Thr Tyr Asn Leu Gly Ile Tyr Val Gln Gln Pro Gly Trp Asn
625                 630                 635                 640

Ile Asn Trp Ile Lys Ile Thr Lys Val
                645

<210> SEQ ID NO 3
<211> LENGTH: 1251
<212> TYPE: DNA
<213> ORGANISM: Limulus sp.
<220> FEATURE:
<221> NAME/KEY: CDS
<222> LOCATION: (1)..(1251)
```

<400> SEQUENCE: 3

```
aat aca cct tct cct gtt gac gtt act cat tta tct ggt tac tat ttt         48
Asn Thr Pro Ser Pro Val Asp Val Thr His Leu Ser Gly Tyr Tyr Phe
1               5                   10                  15 ctt caa aat agg cac agt gaa ctg tat ctt gat gtc agt ggt tcc agt         96
Leu Gln Asn Arg His Ser Glu Leu Tyr Leu Asp Val Ser Gly Ser Ser
            20                  25                  30 aac gaa gat gga gca ttt cta caa caa tgg cct tat agc ggt aat gct        144
Asn Glu Asp Gly Ala Phe Leu Gln Gln Trp Pro Tyr Ser Gly Asn Ala
        35                  40                  45 aac caa cag ttt gat ttt gta cat ctc gga aat aag gtt tat aaa att        192
Asn Gln Gln Phe Asp Phe Val His Leu Gly Asn Lys Val Tyr Lys Ile
    50                  55                  60 atc aat aaa aat agt gga aaa tct ctg gat gtt tac gag tta ggg act        240
Ile Asn Lys Asn Ser Gly Lys Ser Leu Asp Val Tyr Glu Leu Gly Thr
65                  70                  75                  80 gat aat ggt gtc aga atc caa cag tgg tcg tat gga ggg ggc tac aat        288
Asp Asn Gly Val Arg Ile Gln Gln Trp Ser Tyr Gly Gly Gly Tyr Asn
                85                  90                  95 cag cag ttt att gta caa gat gtt gga gat ggt tat tat aag ata ttt        336
Gln Gln Phe Ile Val Gln Asp Val Gly Asp Gly Tyr Tyr Lys Ile Phe
            100                 105                 110 gca cgc agc act gga aag tta gtg gaa gta gca gat ttg aat aaa gac        384
Ala Arg Ser Thr Gly Lys Leu Val Glu Val Ala Asp Leu Asn Lys Asp
        115                 120                 125 cca gga gga aag ata caa caa tgg tct gat gat ggc caa tta tcc gga        432
Pro Gly Gly Lys Ile Gln Gln Trp Ser Asp Asp Gly Gln Leu Ser Gly
    130                 135                 140 cag tgg aaa ctt att cga aat aaa gct aat tct aaa ttg att cag gca        480
Gln Trp Lys Leu Ile Arg Asn Lys Ala Asn Ser Lys Leu Ile Gln Ala
145                 150                 155                 160 gaa agt tat ttt gct agt tca aaa gta caa ttg gaa gat acc tcg gat        528
Glu Ser Tyr Phe Ala Ser Ser Lys Val Gln Leu Glu Asp Thr Ser Asp
                165                 170                 175 gta gga ggc ggg aag aat gtc aag tgt gat aat gaa gga gcc tgg atg        576
Val Gly Gly Gly Lys Asn Val Lys Cys Asp Asn Glu Gly Ala Trp Met
            180                 185                 190 gct tac aag gat atc aat ttc cca agt tca ggt act tat caa gta gag        624
Ala Tyr Lys Asp Ile Asn Phe Pro Ser Ser Gly Thr Tyr Gln Val Glu
        195                 200                 205 tac aga gtg gca agt gaa cgt gca gga gga atg ttg tct ctg gat ttg        672
Tyr Arg Val Ala Ser Glu Arg Ala Gly Gly Met Leu Ser Leu Asp Leu
    210                 215                 220 aat gca ggt tct ata gtg ctt ggc atg ctg aat gtt cct tca act gga        720
Asn Ala Gly Ser Ile Val Leu Gly Met Leu Asn Val Pro Ser Thr Gly
225                 230                 235                 240 gga ttg cag aag tgg acc acc att tcc cac aca gtg aat gta agt tca        768
Gly Leu Gln Lys Trp Thr Thr Ile Ser His Thr Val Asn Val Ser Ser
                245                 250                 255 ggt acg tac aac ttg ggg atc agt gtt caa cga ccc ggg tgg aat atc        816
Gly Thr Tyr Asn Leu Gly Ile Ser Val Gln Arg Pro Gly Trp Asn Ile
            260                 265                 270 aac tgg att aat att aca aaa gta tcc agt cag ttg aaa tct att cca        864
Asn Trp Ile Asn Ile Thr Lys Val Ser Ser Gln Leu Lys Ser Ile Pro
        275                 280                 285 agt act aat tct aga gta att cag gca gaa agt tat ttc gat agt tca        912
Ser Thr Asn Ser Arg Val Ile Gln Ala Glu Ser Tyr Phe Asp Ser Ser
    290                 295                 300
```

```
aaa gta caa ttg gaa gac acc tcg gat gtt gga ggc ggg aag aat gtt      960
Lys Val Gln Leu Glu Asp Thr Ser Asp Val Gly Gly Gly Lys Asn Val
305                 310                 315                 320 aag tgt gat act aaa gga gcc tgg atg gcc tac aag gat atc aat ttt     1008
Lys Cys Asp Thr Lys Gly Ala Trp Met Ala Tyr Lys Asp Ile Asn Phe
            325                 330                 335 ccc agt tca ggt agt tat caa ata gag tac aga gtg gca agt gaa cgt    1056
Pro Ser Ser Gly Ser Tyr Gln Ile Glu Tyr Arg Val Ala Ser Glu Arg
                340                 345                 350 gca gga gga aag ttg tct ctc gat ttg aat gca ggt tct ata gtg ctt    1104
Ala Gly Gly Lys Leu Ser Leu Asp Leu Asn Ala Gly Ser Ile Val Leu
            355                 360                 365 gga atg ctg gat gtt cct tca act ggg gga tgg cag aag tgg acc acc    1152
Gly Met Leu Asp Val Pro Ser Thr Gly Gly Trp Gln Lys Trp Thr Thr
370                 375                 380 att tcc cat aca gta aag gtg gat tca ggt act tat aac ttg ggg atc    1200
Ile Ser His Thr Val Lys Val Asp Ser Gly Thr Tyr Asn Leu Gly Ile
385                 390                 395                 400 tac gtt caa caa ccc ggg tgg aat atc aac tgg att aag att aca aag    1248
Tyr Val Gln Gln Pro Gly Trp Asn Ile Asn Trp Ile Lys Ile Thr Lys
                405                 410                 415 gtt                                                                 1251
Val

<210> SEQ ID NO 4
<211> LENGTH: 417
<212> TYPE: PRT
<213> ORGANISM: Limulus sp.

<400> SEQUENCE: 4

Asn Thr Pro Ser Pro Val Asp Val Thr His Leu Ser Gly Tyr Tyr Phe
1               5                   10                  15

Leu Gln Asn Arg His Ser Glu Leu Tyr Leu Asp Val Ser Gly Ser Ser
            20                  25                  30

Asn Glu Asp Gly Ala Phe Leu Gln Gln Trp Pro Tyr Ser Gly Asn Ala
        35                  40                  45

Asn Gln Gln Phe Asp Phe Val His Leu Gly Asn Lys Val Tyr Lys Ile
    50                  55                  60

Ile Asn Lys Asn Ser Gly Lys Ser Leu Asp Val Tyr Glu Leu Gly Thr
65                  70                  75                  80

Asp Asn Gly Val Arg Ile Gln Gln Trp Ser Tyr Gly Gly Tyr Asn
                85                  90                  95

Gln Gln Phe Ile Val Gln Asp Val Gly Asp Gly Tyr Tyr Lys Ile Phe
            100                 105                 110

Ala Arg Ser Thr Gly Lys Leu Val Glu Val Ala Asp Leu Asn Lys Asp
        115                 120                 125

Pro Gly Gly Lys Ile Gln Gln Trp Ser Asp Asp Gly Gln Leu Ser Gly
    130                 135                 140

Gln Trp Lys Leu Ile Arg Asn Lys Ala Asn Ser Lys Leu Ile Gln Ala
145                 150                 155                 160

Glu Ser Tyr Phe Ala Ser Ser Lys Val Gln Leu Glu Asp Thr Ser Asp
                165                 170                 175

Val Gly Gly Gly Lys Asn Val Lys Cys Asp Asn Glu Gly Ala Trp Met
            180                 185                 190

Ala Tyr Lys Asp Ile Asn Phe Pro Ser Ser Gly Thr Tyr Gln Val Glu
        195                 200                 205

Tyr Arg Val Ala Ser Glu Arg Ala Gly Gly Met Leu Ser Leu Asp Leu
```

-continued

```
                    210                 215                 220
Asn Ala Gly Ser Ile Val Leu Gly Met Leu Asn Val Pro Ser Thr Gly
225                 230                 235                 240

Gly Leu Gln Lys Trp Thr Thr Ile Ser His Thr Val Asn Val Ser Ser
                245                 250                 255

Gly Thr Tyr Asn Leu Gly Ile Ser Val Gln Arg Pro Gly Trp Asn Ile
            260                 265                 270

Asn Trp Ile Asn Ile Thr Lys Val Ser Gln Leu Lys Ser Ile Pro
        275                 280                 285

Ser Thr Asn Ser Arg Val Ile Gln Ala Glu Ser Tyr Phe Asp Ser Ser
    290                 295                 300

Lys Val Gln Leu Glu Asp Thr Ser Asp Val Gly Gly Lys Asn Val
305                 310                 315                 320

Lys Cys Asp Thr Lys Gly Ala Trp Met Ala Tyr Lys Asp Ile Asn Phe
                325                 330                 335

Pro Ser Ser Gly Ser Tyr Gln Ile Glu Tyr Arg Val Ala Ser Glu Arg
            340                 345                 350

Ala Gly Gly Lys Leu Ser Leu Asp Leu Asn Ala Gly Ser Ile Val Leu
        355                 360                 365

Gly Met Leu Asp Val Pro Ser Thr Gly Gly Trp Gln Lys Trp Thr Thr
    370                 375                 380

Ile Ser His Thr Val Lys Val Asp Ser Gly Thr Tyr Asn Leu Gly Ile
385                 390                 395                 400

Tyr Val Gln Gln Pro Gly Trp Asn Ile Asn Trp Ile Lys Ile Thr Lys
                405                 410                 415
Val
```

```
<210> SEQ ID NO 5
<211> LENGTH: 789
<212> TYPE: DNA
<213> ORGANISM: Limulus sp.
<220> FEATURE:
<221> NAME/KEY: CDS
<222> LOCATION: (1)..(789)

<400> SEQUENCE: 5
```

```
tct aaa ttg att cag gca gaa agt tat ttt gct agt tca aaa gta caa    48
Ser Lys Leu Ile Gln Ala Glu Ser Tyr Phe Ala Ser Ser Lys Val Gln
1               5                   10                  15 ttg gaa gat acc tcg gat gta gga ggc ggg aag aat gtc aag tgt gat    96
Leu Glu Asp Thr Ser Asp Val Gly Gly Gly Lys Asn Val Lys Cys Asp
            20                  25                  30 aat gaa gga gcc tgg atg gct tac aag gat atc aat ttc cca agt tca   144
Asn Glu Gly Ala Trp Met Ala Tyr Lys Asp Ile Asn Phe Pro Ser Ser
        35                  40                  45 ggt act tat caa gta gag tac aga gtg gca agt gaa cgt gca gga gga   192
Gly Thr Tyr Gln Val Glu Tyr Arg Val Ala Ser Glu Arg Ala Gly Gly
    50                  55                  60 atg ttg tct ctg gat ttg aat gca ggt tct ata gtg ctt ggc atg ctg   240
Met Leu Ser Leu Asp Leu Asn Ala Gly Ser Ile Val Leu Gly Met Leu
65                  70                  75                  80 aat gtt cct tca act gga gga ttg cag aag tgg acc acc att tcc cac   288
Asn Val Pro Ser Thr Gly Gly Leu Gln Lys Trp Thr Thr Ile Ser His
                85                  90                  95 aca gtg aat gta agt tca ggt acg tac aac ttg ggg atc agt gtt caa   336
Thr Val Asn Val Ser Ser Gly Thr Tyr Asn Leu Gly Ile Ser Val Gln
            100                 105                 110
```

```
cga ccc ggg tgg aat atc aac tgg att aat att aca aaa gta tcc agt         384
Arg Pro Gly Trp Asn Ile Asn Trp Ile Asn Ile Thr Lys Val Ser Ser
        115                 120                 125 cag ttg aaa tct att cca agt act aat tct aga gta att cag gca gaa         432
Gln Leu Lys Ser Ile Pro Ser Thr Asn Ser Arg Val Ile Gln Ala Glu
    130                 135                 140 agt tat ttc gat agt tca aaa gta caa ttg gaa gac acc tcg gat gtt         480
Ser Tyr Phe Asp Ser Ser Lys Val Gln Leu Glu Asp Thr Ser Asp Val
145                 150                 155                 160 gga ggc ggg aag aat gtt aag tgt gat act aaa gga gcc tgg atg gcc         528
Gly Gly Gly Lys Asn Val Lys Cys Asp Thr Lys Gly Ala Trp Met Ala
            165                 170                 175 tac aag gat atc aat ttt ccc agt tca ggt agt tat caa ata gag tac         576
Tyr Lys Asp Ile Asn Phe Pro Ser Ser Gly Ser Tyr Gln Ile Glu Tyr
        180                 185                 190 aga gtg gca agt gaa cgt gca gga gga aag ttg tct ctc gat ttg aat         624
Arg Val Ala Ser Glu Arg Ala Gly Gly Lys Leu Ser Leu Asp Leu Asn
    195                 200                 205 gca ggt tct ata gtg ctt gga atg ctg gat gtt cct tca act ggg gga         672
Ala Gly Ser Ile Val Leu Gly Met Leu Asp Val Pro Ser Thr Gly Gly
210                 215                 220 tgg cag aag tgg acc acc att tcc cat aca gta aag gtg gat tca ggt         720
Trp Gln Lys Trp Thr Thr Ile Ser His Thr Val Lys Val Asp Ser Gly
225                 230                 235                 240 act tat aac ttg ggg atc tac gtt caa caa ccc ggg tgg aat atc aac         768
Thr Tyr Asn Leu Gly Ile Tyr Val Gln Gln Pro Gly Trp Asn Ile Asn
            245                 250                 255 tgg att aag att aca aag gtt                                             789
Trp Ile Lys Ile Thr Lys Val
        260

<210> SEQ ID NO 6
<211> LENGTH: 263
<212> TYPE: PRT
<213> ORGANISM: Limulus sp.

<400> SEQUENCE: 6

Ser Lys Leu Ile Gln Ala Glu Ser Tyr Phe Ala Ser Ser Lys Val Gln
1               5                   10                  15

Leu Glu Asp Thr Ser Asp Val Gly Gly Gly Lys Asn Val Lys Cys Asp
            20                  25                  30

Asn Glu Gly Ala Trp Met Ala Tyr Lys Asp Ile Asn Phe Pro Ser Ser
        35                  40                  45

Gly Thr Tyr Gln Val Glu Tyr Arg Val Ala Ser Glu Arg Ala Gly Gly
    50                  55                  60

Met Leu Ser Leu Asp Leu Asn Ala Gly Ser Ile Val Leu Gly Met Leu
65                  70                  75                  80

Asn Val Pro Ser Thr Gly Gly Leu Gln Lys Trp Thr Thr Ile Ser His
            85                  90                  95

Thr Val Asn Val Ser Ser Gly Tyr Asn Leu Gly Ile Ser Val Gln
        100                 105                 110

Arg Pro Gly Trp Asn Ile Asn Trp Ile Asn Ile Thr Lys Val Ser Ser
    115                 120                 125

Gln Leu Lys Ser Ile Pro Ser Thr Asn Ser Arg Val Ile Gln Ala Glu
130                 135                 140

Ser Tyr Phe Asp Ser Ser Lys Val Gln Leu Glu Asp Thr Ser Asp Val
145                 150                 155                 160

Gly Gly Gly Lys Asn Val Lys Cys Asp Thr Lys Gly Ala Trp Met Ala
```

```
                   165                 170                 175
Tyr Lys Asp Ile Asn Phe Pro Ser Ser Gly Ser Tyr Gln Ile Glu Tyr
            180                 185                 190

Arg Val Ala Ser Glu Arg Ala Gly Gly Lys Leu Ser Leu Asp Leu Asn
        195                 200                 205

Ala Gly Ser Ile Val Leu Gly Met Leu Asp Val Pro Ser Thr Gly Gly
    210                 215                 220

Trp Gln Lys Trp Thr Thr Ile Ser His Thr Val Lys Val Asp Ser Gly
225                 230                 235                 240

Thr Tyr Asn Leu Gly Ile Tyr Val Gln Gln Pro Gly Trp Asn Ile Asn
                245                 250                 255

Trp Ile Lys Ile Thr Lys Val
            260

<210> SEQ ID NO 7
<211> LENGTH: 378
<212> TYPE: DNA
<213> ORGANISM: Limulus sp.
<220> FEATURE:
<221> NAME/KEY: CDS
<222> LOCATION: (1)..(378)

<400> SEQUENCE: 7 tct aga gta att cag gca gaa agt tat ttc gat agt tca aaa gta caa        48
Ser Arg Val Ile Gln Ala Glu Ser Tyr Phe Asp Ser Ser Lys Val Gln
1               5                   10                  15 ttg gaa gac acc tcg gat gtt gga ggc ggg aag aat gtt aag tgt gat        96
Leu Glu Asp Thr Ser Asp Val Gly Gly Gly Lys Asn Val Lys Cys Asp
            20                  25                  30 act aaa gga gcc tgg atg gcc tac aag gat atc aat ttt ccc agt tca       144
Thr Lys Gly Ala Trp Met Ala Tyr Lys Asp Ile Asn Phe Pro Ser Ser
        35                  40                  45 ggt agt tat caa ata gag tac aga gtg gca agt gaa cgt gca gga gga       192
Gly Ser Tyr Gln Ile Glu Tyr Arg Val Ala Ser Glu Arg Ala Gly Gly
    50                  55                  60 aag ttg tct ctc gat ttg aat gca ggt tct ata gtg ctt gga atg ctg       240
Lys Leu Ser Leu Asp Leu Asn Ala Gly Ser Ile Val Leu Gly Met Leu
65                  70                  75                  80 gat gtt cct tca act ggg gga tgg cag aag tgg acc acc att tcc cat       288
Asp Val Pro Ser Thr Gly Gly Trp Gln Lys Trp Thr Thr Ile Ser His
                85                  90                  95 aca gta aag gtg gat tca ggt act tat aac ttg ggg atc tac gtt caa       336
Thr Val Lys Val Asp Ser Gly Thr Tyr Asn Leu Gly Ile Tyr Val Gln
            100                 105                 110 caa ccc ggg tgg aat atc aac tgg att aag att aca aag gtt               378
Gln Pro Gly Trp Asn Ile Asn Trp Ile Lys Ile Thr Lys Val
        115                 120                 125

<210> SEQ ID NO 8
<211> LENGTH: 126
<212> TYPE: PRT
<213> ORGANISM: Limulus sp.

<400> SEQUENCE: 8

Ser Arg Val Ile Gln Ala Glu Ser Tyr Phe Asp Ser Ser Lys Val Gln
1               5                   10                  15

Leu Glu Asp Thr Ser Asp Val Gly Gly Gly Lys Asn Val Lys Cys Asp
            20                  25                  30

Thr Lys Gly Ala Trp Met Ala Tyr Lys Asp Ile Asn Phe Pro Ser Ser
        35                  40                  45
```

```
Gly Ser Tyr Gln Ile Glu Tyr Arg Val Ala Ser Glu Arg Ala Gly Gly
         50                  55                  60

Lys Leu Ser Leu Asp Leu Asn Ala Gly Ser Ile Val Leu Gly Met Leu
 65                  70                  75                  80

Asp Val Pro Ser Thr Gly Gly Trp Gln Lys Trp Thr Thr Ile Ser His
                 85                  90                  95

Thr Val Lys Val Asp Ser Gly Thr Tyr Asn Leu Gly Ile Tyr Val Gln
            100                 105                 110

Gln Pro Gly Trp Asn Ile Asn Trp Ile Lys Ile Thr Lys Val
            115                 120                 125

<210> SEQ ID NO 9
<211> LENGTH: 849
<212> TYPE: DNA
<213> ORGANISM: Limulus sp.
<220> FEATURE:
<221> NAME/KEY: CDS
<222> LOCATION: (1)..(849)

<400> SEQUENCE: 9 aat aca cct tct cct gtt gac gtt act cat tta tct ggt tac tat ttt      48
Asn Thr Pro Ser Pro Val Asp Val Thr His Leu Ser Gly Tyr Tyr Phe
 1               5                  10                  15 ctt caa aat agg cac agt gaa ctg tat ctt gat gtc agt ggt tcc agt      96
Leu Gln Asn Arg His Ser Glu Leu Tyr Leu Asp Val Ser Gly Ser Ser
             20                  25                  30 aac gaa gat gga gca ttt cta caa caa tgg cct tat agc ggt aat gct     144
Asn Glu Asp Gly Ala Phe Leu Gln Gln Trp Pro Tyr Ser Gly Asn Ala
         35                  40                  45 aac caa cag ttt gat ttt gta cat ctc gga aat aag gtt tat aaa att     192
Asn Gln Gln Phe Asp Phe Val His Leu Gly Asn Lys Val Tyr Lys Ile
     50                  55                  60 atc aat aaa aat agt gga aaa tct ctg gat gtt tac gag tta ggg act     240
Ile Asn Lys Asn Ser Gly Lys Ser Leu Asp Val Tyr Glu Leu Gly Thr
 65                  70                  75                  80 gat aat ggt gtc aga atc caa cag tgg tcg tat gga ggg ggc tac aat     288
Asp Asn Gly Val Arg Ile Gln Gln Trp Ser Tyr Gly Gly Gly Tyr Asn
                 85                  90                  95 cag cag ttt att gta caa gat gtt gga gat ggt tat tat aag ata ttt     336
Gln Gln Phe Ile Val Gln Asp Val Gly Asp Gly Tyr Tyr Lys Ile Phe
            100                 105                 110 gca cgc agc act gga aag tta gtg gaa gta gca gat ttg aat aaa gac     384
Ala Arg Ser Thr Gly Lys Leu Val Glu Val Ala Asp Leu Asn Lys Asp
        115                 120                 125 cca gga gga aag ata caa caa tgg tct gat gat ggc caa tta tcc gga     432
Pro Gly Gly Lys Ile Gln Gln Trp Ser Asp Asp Gly Gln Leu Ser Gly
    130                 135                 140 cag tgg aaa ctt att cga aat aaa gct aat tct aaa ttg att cag gca     480
Gln Trp Lys Leu Ile Arg Asn Lys Ala Asn Ser Lys Leu Ile Gln Ala
145                 150                 155                 160 gaa agt tat ttt gct agt tca aaa gta caa ttg gaa gat acc tcg gat     528
Glu Ser Tyr Phe Ala Ser Ser Lys Val Gln Leu Glu Asp Thr Ser Asp
                165                 170                 175 gta gga ggc ggg aag aat gtc aag tgt gat aat gaa gga gcc tgg atg     576
Val Gly Gly Gly Lys Asn Val Lys Cys Asp Asn Glu Gly Ala Trp Met
            180                 185                 190 gct tac aag gat atc aat ttc cca agt tca ggt act tat caa gta gag     624
Ala Tyr Lys Asp Ile Asn Phe Pro Ser Ser Gly Thr Tyr Gln Val Glu
        195                 200                 205
```

| | | | | | | | | | | | | | | | |
|---|---|---|---|---|---|---|---|---|---|---|---|---|---|---|---|
| tac | aga | gtg | gca | agt | gaa | cgt | gca | gga | gga | atg | ttg | tct | ctg | gat | ttg | 672 |
| Tyr | Arg | Val | Ala | Ser | Glu | Arg | Ala | Gly | Gly | Met | Leu | Ser | Leu | Asp | Leu | |
| | 210 | | | | 215 | | | | | 220 | | | | | | |
| aat | gca | ggt | tct | ata | gtg | ctt | ggc | atg | ctg | aat | gtt | cct | tca | act | gga | 720 |
| Asn | Ala | Gly | Ser | Ile | Val | Leu | Gly | Met | Leu | Asn | Val | Pro | Ser | Thr | Gly | |
| 225 | | | | | 230 | | | | | 235 | | | | | 240 | |
| gga | ttg | cag | aag | tgg | acc | acc | att | tcc | cac | aca | gtg | aat | gta | agt | tca | 768 |
| Gly | Leu | Gln | Lys | Trp | Thr | Thr | Ile | Ser | His | Thr | Val | Asn | Val | Ser | Ser | |
| | | | | 245 | | | | | 250 | | | | | 255 | | |
| ggt | acg | tac | aac | ttg | ggg | atc | agt | gtt | caa | cga | ccc | ggg | tgg | aat | atc | 816 |
| Gly | Thr | Tyr | Asn | Leu | Gly | Ile | Ser | Val | Gln | Arg | Pro | Gly | Trp | Asn | Ile | |
| | | | 260 | | | | | 265 | | | | | 270 | | | |
| aac | tgg | att | aat | att | aca | aaa | gta | tcc | agt | cag | | | | | | 849 |
| Asn | Trp | Ile | Asn | Ile | Thr | Lys | Val | Ser | Ser | Gln | | | | | | |
| | | | 275 | | | | | 280 | | | | | | | | |

<210> SEQ ID NO 10
<211> LENGTH: 283
<212> TYPE: PRT
<213> ORGANISM: Limulus sp.

<400> SEQUENCE: 10

Asn Thr Pro Ser Pro Val Asp Val Thr His Leu Ser Gly Tyr Tyr Phe
1               5                   10                  15

Leu Gln Asn Arg His Ser Glu Leu Tyr Leu Asp Val Ser Gly Ser Ser
            20                  25                  30

Asn Glu Asp Gly Ala Phe Leu Gln Gln Trp Pro Tyr Ser Gly Asn Ala
        35                  40                  45

Asn Gln Gln Phe Asp Phe Val His Leu Gly Asn Lys Val Tyr Lys Ile
    50                  55                  60

Ile Asn Lys Asn Ser Gly Lys Ser Leu Asp Val Tyr Glu Leu Gly Thr
65                  70                  75                  80

Asp Asn Gly Val Arg Ile Gln Gln Trp Ser Tyr Gly Gly Gly Tyr Asn
                85                  90                  95

Gln Gln Phe Ile Val Gln Asp Val Gly Asp Gly Tyr Tyr Lys Ile Phe
            100                 105                 110

Ala Arg Ser Thr Gly Lys Leu Val Glu Val Ala Asp Leu Asn Lys Asp
        115                 120                 125

Pro Gly Gly Lys Ile Gln Gln Trp Ser Asp Asp Gly Gln Leu Ser Gly
    130                 135                 140

Gln Trp Lys Leu Ile Arg Asn Lys Ala Asn Ser Lys Leu Ile Gln Ala
145                 150                 155                 160

Glu Ser Tyr Phe Ala Ser Ser Lys Val Gln Leu Glu Asp Thr Ser Asp
                165                 170                 175

Val Gly Gly Gly Lys Asn Val Lys Cys Asp Asn Glu Gly Ala Trp Met
            180                 185                 190

Ala Tyr Lys Asp Ile Asn Phe Pro Ser Ser Gly Thr Tyr Gln Val Glu
        195                 200                 205

Tyr Arg Val Ala Ser Glu Arg Ala Gly Gly Met Leu Ser Leu Asp Leu
    210                 215                 220

Asn Ala Gly Ser Ile Val Leu Gly Met Leu Asn Val Pro Ser Thr Gly
225                 230                 235                 240

Gly Leu Gln Lys Trp Thr Thr Ile Ser His Thr Val Asn Val Ser Ser
                245                 250                 255

Gly Thr Tyr Asn Leu Gly Ile Ser Val Gln Arg Pro Gly Trp Asn Ile
            260                 265                 270

```
Asn Trp Ile Asn Ile Thr Lys Val Ser Ser Gln
            275                 280
```

<210> SEQ ID NO 11
<211> LENGTH: 2022
<212> TYPE: DNA
<213> ORGANISM: Tachyporus sp.
<220> FEATURE:
<221> NAME/KEY: CDS
<222> LOCATION: (1)..(2022)

<400> SEQUENCE: 11

```
atg ttg gtg ttg ctg tgt tgt gtt gtt ttg cat gtt ggt gtt gca aga      48
Met Leu Val Leu Leu Cys Cys Val Val Leu His Val Gly Val Ala Arg
1               5                   10                  15 att tgc tgt agc cac gaa cca aag tgg cag ctc gtc tgg tcg gat gaa      96
Ile Cys Cys Ser His Glu Pro Lys Trp Gln Leu Val Trp Ser Asp Glu
                20                  25                  30 ttt acc aat gga ata agt tct gat tgg gaa ttt gaa atg ggc aat ggc     144
Phe Thr Asn Gly Ile Ser Ser Asp Trp Glu Phe Glu Met Gly Asn Gly
            35                  40                  45 ctc aat ggt tgg ggt aat aac gaa ctg caa tat tat cgt cgt gaa aat     192
Leu Asn Gly Trp Gly Asn Asn Glu Leu Gln Tyr Tyr Arg Arg Glu Asn
        50                  55                  60 gcc caa gtt gag gga ggg aaa ctg gta att act gct aaa aga gaa gac     240
Ala Gln Val Glu Gly Gly Lys Leu Val Ile Thr Ala Lys Arg Glu Asp
65                  70                  75                  80 tat gat ggc ttc aaa tac act tct gct agg ctg aaa acc cag ttt gat     288
Tyr Asp Gly Phe Lys Tyr Thr Ser Ala Arg Leu Lys Thr Gln Phe Asp
                85                  90                  95 aaa tct tgg aag tat ggt aaa att gaa gcc aaa atg gcg att cca tca     336
Lys Ser Trp Lys Tyr Gly Lys Ile Glu Ala Lys Met Ala Ile Pro Ser
            100                 105                 110 ttt cgg gga gtc tgg gtg atg ttc tgg atg tca gga gac aac act aat     384
Phe Arg Gly Val Trp Val Met Phe Trp Met Ser Gly Asp Asn Thr Asn
        115                 120                 125 tat gtt aga tgg cca tct tct ggt gaa att gac ttt att gaa cat aga     432
Tyr Val Arg Trp Pro Ser Ser Gly Glu Ile Asp Phe Ile Glu His Arg
    130                 135                 140 aac act aac aat gaa aaa gtc aga gga act att cac tgg tcc act cct     480
Asn Thr Asn Asn Glu Lys Val Arg Gly Thr Ile His Trp Ser Thr Pro
145                 150                 155                 160 gac ggt gct cat gcg cat cat aac aga gaa agt aat aca aat ggg att     528
Asp Gly Ala His Ala His His Asn Arg Glu Ser Asn Thr Asn Gly Ile
                165                 170                 175 gat tat cac att tat tct gta gag tgg aat tct tcc att gtt aaa tgg     576
Asp Tyr His Ile Tyr Ser Val Glu Trp Asn Ser Ser Ile Val Lys Trp
            180                 185                 190 ttt gtt aat gga aat caa tac ttt gaa gtg aaa att cag gga gga gta     624
Phe Val Asn Gly Asn Gln Tyr Phe Glu Val Lys Ile Gln Gly Gly Val
        195                 200                 205 aat ggg aaa agt gca ttt cgt aac aaa gtt ttc gtt att tta aac atg     672
Asn Gly Lys Ser Ala Phe Arg Asn Lys Val Phe Val Ile Leu Asn Met
    210                 215                 220 gcg att ggt gga aac tgg cca gga ttc gat gtt gct gac gag gct ttc     720
Ala Ile Gly Gly Asn Trp Pro Gly Phe Asp Val Ala Asp Glu Ala Phe
225                 230                 235                 240 cct gct aaa atg tac att gat tat gtc cgt gta tac cag gat gcc agt     768
Pro Ala Lys Met Tyr Ile Asp Tyr Val Arg Val Tyr Gln Asp Ala Ser
                245                 250                 255 aca tct tct cct gtt ggg gat acc tct tta gat ggt tac tat ttt gtc     816
Thr Ser Ser Pro Val Gly Asp Thr Ser Leu Asp Gly Tyr Tyr Phe Val
```

```
Thr Ser Ser Pro Val Gly Asp Thr Ser Leu Asp Gly Tyr Tyr Phe Val
            260                 265                 270 caa aac agg cac agt gaa ttg tat ctt gat gtc act gat gcc agt aac       864
Gln Asn Arg His Ser Glu Leu Tyr Leu Asp Val Thr Asp Ala Ser Asn
    275                 280                 285 gaa gat gga gca ttt ctg caa caa tgg tct tat agt ggt aat gag aac       912
Glu Asp Gly Ala Phe Leu Gln Gln Trp Ser Tyr Ser Gly Asn Glu Asn
290                 295                 300 caa cag ttt gat ttt gag cat ctc gaa aat aat gtt tat aaa att act       960
Gln Gln Phe Asp Phe Glu His Leu Glu Asn Asn Val Tyr Lys Ile Thr
305                 310                 315                 320 aat aaa aaa agt gga aaa tct ttg gat gtt tat aat ttt ggg act gag      1008
Asn Lys Lys Ser Gly Lys Ser Leu Asp Val Tyr Asn Phe Gly Thr Glu
            325                 330                 335 aat ggt gtt aga atc caa cag tgg tca tat gga ggg gct cgc aat cag      1056
Asn Gly Val Arg Ile Gln Gln Trp Ser Tyr Gly Gly Ala Arg Asn Gln
            340                 345                 350 cag ttt act gta caa agt gtt ggt gat ggt tat tat aag att att cca      1104
Gln Phe Thr Val Gln Ser Val Gly Asp Gly Tyr Tyr Lys Ile Ile Pro
            355                 360                 365 cgc ggc agt gga aag tta gtg gaa gta gca gat ttt agt aaa gat gca      1152
Arg Gly Ser Gly Lys Leu Val Glu Val Ala Asp Phe Ser Lys Asp Ala
370                 375                 380 gga ggg aag ata caa caa tgg tct gat aac aac caa tta tct gga cag      1200
Gly Gly Lys Ile Gln Gln Trp Ser Asp Asn Asn Gln Leu Ser Gly Gln
385                 390                 395                 400 tgg aaa ctt att aaa agt aaa agt tat tct aaa tta att cag gca gaa      1248
Trp Lys Leu Ile Lys Ser Lys Ser Tyr Ser Lys Leu Ile Gln Ala Glu
            405                 410                 415 agt tat ttt gat tcc tca aaa gta caa ttg gaa gat acc tca gat gta      1296
Ser Tyr Phe Asp Ser Ser Lys Val Gln Leu Glu Asp Thr Ser Asp Val
            420                 425                 430 gga ggt ggg aag aat gtt aaa tgt gat aat gaa gga gcc tgg atg gct      1344
Gly Gly Gly Lys Asn Val Lys Cys Asp Asn Glu Gly Ala Trp Met Ala
            435                 440                 445 tat aag gat att gat ttc ccc agt tca ggt aat tat cga ata gaa tac      1392
Tyr Lys Asp Ile Asp Phe Pro Ser Ser Gly Asn Tyr Arg Ile Glu Tyr
450                 455                 460 aga gta gca agt gaa cgt gca gga gga aag ctg tct ctg gat ttg aat      1440
Arg Val Ala Ser Glu Arg Ala Gly Gly Lys Leu Ser Leu Asp Leu Asn
465                 470                 475                 480 gca ggc tct ata gtt ctt ggc atg ctg gat gtt cct tca aca gga gga      1488
Ala Gly Ser Ile Val Leu Gly Met Leu Asp Val Pro Ser Thr Gly Gly
            485                 490                 495 tgg cag aag tgg acc acc att tcc cat aca gtg aat gtg gat tca ggt      1536
Trp Gln Lys Trp Thr Thr Ile Ser His Thr Val Asn Val Asp Ser Gly
            500                 505                 510 aca tat aac ttg ggg atc tat gtt caa cga gcc agc tgg aat atc aac      1584
Thr Tyr Asn Leu Gly Ile Tyr Val Gln Arg Ala Ser Trp Asn Ile Asn
            515                 520                 525 tgg ata aag att aca aaa ata cct gaa cag tca aat ttg aat caa ggg      1632
Trp Ile Lys Ile Thr Lys Ile Pro Glu Gln Ser Asn Leu Asn Gln Gly
530                 535                 540 cgt cgt aat tct aaa tta att cag gca gaa agt tat ttt agt tac tca      1680
Arg Arg Asn Ser Lys Leu Ile Gln Ala Glu Ser Tyr Phe Ser Tyr Ser
545                 550                 555                 560 gaa gta caa ctg gaa gat acc tta gat gta gga ggt gga aag aat gtt      1728
Glu Val Gln Leu Glu Asp Thr Leu Asp Val Gly Gly Gly Lys Asn Val
            565                 570                 575
```

```
aaa tgt gat aaa gaa ggg gcc tgg atg gct tac aag gat att gat ttc    1776
Lys Cys Asp Lys Glu Gly Ala Trp Met Ala Tyr Lys Asp Ile Asp Phe
            580                 585                 590 ccc agt tca gga agt tat cga gta gaa tac aga gtg gca agt gaa cgt    1824
Pro Ser Ser Gly Ser Tyr Arg Val Glu Tyr Arg Val Ala Ser Glu Arg
            595                 600                 605 gca gga gga aag ctg tcc cta gat ttg aat gca ggc tct ata gtg ctt    1872
Ala Gly Gly Lys Leu Ser Leu Asp Leu Asn Ala Gly Ser Ile Val Leu
610                 615                 620 ggc atg ctg gat att cct tca aca gga gga ttg cag aag tgg acc acc    1920
Gly Met Leu Asp Ile Pro Ser Thr Gly Gly Leu Gln Lys Trp Thr Thr
625                 630                 635                 640 att tct cat ata gtg aat gtg gat tta ggt aca tat aac ttg gga att    1968
Ile Ser His Ile Val Asn Val Asp Leu Gly Thr Tyr Asn Leu Gly Ile
                645                 650                 655 tat gtt caa aaa gcc agt tgg aat atc aat tgg att aga att aca aaa    2016
Tyr Val Gln Lys Ala Ser Trp Asn Ile Asn Trp Ile Arg Ile Thr Lys
            660                 665                 670 gtg tag                                                            2022
Val

<210> SEQ ID NO 12
<211> LENGTH: 673
<212> TYPE: PRT
<213> ORGANISM: Tachyporus sp.

<400> SEQUENCE: 12

Met Leu Val Leu Leu Cys Cys Val Val Leu His Val Gly Val Ala Arg
1               5                   10                  15

Ile Cys Cys Ser His Glu Pro Lys Trp Gln Leu Val Trp Ser Asp Glu
                20                  25                  30

Phe Thr Asn Gly Ile Ser Ser Asp Trp Glu Phe Glu Met Gly Asn Gly
            35                  40                  45

Leu Asn Gly Trp Gly Asn Asn Glu Leu Gln Tyr Tyr Arg Arg Glu Asn
        50                  55                  60

Ala Gln Val Glu Gly Gly Lys Leu Val Ile Thr Ala Lys Arg Glu Asp
65                  70                  75                  80

Tyr Asp Gly Phe Lys Tyr Thr Ser Ala Arg Leu Lys Thr Gln Phe Asp
                85                  90                  95

Lys Ser Trp Lys Tyr Gly Lys Ile Glu Ala Lys Met Ala Ile Pro Ser
            100                 105                 110

Phe Arg Gly Val Trp Val Met Phe Trp Met Ser Gly Asp Asn Thr Asn
        115                 120                 125

Tyr Val Arg Trp Pro Ser Ser Gly Glu Ile Asp Phe Ile Glu His Arg
    130                 135                 140

Asn Thr Asn Asn Glu Lys Val Arg Gly Thr Ile His Trp Ser Thr Pro
145                 150                 155                 160

Asp Gly Ala His Ala His His Asn Arg Glu Ser Asn Thr Asn Gly Ile
                165                 170                 175

Asp Tyr His Ile Tyr Ser Val Glu Trp Asn Ser Ser Ile Val Lys Trp
            180                 185                 190

Phe Val Asn Gly Asn Gln Tyr Phe Glu Val Lys Ile Gln Gly Gly Val
        195                 200                 205

Asn Gly Lys Ser Ala Phe Arg Asn Lys Val Phe Val Ile Leu Asn Met
    210                 215                 220

Ala Ile Gly Gly Asn Trp Pro Gly Phe Asp Val Ala Asp Glu Ala Phe
225                 230                 235                 240
```

-continued

Pro Ala Lys Met Tyr Ile Asp Tyr Val Arg Val Tyr Gln Asp Ala Ser
                245                 250                 255

Thr Ser Ser Pro Val Gly Asp Thr Ser Leu Asp Gly Tyr Tyr Phe Val
            260                 265                 270

Gln Asn Arg His Ser Glu Leu Tyr Leu Asp Val Thr Asp Ala Ser Asn
        275                 280                 285

Glu Asp Gly Ala Phe Leu Gln Gln Trp Ser Tyr Ser Gly Asn Glu Asn
    290                 295                 300

Gln Gln Phe Asp Phe Glu His Leu Glu Asn Asn Val Tyr Lys Ile Thr
305                 310                 315                 320

Asn Lys Lys Ser Gly Lys Ser Leu Asp Val Tyr Asn Phe Gly Thr Glu
                325                 330                 335

Asn Gly Val Arg Ile Gln Gln Trp Ser Tyr Gly Gly Ala Arg Asn Gln
            340                 345                 350

Gln Phe Thr Val Gln Ser Val Gly Asp Gly Tyr Tyr Lys Ile Ile Pro
        355                 360                 365

Arg Gly Ser Gly Lys Leu Val Glu Val Ala Asp Phe Ser Lys Asp Ala
    370                 375                 380

Gly Gly Lys Ile Gln Gln Trp Ser Asp Asn Asn Gln Leu Ser Gly Gln
385                 390                 395                 400

Trp Lys Leu Ile Lys Ser Lys Ser Tyr Ser Lys Leu Ile Gln Ala Glu
                405                 410                 415

Ser Tyr Phe Asp Ser Ser Lys Val Gln Leu Glu Asp Thr Ser Asp Val
            420                 425                 430

Gly Gly Gly Lys Asn Val Lys Cys Asp Asn Glu Gly Ala Trp Met Ala
        435                 440                 445

Tyr Lys Asp Ile Asp Phe Pro Ser Ser Gly Asn Tyr Arg Ile Glu Tyr
    450                 455                 460

Arg Val Ala Ser Glu Arg Ala Gly Gly Lys Leu Ser Leu Asp Leu Asn
465                 470                 475                 480

Ala Gly Ser Ile Val Leu Gly Met Leu Asp Val Pro Ser Thr Gly Gly
                485                 490                 495

Trp Gln Lys Trp Thr Thr Ile Ser His Thr Val Asn Val Asp Ser Gly
            500                 505                 510

Thr Tyr Asn Leu Gly Ile Tyr Val Gln Arg Ala Ser Trp Asn Ile Asn
        515                 520                 525

Trp Ile Lys Ile Thr Lys Ile Pro Glu Gln Ser Asn Leu Asn Gln Gly
    530                 535                 540

Arg Arg Asn Ser Lys Leu Ile Gln Ala Glu Ser Tyr Phe Ser Tyr Ser
545                 550                 555                 560

Glu Val Gln Leu Glu Asp Thr Leu Asp Val Gly Gly Gly Lys Asn Val
                565                 570                 575

Lys Cys Asp Lys Glu Gly Ala Trp Met Ala Tyr Lys Asp Ile Asp Phe
            580                 585                 590

Pro Ser Ser Gly Ser Tyr Arg Val Glu Tyr Arg Val Ala Ser Glu Arg
        595                 600                 605

Ala Gly Gly Lys Leu Ser Leu Asp Leu Asn Ala Gly Ser Ile Val Leu
    610                 615                 620

Gly Met Leu Asp Ile Pro Ser Thr Gly Gly Leu Gln Lys Trp Thr Thr
625                 630                 635                 640

Ile Ser His Ile Val Asn Val Asp Leu Gly Thr Tyr Asn Leu Gly Ile
                645                 650                 655

Tyr Val Gln Lys Ala Ser Trp Asn Ile Asn Trp Ile Arg Ile Thr Lys
              660                 665                 670
Val

<210> SEQ ID NO 13
<211> LENGTH: 1218
<212> TYPE: DNA
<213> ORGANISM: Tachyporus sp.
<220> FEATURE:
<221> NAME/KEY: CDS
<222> LOCATION: (1)..(1218)

<400> SEQUENCE: 13

```
ggt tac tat ttt gtc caa aac agg cac agt gaa ttg tat ctt gat gtc      48
Gly Tyr Tyr Phe Val Gln Asn Arg His Ser Glu Leu Tyr Leu Asp Val
1               5                   10                  15 act gat gcc agt aac gaa gat gga gca ttt ctg caa caa tgg tct tat      96
Thr Asp Ala Ser Asn Glu Asp Gly Ala Phe Leu Gln Gln Trp Ser Tyr
            20                  25                  30 agt ggt aat gag aac caa cag ttt gat ttt gag cat ctc gaa aat aat     144
Ser Gly Asn Glu Asn Gln Gln Phe Asp Phe Glu His Leu Glu Asn Asn
        35                  40                  45 gtt tat aaa att act aat aaa aaa agt gga aaa tct ttg gat gtt tat     192
Val Tyr Lys Ile Thr Asn Lys Lys Ser Gly Lys Ser Leu Asp Val Tyr
 50                  55                  60 aat ttt ggg act gag aat ggt gtt aga atc caa cag tgg tca tat gga     240
Asn Phe Gly Thr Glu Asn Gly Val Arg Ile Gln Gln Trp Ser Tyr Gly
 65                  70                  75                  80 ggg gct cgc aat cag cag ttt act gta caa agt gtt ggt gat ggt tat     288
Gly Ala Arg Asn Gln Gln Phe Thr Val Gln Ser Val Gly Asp Gly Tyr
                85                  90                  95 tat aag att att cca cgc ggc agt gga aag tta gtg gaa gta gca gat     336
Tyr Lys Ile Ile Pro Arg Gly Ser Gly Lys Leu Val Glu Val Ala Asp
            100                 105                 110 ttt agt aaa gat gca gga ggg aag ata caa caa tgg tct gat aac aac     384
Phe Ser Lys Asp Ala Gly Gly Lys Ile Gln Gln Trp Ser Asp Asn Asn
        115                 120                 125 caa tta tct gga cag tgg aaa ctt att aaa agt aaa agt tat tct aaa     432
Gln Leu Ser Gly Gln Trp Lys Leu Ile Lys Ser Lys Ser Tyr Ser Lys
    130                 135                 140 tta att cag gca gaa agt tat ttt gat tcc tca aaa gta caa ttg gaa     480
Leu Ile Gln Ala Glu Ser Tyr Phe Asp Ser Ser Lys Val Gln Leu Glu
145                 150                 155                 160 gat acc tca gat gta gga ggt ggg aag aat gtt aaa tgt gat aat gaa     528
Asp Thr Ser Asp Val Gly Gly Gly Lys Asn Val Lys Cys Asp Asn Glu
                165                 170                 175 gga gcc tgg atg gct tat aag gat att gat ttc ccc agt tca ggt aat     576
Gly Ala Trp Met Ala Tyr Lys Asp Ile Asp Phe Pro Ser Ser Gly Asn
            180                 185                 190 tat cga ata gaa tac aga gta gca agt gaa cgt gca gga gga aag ctg     624
Tyr Arg Ile Glu Tyr Arg Val Ala Ser Glu Arg Ala Gly Gly Lys Leu
        195                 200                 205 tct ctg gat ttg aat gca ggc tct ata gtt ctt ggc atg ctg gat gtt     672
Ser Leu Asp Leu Asn Ala Gly Ser Ile Val Leu Gly Met Leu Asp Val
    210                 215                 220 cct tca aca gga gga tgg cag aag tgg acc acc att tcc cat aca gtg     720
Pro Ser Thr Gly Gly Trp Gln Lys Trp Thr Thr Ile Ser His Thr Val
225                 230                 235                 240 aat gtg gat tca ggt aca tat aac ttg ggg atc tat gtt caa cga gcc     768
Asn Val Asp Ser Gly Thr Tyr Asn Leu Gly Ile Tyr Val Gln Arg Ala
                245                 250                 255
```

```
agc tgg aat atc aac tgg ata aag att aca aaa ata cct gaa cag tca     816
Ser Trp Asn Ile Asn Trp Ile Lys Ile Thr Lys Ile Pro Glu Gln Ser
        260                 265                 270 aat ttg aat caa ggg cgt cgt aat tct aaa tta att cag gca gaa agt     864
Asn Leu Asn Gln Gly Arg Arg Asn Ser Lys Leu Ile Gln Ala Glu Ser
    275                 280                 285 tat ttt agt tac tca gaa gta caa ctg gaa gat acc tta gat gta gga     912
Tyr Phe Ser Tyr Ser Glu Val Gln Leu Glu Asp Thr Leu Asp Val Gly
290                 295                 300 ggt gga aag aat gtt aaa tgt gat aaa gaa ggg gcc tgg atg gct tac     960
Gly Gly Lys Asn Val Lys Cys Asp Lys Glu Gly Ala Trp Met Ala Tyr
305                 310                 315                 320 aag gat att gat ttc ccc agt tca gga agt tat cga gta gaa tac aga    1008
Lys Asp Ile Asp Phe Pro Ser Ser Gly Ser Tyr Arg Val Glu Tyr Arg
                325                 330                 335 gtg gca agt gaa cgt gca gga gga aag ctg tcc cta gat ttg aat gca    1056
Val Ala Ser Glu Arg Ala Gly Gly Lys Leu Ser Leu Asp Leu Asn Ala
            340                 345                 350 ggc tct ata gtg ctt ggc atg ctg gat att cct tca aca gga gga ttg    1104
Gly Ser Ile Val Leu Gly Met Leu Asp Ile Pro Ser Thr Gly Gly Leu
        355                 360                 365 cag aag tgg acc acc att tct cat ata gtg aat gtg gat tta ggt aca    1152
Gln Lys Trp Thr Thr Ile Ser His Ile Val Asn Val Asp Leu Gly Thr
    370                 375                 380 tat aac ttg gga att tat gtt caa aaa gcc agt tgg aat atc aat tgg    1200
Tyr Asn Leu Gly Ile Tyr Val Gln Lys Ala Ser Trp Asn Ile Asn Trp
385                 390                 395                 400 att aga att aca aaa gtg                                             1218
Ile Arg Ile Thr Lys Val
                405

<210> SEQ ID NO 14
<211> LENGTH: 406
<212> TYPE: PRT
<213> ORGANISM: Tachyporus sp.

<400> SEQUENCE: 14

Gly Tyr Tyr Phe Val Gln Asn Arg His Ser Glu Leu Tyr Leu Asp Val
1               5                   10                  15

Thr Asp Ala Ser Asn Glu Asp Gly Ala Phe Leu Gln Gln Trp Ser Tyr
            20                  25                  30

Ser Gly Asn Glu Asn Gln Gln Phe Asp Phe Glu His Leu Glu Asn Asn
        35                  40                  45

Val Tyr Lys Ile Thr Asn Lys Lys Ser Gly Lys Ser Leu Asp Val Tyr
    50                  55                  60

Asn Phe Gly Thr Glu Asn Gly Val Arg Ile Gln Gln Trp Ser Tyr Gly
65                  70                  75                  80

Gly Ala Arg Asn Gln Gln Phe Thr Val Gln Ser Val Gly Asp Gly Tyr
                85                  90                  95

Tyr Lys Ile Ile Pro Arg Gly Ser Gly Lys Leu Val Glu Val Ala Asp
            100                 105                 110

Phe Ser Lys Asp Ala Gly Gly Lys Ile Gln Gln Trp Ser Asp Asn Asn
        115                 120                 125

Gln Leu Ser Gly Gln Trp Lys Leu Ile Lys Ser Lys Ser Tyr Ser Lys
    130                 135                 140

Leu Ile Gln Ala Glu Ser Tyr Phe Asp Ser Ser Lys Val Gln Leu Glu
145                 150                 155                 160
```

```
Asp Thr Ser Asp Val Gly Gly Gly Lys Asn Val Lys Cys Asp Asn Glu
            165                 170                 175

Gly Ala Trp Met Ala Tyr Lys Asp Ile Asp Phe Pro Ser Ser Gly Asn
        180                 185                 190

Tyr Arg Ile Glu Tyr Arg Val Ala Ser Glu Arg Ala Gly Gly Lys Leu
        195                 200                 205

Ser Leu Asp Leu Asn Ala Gly Ser Ile Val Leu Gly Met Leu Asp Val
    210                 215                 220

Pro Ser Thr Gly Gly Trp Gln Lys Trp Thr Thr Ile Ser His Thr Val
225                 230                 235                 240

Asn Val Asp Ser Gly Thr Tyr Asn Leu Gly Ile Tyr Val Gln Arg Ala
                245                 250                 255

Ser Trp Asn Ile Asn Trp Ile Lys Ile Thr Lys Ile Pro Glu Gln Ser
                260                 265                 270

Asn Leu Asn Gln Gly Arg Arg Asn Ser Lys Leu Ile Gln Ala Glu Ser
            275                 280                 285

Tyr Phe Ser Tyr Ser Glu Val Gln Leu Glu Asp Thr Leu Asp Val Gly
    290                 295                 300

Gly Gly Lys Asn Val Lys Cys Asp Lys Glu Gly Ala Trp Met Ala Tyr
305                 310                 315                 320

Lys Asp Ile Asp Phe Pro Ser Ser Gly Ser Tyr Arg Val Glu Tyr Arg
                325                 330                 335

Val Ala Ser Glu Arg Ala Gly Gly Lys Leu Ser Leu Asp Leu Asn Ala
                340                 345                 350

Gly Ser Ile Val Leu Gly Met Leu Asp Ile Pro Ser Thr Gly Gly Leu
            355                 360                 365

Gln Lys Trp Thr Thr Ile Ser His Ile Val Asn Val Asp Leu Gly Thr
        370                 375                 380

Tyr Asn Leu Gly Ile Tyr Val Gln Lys Ala Ser Trp Asn Ile Asn Trp
385                 390                 395                 400

Ile Arg Ile Thr Lys Val
                405

<210> SEQ ID NO 15
<211> LENGTH: 792
<212> TYPE: DNA
<213> ORGANISM: Tachyporus sp.
<220> FEATURE:
<221> NAME/KEY: CDS
<222> LOCATION: (1)..(792)

<400> SEQUENCE: 15 tct aaa tta att cag gca gaa agt tat ttt gat tcc tca aaa gta caa      48
Ser Lys Leu Ile Gln Ala Glu Ser Tyr Phe Asp Ser Ser Lys Val Gln
1               5                   10                  15 ttg gaa gat acc tca gat gta gga ggt ggg aag aat gtt aaa tgt gat     96
Leu Glu Asp Thr Ser Asp Val Gly Gly Gly Lys Asn Val Lys Cys Asp
            20                  25                  30 aat gaa gga gcc tgg atg gct tat aag gat att gat ttc ccc agt tca    144
Asn Glu Gly Ala Trp Met Ala Tyr Lys Asp Ile Asp Phe Pro Ser Ser
        35                  40                  45 ggt aat tat cga ata gaa tac aga gta gca agt gaa cgt gca gga gga   192
Gly Asn Tyr Arg Ile Glu Tyr Arg Val Ala Ser Glu Arg Ala Gly Gly
    50                  55                  60 aag ctg tct ctg gat ttg aat gca ggc tct ata gtt ctt ggc atg ctg   240
Lys Leu Ser Leu Asp Leu Asn Ala Gly Ser Ile Val Leu Gly Met Leu
65                  70                  75                  80
```

```
gat gtt cct tca aca gga gga tgg cag aag tgg acc acc att tcc cat    288
Asp Val Pro Ser Thr Gly Gly Trp Gln Lys Trp Thr Thr Ile Ser His
            85                  90                  95 aca gtg aat gtg gat tca ggt aca tat aac ttg ggg atc tat gtt caa    336
Thr Val Asn Val Asp Ser Gly Thr Tyr Asn Leu Gly Ile Tyr Val Gln
                100                 105                 110 cga gcc agc tgg aat atc aac tgg ata aag att aca aaa ata cct gaa    384
Arg Ala Ser Trp Asn Ile Asn Trp Ile Lys Ile Thr Lys Ile Pro Glu
            115                 120                 125 cag tca aat ttg aat caa ggg cgt cgt aat tct aaa tta att cag gca    432
Gln Ser Asn Leu Asn Gln Gly Arg Arg Asn Ser Lys Leu Ile Gln Ala
    130                 135                 140 gaa agt tat ttt agt tac tca gaa gta caa ctg gaa gat acc tta gat    480
Glu Ser Tyr Phe Ser Tyr Ser Glu Val Gln Leu Glu Asp Thr Leu Asp
145                 150                 155                 160 gta gga ggt gga aag aat gtt aaa tgt gat aaa gaa ggg gcc tgg atg    528
Val Gly Gly Gly Lys Asn Val Lys Cys Asp Lys Glu Gly Ala Trp Met
                165                 170                 175 gct tac aag gat att gat ttc ccc agt tca gga agt tat cga gta gaa    576
Ala Tyr Lys Asp Ile Asp Phe Pro Ser Ser Gly Ser Tyr Arg Val Glu
            180                 185                 190 tac aga gtg gca agt gaa cgt gca gga gga aag ctg tcc cta gat ttg    624
Tyr Arg Val Ala Ser Glu Arg Ala Gly Gly Lys Leu Ser Leu Asp Leu
    195                 200                 205 aat gca ggc tct ata gtg ctt ggc atg ctg gat att cct tca aca gga    672
Asn Ala Gly Ser Ile Val Leu Gly Met Leu Asp Ile Pro Ser Thr Gly
210                 215                 220 gga ttg cag aag tgg acc acc att tct cat ata gtg aat gtg gat tta    720
Gly Leu Gln Lys Trp Thr Thr Ile Ser His Ile Val Asn Val Asp Leu
225                 230                 235                 240 ggt aca tat aac ttg gga att tat gtt caa aaa gcc agt tgg aat atc    768
Gly Thr Tyr Asn Leu Gly Ile Tyr Val Gln Lys Ala Ser Trp Asn Ile
                245                 250                 255 aat tgg att aga att aca aaa gtg                                    792
Asn Trp Ile Arg Ile Thr Lys Val
            260
```

<210> SEQ ID NO 16
<211> LENGTH: 264
<212> TYPE: PRT
<213> ORGANISM: Tachyporus sp.

<400> SEQUENCE: 16

```
Ser Lys Leu Ile Gln Ala Glu Ser Tyr Phe Asp Ser Ser Lys Val Gln
1               5                   10                  15

Leu Glu Asp Thr Ser Asp Val Gly Gly Gly Lys Asn Val Lys Cys Asp
            20                  25                  30

Asn Glu Gly Ala Trp Met Ala Tyr Lys Asp Ile Asp Phe Pro Ser Ser
        35                  40                  45

Gly Asn Tyr Arg Ile Glu Tyr Arg Val Ala Ser Glu Arg Ala Gly Gly
    50                  55                  60

Lys Leu Ser Leu Asp Leu Asn Ala Gly Ser Ile Val Leu Gly Met Leu
65                  70                  75                  80

Asp Val Pro Ser Thr Gly Gly Trp Gln Lys Trp Thr Thr Ile Ser His
                85                  90                  95

Thr Val Asn Val Asp Ser Gly Thr Tyr Asn Leu Gly Ile Tyr Val Gln
            100                 105                 110

Arg Ala Ser Trp Asn Ile Asn Trp Ile Lys Ile Thr Lys Ile Pro Glu
        115                 120                 125
```

```
            Gln Ser Asn Leu Asn Gln Gly Arg Arg Asn Ser Lys Leu Ile Gln Ala
                130                 135                 140

Glu Ser Tyr Phe Ser Tyr Ser Glu Val Gln Leu Glu Asp Thr Leu Asp
            145                 150                 155                 160

Val Gly Gly Gly Lys Asn Val Lys Cys Asp Lys Glu Gly Ala Trp Met
                            165                 170                 175

Ala Tyr Lys Asp Ile Asp Phe Pro Ser Ser Gly Ser Tyr Arg Val Glu
                        180                 185                 190

Tyr Arg Val Ala Ser Glu Arg Ala Gly Gly Lys Leu Ser Leu Asp Leu
                    195                 200                 205

Asn Ala Gly Ser Ile Val Leu Gly Met Leu Asp Ile Pro Ser Thr Gly
                210                 215                 220

Gly Leu Gln Lys Trp Thr Thr Ile Ser His Ile Val Asn Val Asp Leu
            225                 230                 235                 240

Gly Thr Tyr Asn Leu Gly Ile Tyr Val Gln Lys Ala Ser Trp Asn Ile
                            245                 250                 255

Asn Trp Ile Arg Ile Thr Lys Val
                        260

<210> SEQ ID NO 17
<211> LENGTH: 378
<212> TYPE: DNA
<213> ORGANISM: Tachyporus sp.
<220> FEATURE:
<221> NAME/KEY: CDS
<222> LOCATION: (1)..(378)

<400> SEQUENCE: 17 tct aaa tta att cag gca gaa agt tat ttt agt tac tca gaa gta caa          48
Ser Lys Leu Ile Gln Ala Glu Ser Tyr Phe Ser Tyr Ser Glu Val Gln
1               5                   10                  15 ctg gaa gat acc tta gat gta gga ggt gga aag aat gtt aaa tgt gat          96
Leu Glu Asp Thr Leu Asp Val Gly Gly Gly Lys Asn Val Lys Cys Asp
            20                  25                  30 aaa gaa ggg gcc tgg atg gct tac aag gat att gat ttc ccc agt tca         144
Lys Glu Gly Ala Trp Met Ala Tyr Lys Asp Ile Asp Phe Pro Ser Ser
        35                  40                  45 gga agt tat cga gta gaa tac aga gtg gca agt gaa cgt gca gga gga         192
Gly Ser Tyr Arg Val Glu Tyr Arg Val Ala Ser Glu Arg Ala Gly Gly
    50                  55                  60 aag ctg tcc cta gat ttg aat gca ggc tct ata gtg ctt ggc atg ctg         240
Lys Leu Ser Leu Asp Leu Asn Ala Gly Ser Ile Val Leu Gly Met Leu
65                  70                  75                  80 gat att cct tca aca gga gga ttg cag aag tgg acc acc att tct cat         288
Asp Ile Pro Ser Thr Gly Gly Leu Gln Lys Trp Thr Thr Ile Ser His
                85                  90                  95 ata gtg aat gtg gat tta ggt aca tat aac ttg gga att tat gtt caa         336
Ile Val Asn Val Asp Leu Gly Thr Tyr Asn Leu Gly Ile Tyr Val Gln
            100                 105                 110 aaa gcc agt tgg aat atc aat tgg att aga att aca aaa gtg                 378
Lys Ala Ser Trp Asn Ile Asn Trp Ile Arg Ile Thr Lys Val
        115                 120                 125

<210> SEQ ID NO 18
<211> LENGTH: 126
<212> TYPE: PRT
<213> ORGANISM: Tachyporus sp.

<400> SEQUENCE: 18
```

```
Ser Lys Leu Ile Gln Ala Glu Ser Tyr Phe Ser Tyr Ser Glu Val Gln
 1               5                  10                  15

Leu Glu Asp Thr Leu Asp Val Gly Gly Lys Asn Val Lys Cys Asp
             20                  25                  30

Lys Glu Gly Ala Trp Met Ala Tyr Lys Asp Ile Asp Phe Pro Ser Ser
             35                  40                  45

Gly Ser Tyr Arg Val Glu Tyr Arg Val Ala Ser Glu Arg Ala Gly Gly
         50                  55                  60

Lys Leu Ser Leu Asp Leu Asn Ala Gly Ser Ile Val Leu Gly Met Leu
 65              70                  75                  80

Asp Ile Pro Ser Thr Gly Gly Leu Gln Lys Trp Thr Thr Ile Ser His
             85                  90                  95

Ile Val Asn Val Asp Leu Gly Thr Tyr Asn Leu Gly Ile Tyr Val Gln
             100                 105                 110

Lys Ala Ser Trp Asn Ile Asn Trp Ile Arg Ile Thr Lys Val
             115                 120                 125

<210> SEQ ID NO 19
<211> LENGTH: 840
<212> TYPE: DNA
<213> ORGANISM: Tachyporus sp.
<220> FEATURE:
<221> NAME/KEY: CDS
<222> LOCATION: (1)..(840)

<400> SEQUENCE: 19 ggt tac tat ttt gtc caa aac agg cac agt gaa ttg tat ctt gat gtc        48
Gly Tyr Tyr Phe Val Gln Asn Arg His Ser Glu Leu Tyr Leu Asp Val
 1               5                  10                  15 act gat gcc agt aac gaa gat gga gca ttt ctg caa caa tgg tct tat        96
Thr Asp Ala Ser Asn Glu Asp Gly Ala Phe Leu Gln Gln Trp Ser Tyr
             20                  25                  30 agt ggt aat gag aac caa cag ttt gat ttt gag cat ctc gaa aat aat       144
Ser Gly Asn Glu Asn Gln Gln Phe Asp Phe Glu His Leu Glu Asn Asn
         35                  40                  45 gtt tat aaa att act aat aaa aaa agt gga aaa tct ttg gat gtt tat       192
Val Tyr Lys Ile Thr Asn Lys Lys Ser Gly Lys Ser Leu Asp Val Tyr
     50                  55                  60 aat ttt ggg act gag aat ggt gtt aga atc caa cag tgg tca tat gga       240
Asn Phe Gly Thr Glu Asn Gly Val Arg Ile Gln Gln Trp Ser Tyr Gly
 65              70                  75                  80 ggg gct cgc aat cag cag ttt act gta caa agt gtt ggt gat ggt tat       288
Gly Ala Arg Asn Gln Gln Phe Thr Val Gln Ser Val Gly Asp Gly Tyr
             85                  90                  95 tat aag att att cca cgc ggc agt gga aag tta gtg gaa gta gca gat       336
Tyr Lys Ile Ile Pro Arg Gly Ser Gly Lys Leu Val Glu Val Ala Asp
             100                 105                 110 ttt agt aaa gat gca gga ggg aag ata caa caa tgg tct gat aac aac       384
Phe Ser Lys Asp Ala Gly Gly Lys Ile Gln Gln Trp Ser Asp Asn Asn
             115                 120                 125 caa tta tct gga cag tgg aaa ctt att aaa agt aaa agt tat tct aaa       432
Gln Leu Ser Gly Gln Trp Lys Leu Ile Lys Ser Lys Ser Tyr Ser Lys
 130                 135                 140 tta att cag gca gaa agt tat ttt gat tcc tca aaa gta caa ttg gaa       480
Leu Ile Gln Ala Glu Ser Tyr Phe Asp Ser Ser Lys Val Gln Leu Glu
 145                 150                 155                 160 gat acc tca gat gta gga ggt ggg aag aat gtt aaa tgt gat aat gaa       528
Asp Thr Ser Asp Val Gly Gly Gly Lys Asn Val Lys Cys Asp Asn Glu
             165                 170                 175
```

```
gga gcc tgg atg gct tat aag gat att gat ttc ccc agt tca ggt aat       576
Gly Ala Trp Met Ala Tyr Lys Asp Ile Asp Phe Pro Ser Ser Gly Asn
            180                 185                 190 tat cga ata gaa tac aga gta gca agt gaa cgt gca gga gga aag ctg       624
Tyr Arg Ile Glu Tyr Arg Val Ala Ser Glu Arg Ala Gly Gly Lys Leu
        195                 200                 205 tct ctg gat ttg aat gca ggc tct ata gtt ctt ggc atg ctg gat gtt       672
Ser Leu Asp Leu Asn Ala Gly Ser Ile Val Leu Gly Met Leu Asp Val
    210                 215                 220 cct tca aca gga gga tgg cag aag tgg acc acc att tcc cat aca gtg       720
Pro Ser Thr Gly Gly Trp Gln Lys Trp Thr Thr Ile Ser His Thr Val
225                 230                 235                 240 aat gtg gat tca ggt aca tat aac ttg ggg atc tat gtt caa cga gcc       768
Asn Val Asp Ser Gly Thr Tyr Asn Leu Gly Ile Tyr Val Gln Arg Ala
                245                 250                 255 agc tgg aat atc aac tgg ata aag att aca aaa ata cct gaa cag tca       816
Ser Trp Asn Ile Asn Trp Ile Lys Ile Thr Lys Ile Pro Glu Gln Ser
            260                 265                 270 aat ttg aat caa ggg cgt cgt aat                                       840
Asn Leu Asn Gln Gly Arg Arg Asn
        275                 280

<210> SEQ ID NO 20
<211> LENGTH: 280
<212> TYPE: PRT
<213> ORGANISM: Tachyporus sp.

<400> SEQUENCE: 20

Gly Tyr Tyr Phe Val Gln Asn Arg His Ser Glu Leu Tyr Leu Asp Val
1               5                   10                  15

Thr Asp Ala Ser Asn Glu Asp Gly Ala Phe Leu Gln Gln Trp Ser Tyr
            20                  25                  30

Ser Gly Asn Glu Asn Gln Gln Phe Asp Phe Glu His Leu Glu Asn Asn
        35                  40                  45

Val Tyr Lys Ile Thr Asn Lys Lys Ser Gly Lys Ser Leu Asp Val Tyr
    50                  55                  60

Asn Phe Gly Thr Glu Asn Gly Val Arg Ile Gln Gln Trp Ser Tyr Gly
65                  70                  75                  80

Gly Ala Arg Asn Gln Gln Phe Thr Val Gln Ser Val Gly Asp Gly Tyr
                85                  90                  95

Tyr Lys Ile Ile Pro Arg Gly Ser Gly Lys Leu Val Glu Val Ala Asp
            100                 105                 110

Phe Ser Lys Asp Ala Gly Gly Lys Ile Gln Gln Trp Ser Asp Asn Asn
        115                 120                 125

Gln Leu Ser Gly Gln Trp Lys Leu Ile Lys Ser Lys Ser Tyr Ser Lys
    130                 135                 140

Leu Ile Gln Ala Glu Ser Tyr Phe Asp Ser Ser Lys Val Gln Leu Glu
145                 150                 155                 160

Asp Thr Ser Asp Val Gly Gly Lys Asn Val Lys Cys Asp Asn Glu
                165                 170                 175

Gly Ala Trp Met Ala Tyr Lys Asp Ile Asp Phe Pro Ser Ser Gly Asn
            180                 185                 190

Tyr Arg Ile Glu Tyr Arg Val Ala Ser Glu Arg Ala Gly Gly Lys Leu
        195                 200                 205

Ser Leu Asp Leu Asn Ala Gly Ser Ile Val Leu Gly Met Leu Asp Val
    210                 215                 220

Pro Ser Thr Gly Gly Trp Gln Lys Trp Thr Thr Ile Ser His Thr Val
```

```
                225                 230                 235                 240
Asn Val Asp Ser Gly Thr Tyr Asn Leu Gly Ile Tyr Val Gln Arg Ala
                    245                 250                 255

Ser Trp Asn Ile Asn Trp Ile Lys Ile Thr Lys Ile Pro Glu Gln Ser
                260                 265                 270

Asn Leu Asn Gln Gly Arg Arg Asn
            275                 280
```

```
<210> SEQ ID NO 21
<211> LENGTH: 16
<212> TYPE: DNA
<213> ORGANISM: Artificial
<220> FEATURE:
<223> OTHER INFORMATION: oligonucleotide primer

<400> SEQUENCE: 21
gcaatgttgg tgttgc                                                        16

<210> SEQ ID NO 22
<211> LENGTH: 22
<212> TYPE: DNA
<213> ORGANISM: Artificial
<220> FEATURE:
<223> OTHER INFORMATION: oligonucleotide primer

<400> SEQUENCE: 22
gaagaaacaa cagctgttga cc                                                 22

<210> SEQ ID NO 23
<211> LENGTH: 22
<212> TYPE: DNA
<213> ORGANISM: Artificial
<220> FEATURE:
<223> OTHER INFORMATION: oligonucleotide primer

<400> SEQUENCE: 23
aatacacctt ctcctgttga cg                                                 22

<210> SEQ ID NO 24
<211> LENGTH: 22
<212> TYPE: DNA
<213> ORGANISM: Artificial
<220> FEATURE:
<223> OTHER INFORMATION: oligonucleotide primer

<400> SEQUENCE: 24
ctggattaag attacaaagg tt                                                 22

<210> SEQ ID NO 25
<211> LENGTH: 19
<212> TYPE: DNA
<213> ORGANISM: Artificial
<220> FEATURE:
<223> OTHER INFORMATION: oligonucleotide primer

<400> SEQUENCE: 25
tctaaattga ttcaggcag                                                     19

<210> SEQ ID NO 26
<211> LENGTH: 22
<212> TYPE: DNA
<213> ORGANISM: Artificial
<220> FEATURE:
<223> OTHER INFORMATION: oligonucleotide primer
```

<400> SEQUENCE: 26
ctggattaag attacaaagg tt                                                     22

<210> SEQ ID NO 27
<211> LENGTH: 23
<212> TYPE: DNA
<213> ORGANISM: Artificial
<220> FEATURE:
<223> OTHER INFORMATION: oligonucleotide primer

<400> SEQUENCE: 27
tctagagtaa ttcaggcaga aag                                                    23

<210> SEQ ID NO 28
<211> LENGTH: 22
<212> TYPE: DNA
<213> ORGANISM: Artificial
<220> FEATURE:
<223> OTHER INFORMATION: oligonucleotide primer

<400> SEQUENCE: 28
ctggattaag attacaaagg tt                                                     22

<210> SEQ ID NO 29
<211> LENGTH: 22
<212> TYPE: DNA
<213> ORGANISM: Artificial
<220> FEATURE:
<223> OTHER INFORMATION: oligonucleotide primer

<400> SEQUENCE: 29
aatacacctt ctcctgttga cg                                                     22

<210> SEQ ID NO 30
<211> LENGTH: 24
<212> TYPE: DNA
<213> ORGANISM: Artificial
<220> FEATURE:
<223> OTHER INFORMATION: oligonucleotide primer

<400> SEQUENCE: 30
aatattacaa aagtatccag tcag                                                   24

<210> SEQ ID NO 31
<211> LENGTH: 24
<212> TYPE: DNA
<213> ORGANISM: Artificial
<220> FEATURE:
<223> OTHER INFORMATION: oligonucleotide primer

<400> SEQUENCE: 31
ggttactatt ttgtccaaaa cagg                                                   24

<210> SEQ ID NO 32
<211> LENGTH: 32
<212> TYPE: DNA
<213> ORGANISM: Artificial
<220> FEATURE:
<223> OTHER INFORMATION: oligonucleotide primer

<400> SEQUENCE: 32
ggaatatcaa ttggattaga attacaaaag tg                                          32

<210> SEQ ID NO 33
<211> LENGTH: 19

```
<212> TYPE: DNA
<213> ORGANISM: Artificial
<220> FEATURE:
<223> OTHER INFORMATION: oligonucleotide primer

<400> SEQUENCE: 33
tctaaattaa ttcaggcag                                              19

<210> SEQ ID NO 34
<211> LENGTH: 32
<212> TYPE: DNA
<213> ORGANISM: Artificial
<220> FEATURE:
<223> OTHER INFORMATION: oligonucleotide primer

<400> SEQUENCE: 34
ggaatatcaa ttggattaga attacaaaag tg                               32

<210> SEQ ID NO 35
<211> LENGTH: 19
<212> TYPE: DNA
<213> ORGANISM: Artificial
<220> FEATURE:
<223> OTHER INFORMATION: oligonucleotide primer

<400> SEQUENCE: 35
tctaaattaa ttcaggcag                                              19

<210> SEQ ID NO 36
<211> LENGTH: 32
<212> TYPE: DNA
<213> ORGANISM: Artificial
<220> FEATURE:
<223> OTHER INFORMATION: oligonucleotide primer

<400> SEQUENCE: 36
ggaatatcaa ttggattaga attacaaaag tg                               32

<210> SEQ ID NO 37
<211> LENGTH: 24
<212> TYPE: DNA
<213> ORGANISM: Artificial
<220> FEATURE:
<223> OTHER INFORMATION: oligonucleotide primer

<400> SEQUENCE: 37
ggttactatt ttgtccaaaa cagg                                        24

<210> SEQ ID NO 38
<211> LENGTH: 24
<212> TYPE: DNA
<213> ORGANISM: Artificial
<220> FEATURE:
<223> OTHER INFORMATION: oligonucleotide primer

<400> SEQUENCE: 38
aatttgaatc aagggcgtcg taat                                        24

<210> SEQ ID NO 39
<211> LENGTH: 15
<212> TYPE: DNA
<213> ORGANISM: Artificial
<220> FEATURE:
<223> OTHER INFORMATION: oligonucleotide primer

<400> SEQUENCE: 39
```
tacgaggcac caccg							15

<210> SEQ ID NO 40
<211> LENGTH: 18
<212> TYPE: DNA
<213> ORGANISM: Artificial
<220> FEATURE:
<223> OTHER INFORMATION: oligonucleotide primer

<400> SEQUENCE: 40
gttaaagttt ttgcaata							18

<210> SEQ ID NO 41
<211> LENGTH: 20
<212> TYPE: DNA
<213> ORGANISM: Artificial
<220> FEATURE:
<223> OTHER INFORMATION: oligonucleotide primer

<400> SEQUENCE: 41
atatcgtacg ctcaaatgcc							20

<210> SEQ ID NO 42
<211> LENGTH: 22
<212> TYPE: DNA
<213> ORGANISM: Artificial
<220> FEATURE:
<223> OTHER INFORMATION: oligonucleotide primer

<400> SEQUENCE: 42
ctttgtcaaa gttatcgcct ta							22

<210> SEQ ID NO 43
<211> LENGTH: 19
<212> TYPE: DNA
<213> ORGANISM: Artificial
<220> FEATURE:
<223> OTHER INFORMATION: oligonucleotide primer

<400> SEQUENCE: 43
gaggtcaagt ttcctgaag							19

<210> SEQ ID NO 44
<211> LENGTH: 18
<212> TYPE: DNA
<213> ORGANISM: Artificial
<220> FEATURE:
<223> OTHER INFORMATION: oligonucleotide primer

<400> SEQUENCE: 44
gtcagagtct atgcgctg							18

<210> SEQ ID NO 45
<211> LENGTH: 22
<212> TYPE: DNA
<213> ORGANISM: Artificial
<220> FEATURE:
<223> OTHER INFORMATION: oligonucleotide primer

<400> SEQUENCE: 45
tgttctaaat taattcaggc ag							22

<210> SEQ ID NO 46
<211> LENGTH: 23
<212> TYPE: DNA
<213> ORGANISM: Artificial

```
<220> FEATURE:
<223> OTHER INFORMATION: oligonucleotide primer

<400> SEQUENCE: 46
tgtctggatt aagattacaa agg                                              23

<210> SEQ ID NO 47
<211> LENGTH: 21
<212> TYPE: DNA
<213> ORGANISM: Artificial
<220> FEATURE:
<223> OTHER INFORMATION: oligonucleotide primer

<400> SEQUENCE: 47
gcctagcaaa ctcggaagat t                                                21

<210> SEQ ID NO 48
<211> LENGTH: 28
<212> TYPE: DNA
<213> ORGANISM: Artificial
<220> FEATURE:
<223> OTHER INFORMATION: oligonucleotide primer

<400> SEQUENCE: 48
atctatgact gtacgccaat gtccctag                                         28
```